United States Patent
Zhu et al.

(10) Patent No.: US 11,111,240 B2
(45) Date of Patent: Sep. 7, 2021

(54) SULTAM COMPOUND AND APPLICATION METHOD THEREOF

(71) Applicants: Chia Tai Tianqing Pharmaceutical Group Co., Ltd., Lianyungang (CN); Lianyungang Runzhong Pharmaceutical Co., Ltd., Lianyungang (CN); Centaurus Biopharma Co., Ltd., Beijing (CN)

(72) Inventors: Li Zhu, Beijing (CN); Xiaowei Duan, Beijing (CN); Liguang Dai, Beijing (CN); Zhao Yang, Beijing (CN); Yanqing Yang, Beijing (CN); Hui Zhang, Beijing (CN); Yuandong Hu, Beijing (CN); Yong Peng, Beijing (CN); Yongxin Han, Beijing (CN); Rui Zhao, Lianyungang (CN); Xin Tian, Lianyungang (CN); Shanchun Wang, Lianyungang (CN)

(73) Assignees: Chai Tai Tianqing Pharmaceutical Group Co., Ltd., Lianyungang (CN); Lianyungang Runzhong Pharmaceutical Co., Ltd., Lianyungang (CN); Centaurus Biopharma Co., Ltd., Beijing (CN)

( * ) Notice: Subject to any disclaimer, the term of this patent is extended or adjusted under 35 U.S.C. 154(b) by 419 days.

(21) Appl. No.: 16/086,721

(22) PCT Filed: Mar. 22, 2017

(86) PCT No.: PCT/CN2017/077612
§ 371 (c)(1),
(2) Date: Sep. 20, 2018

(87) PCT Pub. No.: WO2017/162157
PCT Pub. Date: Sep. 28, 2017

(65) Prior Publication Data
US 2021/0047314 A1 Feb. 18, 2021

(30) Foreign Application Priority Data
Mar. 22, 2016 (CN) .......................... 201610165138.6

(51) Int. Cl.
C07D 275/02 (2006.01)
A61K 31/425 (2006.01)
A61K 31/433 (2006.01)
A61P 35/00 (2006.01)
C07D 417/14 (2006.01)
C07D 417/04 (2006.01)

(52) U.S. Cl.
CPC ......... C07D 417/14 (2013.01); C07D 417/04 (2013.01)

(58) Field of Classification Search
CPC .. C07D 275/02; A61K 31/425; A61K 31/433; A61P 35/00
See application file for complete search history.

(56) References Cited

U.S. PATENT DOCUMENTS

2013/0190249 A1 7/2013 Lemieux

FOREIGN PATENT DOCUMENTS

| CN | 104136411 A | 11/2014 |
| WO | WO 2012/009678 A1 | 1/2012 |
| WO | WO 2013/107405 A1 | 7/2013 |
| WO | WO 2015/010297 A1 | 1/2015 |

OTHER PUBLICATIONS

Extended European Search Report in European Patent Application No. 17769434.6, dated Jul. 11, 2019 (7 pages).
International Search Report in International Application No. PCT/CN2017/077612, dated Jun. 23, 2017 (8 pages w/English translation).
Written Opinion in International Application No. PCT/CN2017/077612, dated Jun. 23, 2017 (15 pages w/English translation).

*Primary Examiner* — Bruck Kifle
(74) *Attorney, Agent, or Firm* — Nixon Peabody LLP

(57) ABSTRACT

Provided are a sultam compound having isocitrate dehydrogenase 1 (IDH1) inhibitory activity as represented by formula I or pharmaceutically-acceptable salts, solvates or hydrates thereof, a preparation method thereof, and a pharmaceutical composition containing the compound. The compound or the pharmaceutically-acceptable salts, solvates or hydrates thereof, and the pharmaceutical composition containing the compound can be used to treat IDH1 mutation-induced cancers.

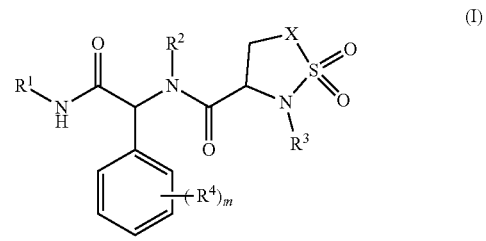

(I)

20 Claims, 2 Drawing Sheets

SULTAM COMPOUND AND APPLICATION METHOD THEREOF

CROSS-REFERENCE TO RELATED APPLICATIONS

This application is a U.S. national stage of PCT/CN2017/077612 filed on Mar. 22, 2017, which claims the benefit of Chinese Patent Application No. 201610061293.3 filed to the State Intellectual Property Office of the People's Republic of China on Mar. 22, 2016, the contents of which are incorporated herein by reference it their entireties.

DETAILED DESCRIPTION

Field of the Invention

The present application relates to a sultam compound for treating cancers and an application method thereof.

Background of the Invention

As the most important key enzyme in intracellular tricarboxylic acid cycle, IDH (full name: isocitrate dehydrogenase) can catalyze oxidative decarboxylation of isocitric acid to produce 2-oxoglutarate (i.e., α-ketoglutaric acid). There are two different subtypes of IDH, one using NAD(+) as an electron acceptor and the other using NADP(+) as the electron acceptor. Five types of IDH have been reported, three of which are NAD(+)-dependent isocitrate dehydrogenases, locating in the mitochondrial matrix; and the other two of which are NADP(+)-dependent isocitrate dehydrogenases, wherein one locates in the mitochondria and the other locates in the cytoplasm.

Researches have shown that many tumors (such as neuroglioma, sarcoma, and acute myelocytic leukemia) have an IDH mutation at arginine residue in a catalytic center (IDH1/R132H, IDH/R140Q, and IDH2/R172K). In 2009, Bleeker et al. have detected IDH1 mutations in 672 tumor samples obtained from different sources and 84 cell lines from different tumor lineages, and found that these mutations specifically and centrally occurred in gliomas (Bleeker et al., 2009. IDH1 mutations at residue p.R132(IDH1 (R132)) occur frequently in high-grade gliomas but not in other solid tumors. Hum Mutat. 30: 7-11). However, the later literature reports have shown that IDH1 mutations also exist in acute myeloid leukemia, prostate cancer, and paraganglioma and the like (Green et al., 2010, Somatic mutations of IDH1 and IDH2 in the leukemic transformation of myeloproliferative neoplasms. N Engl J Med. 362: 369-370). Bleeker et al. found that in IDH1 mutation cases, R132H accounts for 86.9%, and other types such as R132C, R132G, R132L, R132V and R132S account for a small proportion (Bleeker et al., 2009). The mutated IDH acquires a new ability to catalyze the conversion of α-ketoglutaric acid (α-KG) to 2-hydroxyglutaric acid (2-HG). Researches have shown that the structure of α-ketoglutaric acid is similar to that of 2-hydroxyglutaric acid, and 2-HG competes with α-KG, thereby reducing the activity of α-KG-dependent enzymes, and resulting in a hypermethylation of chromatin. Such supermethylation is considered to interfere with a normal cell differentiation, and leads to an excessive proliferation of immature cells, thereby causing cancers.

AG-120 (i.e., ivosidenib), an inhibitor of IDH1m developed by Agios Pharmaceuticals, has a significant efficacy for acute myeloid erythroleukemia, and researches directed to other malignant solid tumors such as bile duct cancer, chondrosarcoma, neuroglioma are also underway.

SUMMARY OF THE INVENTION

In one aspect, the present application provides a compound represented by formula I or a pharmaceutically acceptable salt, solvate or hydrate thereof,

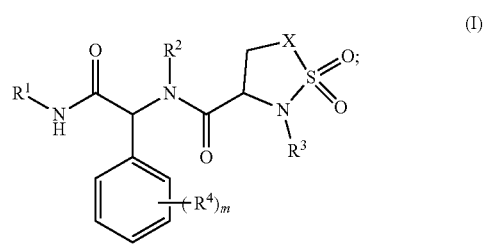

wherein,

X is selected from $CH_2$ or $NR^5$;

$R^1$ is selected from $C_{3-6}$ cycloalkyl or $C_{3-6}$ heterocycloalkyl, which may be optionally substituted with one or more groups independently selected from $R^6$;

$R^2$ is selected from phenyl or 5- to 6-membered heteroaryl containing 1 to 2 heteroatoms selected from N, O or S, which may be optionally substituted with one or more groups independently selected from $R^7$;

$R^3$ is selected from phenyl, 5- to 6-membered heteroaryl containing 1 to 2 heteroatoms selected from N or O or S, phenyl $CH_2$—, or 5- to 6-membered heteroaryl $CH_2$— containing 1 to 2 heteroatoms selected from N or O or S, which may be optionally substituted with one or more groups independently selected from $R^8$;

$R^4$ is selected from halogen, amino, hydroxyl, $C_{1-3}$ haloalkyl or $C_{1-6}$ alkyl;

$R^5$ is selected from hydrogen or $C_{1-6}$ alkyl;

$R^6$ is selected from halogen, amino, hydroxyl, cyano, $C_{1-3}$ haloalkyl, $C_{1-6}$ alkyl or $C_{3-6}$ cycloalkyl;

$R^7$ is selected from halogen, amino, hydroxyl, cyano, $C_{1-3}$ haloalkyl, oxo,

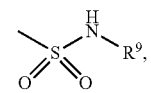

$C_{1-6}$ alkyl or $C_{3-6}$ cycloalkyl;

$R^8$ is selected from halogen, amino, hydroxyl, cyano, $C_{1-3}$ haloalkyl, $C_{1-6}$ alkyl, $C_{3-6}$ cycloalkyl, $C_{2-6}$ alkenyl or $C_{2-6}$ alkynyl;

$R^9$ is selected from H, $C_{1-6}$ alkyl, $C_{3-6}$ cycloalkyl, $C_{3-6}$ heterocycloalkyl, phenyl, or 5- to 6-membered heteroaryl containing 1 to 2 heteroatoms selected from N or O or S, which may be optionally substituted with one or more groups independently selected from $R^{10}$;

$R^{10}$ is selected from halogen, amino, hydroxyl, cyano, $C_{1-3}$ haloalkyl, $C_{1-6}$ alkyl or $C_{3-6}$ cycloalkyl;

m is 0 or 1.

As a preferred embodiment of the present application, in the compound represented by formula I or the pharmaceutically acceptable salt, solvate or hydrate thereof, substituents are defined as follows:

X is selected from CH$_2$ or NR$^5$;

R$^1$ is selected from C$_{3-6}$ cycloalkyl or C$_{3-6}$ heterocycloalkyl, which may be optionally substituted with one or more groups independently selected from R$^6$;

R$^2$ is selected from phenyl or 5- to 6-membered heteroaryl containing 1 to 2 heteroatoms selected from N, O or S, which may be optionally substituted with one or more groups independently selected from R$^7$;

R$^3$ is selected from phenyl, 5- to 6-membered heteroaryl containing 1 to 2 heteroatoms selected from N or O or S, phenyl CH$_2$—, or 5- to 6-membered heteroaryl CH$_2$— containing 1 to 2 heteroatoms selected from N or O or S, which may be optionally substituted with one or more groups independently selected from R$^8$;

R$^4$ is selected from halogen, amino, hydroxyl, C$_{1-3}$ haloalkyl or C$_{1-6}$ alkyl;

R$^5$ is selected from hydrogen or C$_{1-6}$ alkyl;

R$^6$ is selected from halogen, amino, hydroxyl, cyano, C$_{1-3}$ haloalkyl, C$_{1-6}$ alkyl or C$_{3-6}$ cycloalkyl;

R$^7$ is selected from halogen, amino, hydroxyl, cyano, C$_{1-3}$ haloalkyl, aminosulfonyl, N-substituted aminosulfonyl, C$_{1-6}$ alkyl or C$_{3-6}$ cycloalkyl;

R$^8$ is selected from halogen, amino, hydroxyl, cyano, C$_{1-3}$ haloalkyl, C$_{1-6}$ alkyl, C$_{3-6}$ cycloalkyl, C$_{2-6}$ alkenyl or C$_{2-6}$ alkynyl;

m is 0 or 1.

In one embodiment of the compound of formula I in the present application, R$^4$ is selected from F, Cl, Br, or trifluoromethyl.

In another aspect, the present application provides a compound represented by formula I-1 or a pharmaceutically acceptable salt, solvate or hydrate thereof:

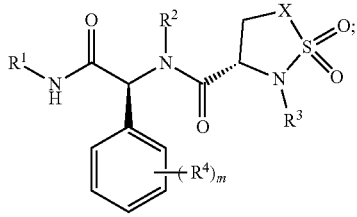

(I-1)

wherein, the substituents are defined as described for the compound of formula I.

In another aspect, the present application provides a compound represented by formula I-2 or a pharmaceutically acceptable salt, solvate or hydrate thereof:

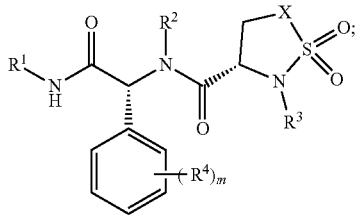

(I-2)

wherein, the substituents are defined as described for the compound of formula I.

As one embodiment of the present application, a compound represented by formula II or a pharmaceutically acceptable salt, solvate or hydrate thereof is provided:

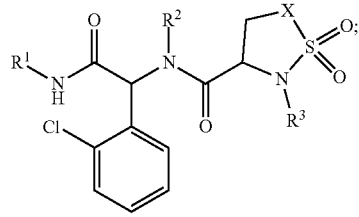

(II)

wherein,

X is selected from CH$_2$ or NR$^5$;

R$^1$ is selected from C$_{3-6}$ cycloalkyl or C$_{3-6}$ heterocycloalkyl, which may be optionally substituted with one or more groups independently selected from R$^6$;

R$^2$ is selected from phenyl or 5- to 6-membered heteroaryl containing 1 to 2 heteroatoms selected from N, O or S, which may be optionally substituted with one or more groups independently selected from R$^7$;

R$^3$ is selected from phenyl, 5- to 6-membered heteroaryl containing 1 to 2 heteroatoms selected from N or O or S, phenyl CH$_2$—, or 5- to 6-membered heteroaryl CH$_2$— containing 1 to 2 heteroatoms selected from N or O or S, which may be optionally substituted with one or more groups independently selected from R$^8$;

R$^5$ is selected from hydrogen or C$_{1-6}$ alkyl;

R$^6$ is selected from halogen, amino, hydroxyl, cyano, C$_{1-3}$ haloalkyl, C$_{1-6}$ alkyl or C$_{3-6}$ cycloalkyl;

R$^7$ is selected from halogen, amino, hydroxyl, cyano, C$_{1-3}$ haloalkyl, oxo,

C$_{1-6}$ alkyl or C$_{3-6}$ cycloalkyl;

R$^8$ is selected from halogen, amino, hydroxyl, cyano, C$_{1-3}$ haloalkyl, C$_{1-6}$ alkyl, C$_{3-6}$ cycloalkyl, C$_{2-6}$ alkenyl or C$_{2-6}$ alkynyl;

R$^9$ is selected from H, C$_{1-6}$ alkyl, C$_{3-6}$ cycloalkyl, C$_{3-6}$ heterocycloalkyl, phenyl, or 5- to 6-membered heteroaryl containing 1 to 2 heteroatoms selected from N or O or S, which may be optionally substituted with one or more groups independently selected from R$^{10}$;

R$^{10}$ is selected from halogen, amino, hydroxyl, cyano, C$_{1-3}$ haloalkyl, C$_{1-6}$ alkyl or C$_{3-6}$ cycloalkyl.

As a preferred embodiment of the present application, in the compound represented by formula II or the pharmaceutically acceptable salt, solvate or hydrate thereof, the substituents are defined as follows:

X is selected from CH$_2$ or NR$^5$;

R$^1$ is selected from C$_{3-6}$ cycloalkyl or C$_{3-6}$ heterocycloalkyl, which may be optionally substituted with one or more groups independently selected from R$^6$;

R$^2$ is selected from phenyl or 5- to 6-membered heteroaryl containing 1 to 2 heteroatoms selected from N, O or S, which may be optionally substituted with one or more groups independently selected from R$^7$;

R$^3$ is selected from phenyl, 5- to 6-membered heteroaryl containing 1 to 2 heteroatoms selected from N or O or S, phenyl CH$_2$—, or 5- to 6-membered heteroaryl CH$_2$— containing 1 to 2 heteroatoms selected from N or O or S, which may be optionally substituted with one or more groups independently selected from $R^8$;

$R^5$ is selected from hydrogen or $C_{1-6}$ alkyl;

$R^6$ is selected from halogen, amino, hydroxyl, cyano, $C_{1-3}$ haloalkyl, $C_{1-6}$ alkyl or $C_{3-6}$ cycloalkyl;

$R^7$ is selected from halogen, amino, hydroxyl, cyano, $C_{1-3}$ haloalkyl, aminosulfonyl, N-substituted aminosulfonyl, $C_{1-6}$ alkyl or $C_{3-6}$ cycloalkyl;

$R^8$ is selected from halogen, amino, hydroxyl, cyano, $C_{1-3}$ haloalkyl, $C_{1-6}$ alkyl, $C_{3-6}$ cycloalkyl, $C_{2-6}$ alkenyl or $C_{2-6}$ alkynyl.

In one embodiment of the compound of formula II in the present application, X is selected from $CH_2$, NH or $N(CH_3)$.

In one embodiment of the compound of formula II in the present application, $R^5$ is selected from hydrogen, methyl, ethyl, propyl, isopropyl, butyl, isobutyl or tert-butyl.

In one embodiment of the compound of formula II in the present application, $R^5$ is selected from hydrogen or methyl.

In one embodiment of the compound of formula II in the present application, $R^1$ is selected from cyclopropyl, cyclobutyl, cyclopentyl, cyclohexyl, pyrrolidinyl or piperidyl, which may be optionally substituted with one or more groups independently selected from $R^6$.

In one embodiment of the compound of formula II in the present application, $R^1$ is selected from cyclobutyl, cyclopentyl, cyclohexyl, pyrrolidinyl or piperidyl, which may be optionally substituted with one or more groups independently selected from $R^6$; $R^6$ is selected from F, Cl or Br.

In one embodiment of the compound of formula II in the present application, $R^6$ is selected from F, Cl or Br.

In one embodiment of the compound of formula II in the present application, $R^1$ is selected from cyclobutyl or cyclohexyl, which may be optionally substituted with one or two F.

In one embodiment of the compound of formula II in the present application, $R^1$ is selected from

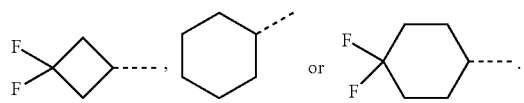

As one preferred specific embodiment of the present application, in the compound represented by formula II or the pharmaceutically acceptable salt, solvate or hydrate thereof, $R^2$ is selected from phenyl, furyl (furanyl), thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl or triazinyl, which may be optionally substituted with one or more groups independently selected from $R^7$; $R^7$ is selected from F, Cl, Br, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl, aminosulfonyl or N-substituted aminosulfonyl. Further, $R^2$ is selected from phenyl or pyridyl, which may be optionally substituted with one or more groups independently selected from $R^7$; $R^7$ is selected from F, cyano, trifluoromethyl, $-SO_2NH_2$ or 4-cyanopyridine-2-aminosulfonyl.

In one embodiment of the compound of formula II in the present application, $R^2$ is selected from phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl or triazinyl, which may be optionally substituted with one or more groups independently selected from $R^7$.

In one embodiment of the compound of formula II in the present application, $R^2$ is selected from phenyl or pyridyl, which may be optionally substituted with one or more groups independently selected from $R^7$.

In one embodiment of the compound of formula II in the present application, $R^7$ is selected from F, Cl, Br, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl, oxo or

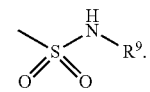

In one embodiment of the compound of formula II in the present application, $R^7$ is selected from F, cyano, trichloromethyl, oxo,

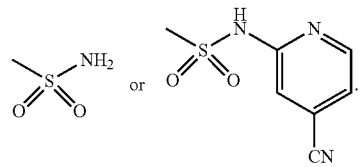

In one embodiment of the compound of formula II in the present application, $R^9$ is selected from H, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl or triazinyl, which may be optionally substituted with one or more groups independently selected from $R^{10}$.

In one embodiment of the compound of formula II in the present application, $R^9$ is selected from pyridyl, which may be optionally substituted with one or more groups independently selected from $R^{10}$.

In one embodiment of the compound of formula II in the present application, $R^{10}$ is selected from cyano.

In one embodiment of the compound of formula II in the present application,

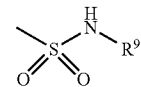

is selected from

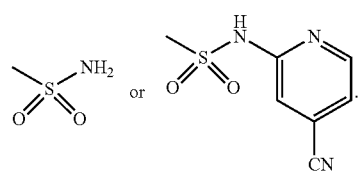

In one embodiment of the compound of formula II in the present application, $R^2$ is selected from

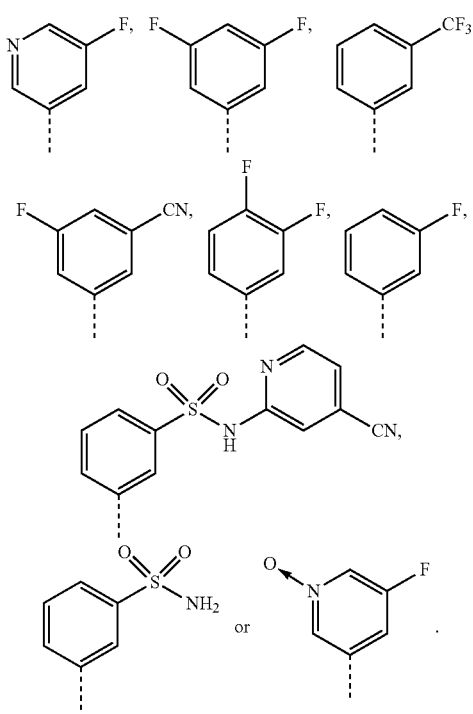

As one preferred specific embodiment of the present invention, in the compound represented by formula II or the pharmaceutically acceptable salt, solvate or hydrate thereof, $R^3$ is selected from phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl, triazinyl, benzyl, furanylmethylene, thienylmethylene, pyrrolylmethylene, pyrazolylmethylene, imidazolylmethylene, pyridylmethylene, pyrimidinylmethylene, pyridazinylmethylene, pyrazinylmethylene, thiazolylmethylene, isothiazolylmethylene, oxazolylmethylene, isoxazolylmethylene, tetrazolylmethylene or triazinylmethylene, which may be optionally substituted with one or more groups independently selected from $R^8$; $R^8$ is selected from hydrogen, F, Cl, Br, cyano, ethynyl, 1-propynyl or 1-butynyl. Further, $R^3$ is selected from pyridyl, pyrimidyl or benzyl, which may be optionally substituted with one or more groups independently selected from $R^8$; $R^8$ is selected from F, cyano or ethynyl.

In one embodiment of the compound of formula II in the present application, $R^3$ is selected from phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl, triazinyl, benzyl, furanylmethylene, thienylmethylene, pyrrolylmethylene, pyrazolylmethylene, imidazolylmethylene, pyridylmethylene, pyrimidinylmethylene, pyridazinylmethylene, pyrazinylmethylene, thiazolylmethylene, isothiazolylmethylene, oxazolylmethylene, isoxazolylmethylene, tetrazolylmethylene or triazinylmethylene, which may be optionally substituted with one or more groups independently selected from $R^8$.

In one embodiment of the compound of formula II in the present application, $R^3$ is selected from pyridyl, pyrimidyl or benzyl, which may be optionally substituted with one or more groups independently selected from $R^8$.

In one embodiment of the compound of formula II in the present application, $R^8$ is selected from F, Cl, Br, cyano, ethynyl, 1-propynyl or 1-butynyl.

In one embodiment of the compound of formula II in the present application, $R^8$ is selected from F, cyano or ethynyl.

In one embodiment of the compound of formula II in the present application, $R^3$ is selected from

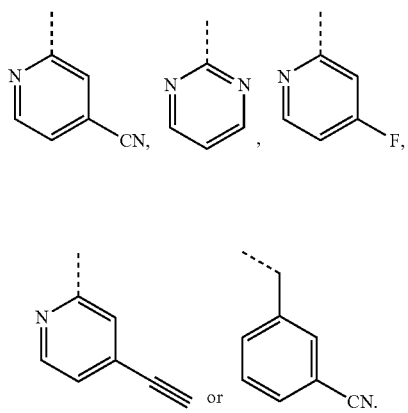

As one embodiment of the present application, a compound represented by formula II-1 or a pharmaceutically acceptable salt, solvate or hydrate thereof is provided:

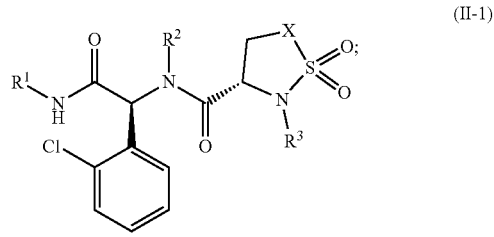

(II-1)

wherein, the substituents are defined as described for the compound of formula II.

As one embodiment of the present application, a compound represented by formula II-2 or a pharmaceutically acceptable salt, solvate or hydrate thereof is provided:

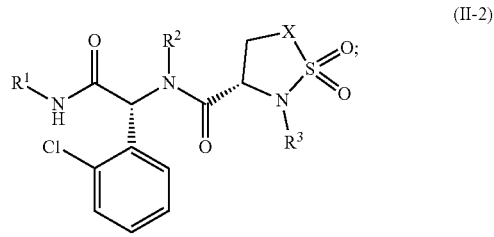

(II-2)

wherein, the substituents are defined as described for the compound of formula II.

The following compounds or the pharmaceutically acceptable salts, solvates or hydrates thereof are preferred in the present application:

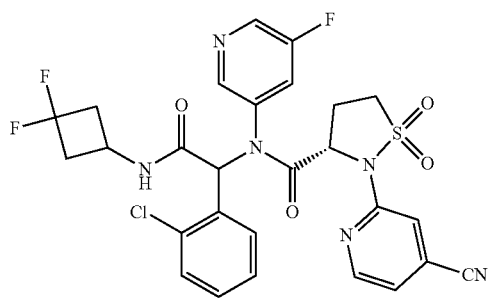
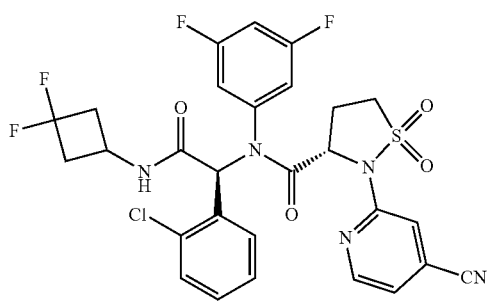
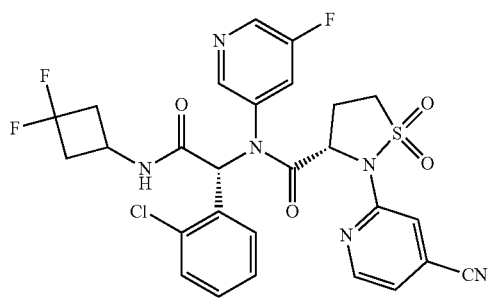
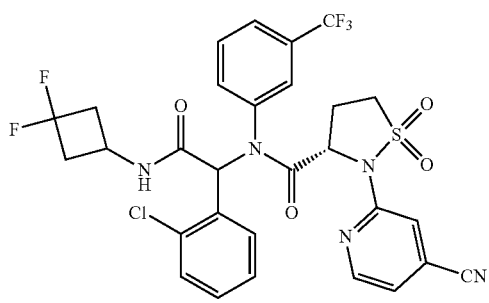
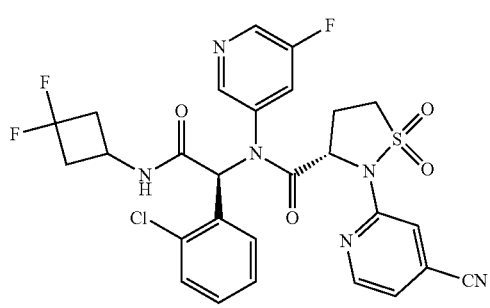
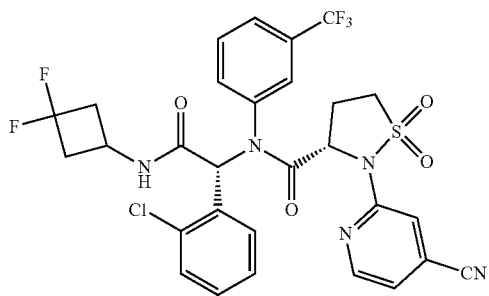
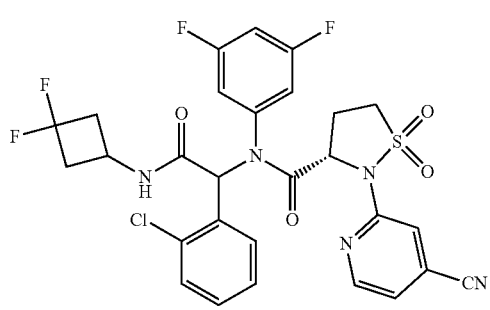
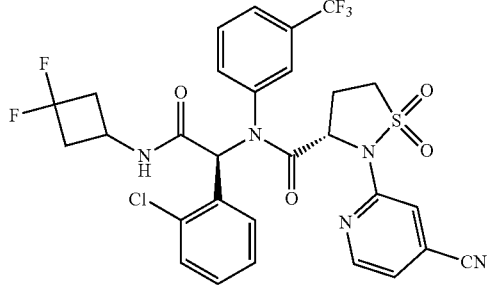
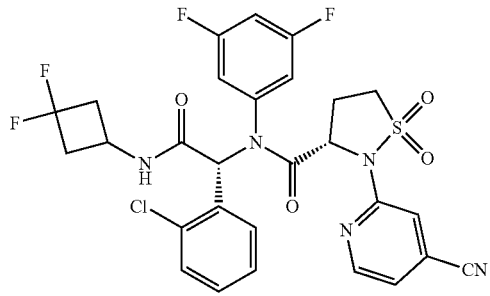
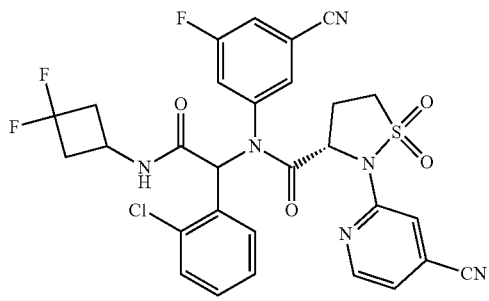

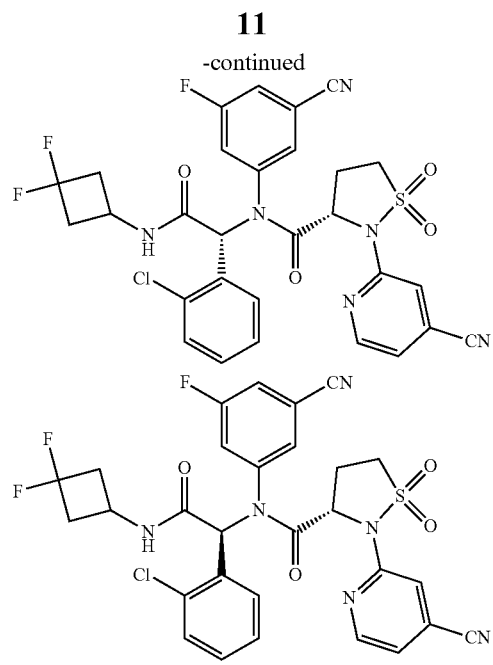
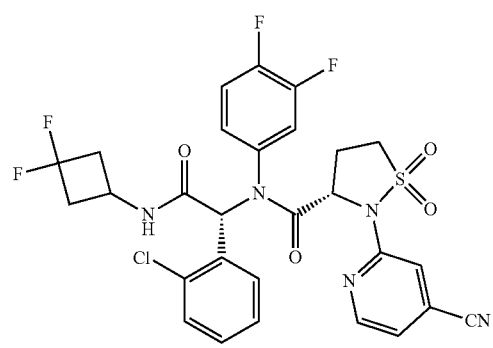
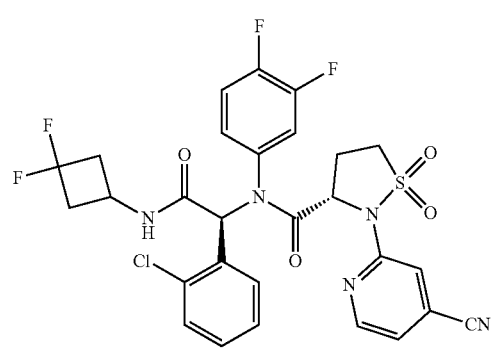
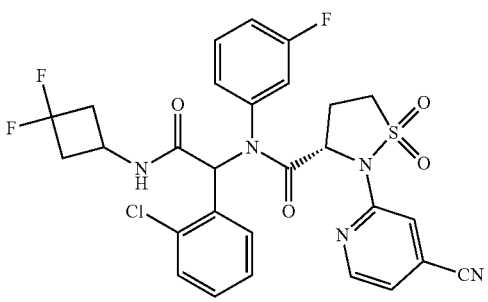
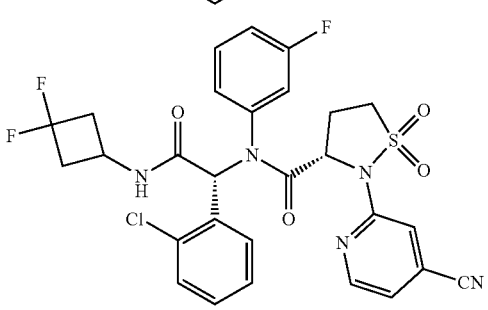
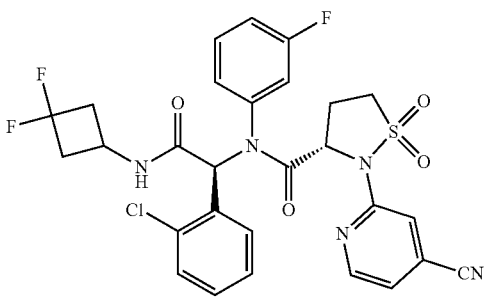
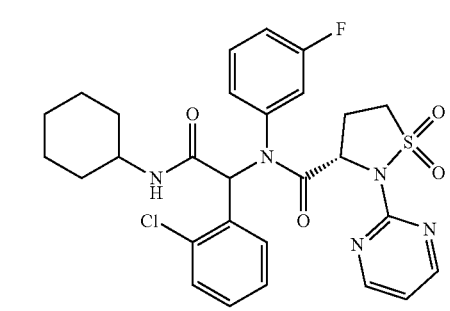
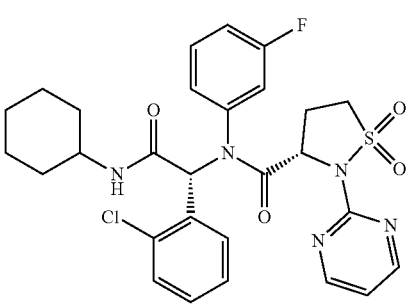

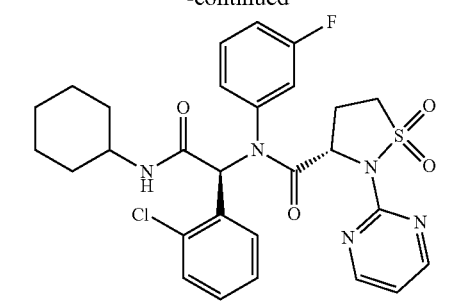
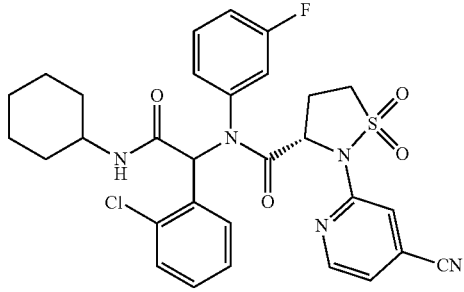
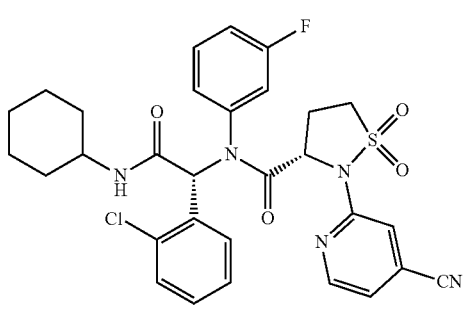
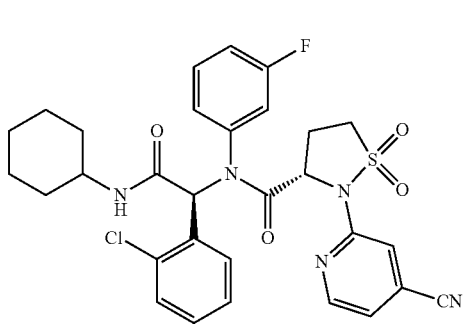
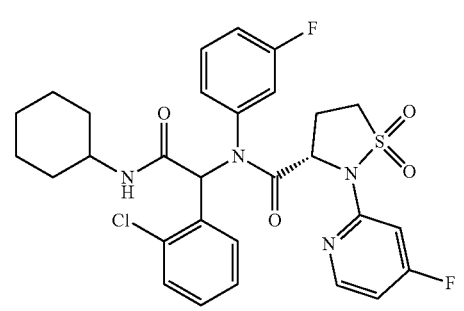
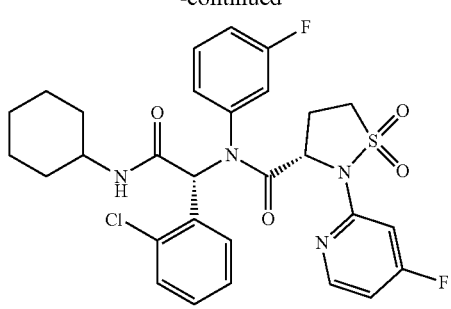
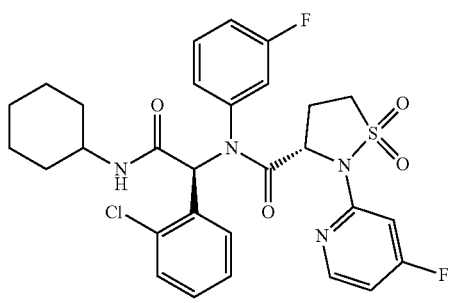
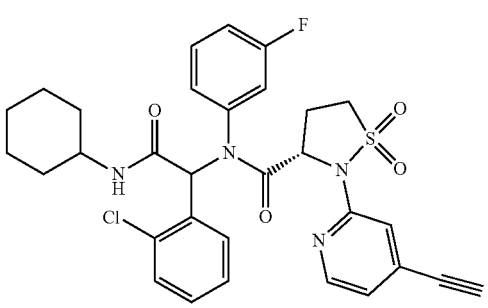
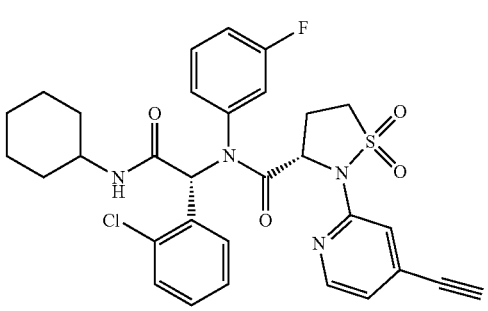
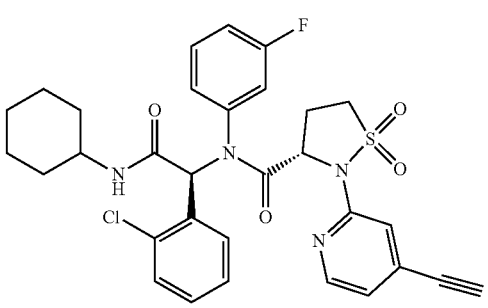

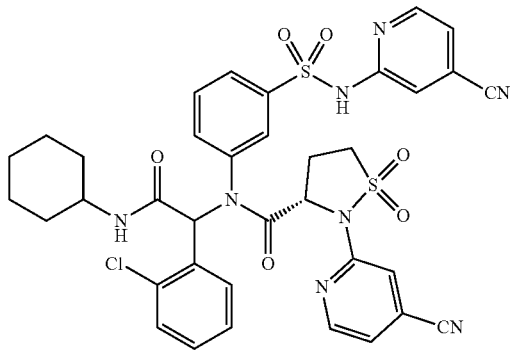
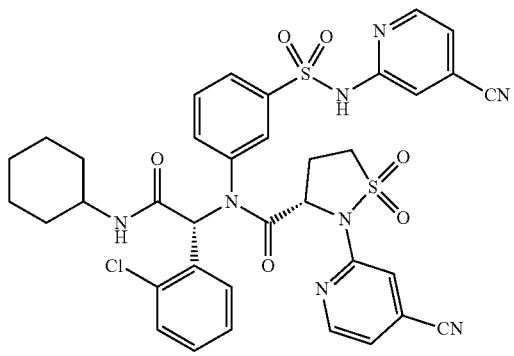
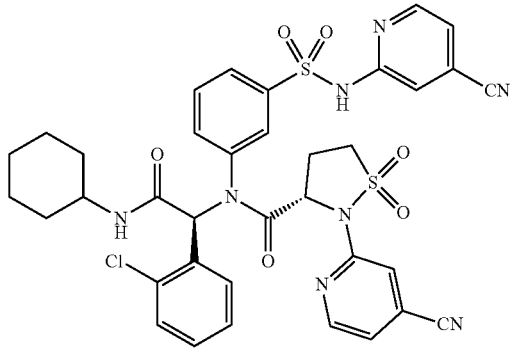
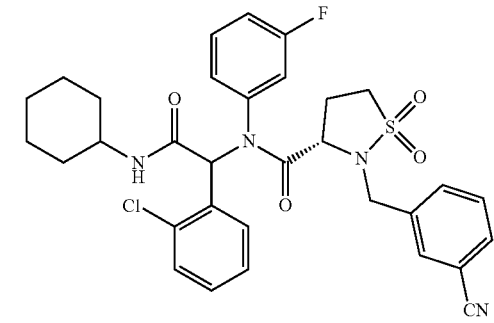
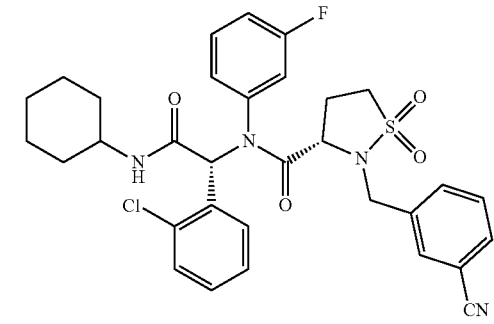
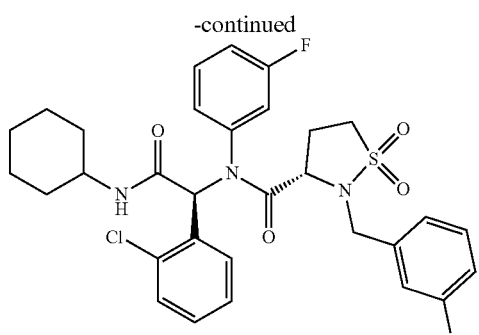
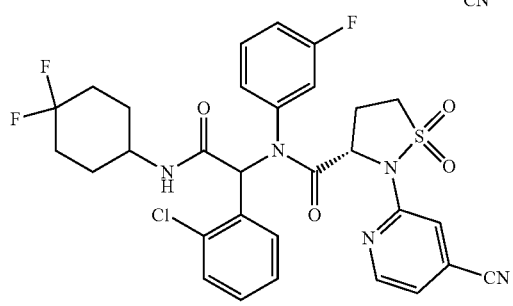
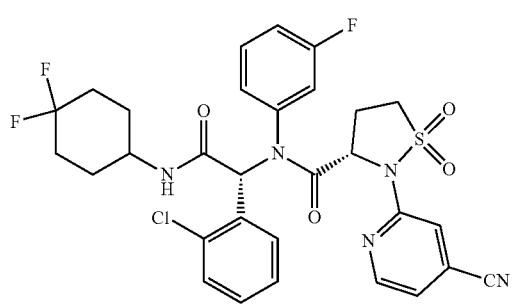
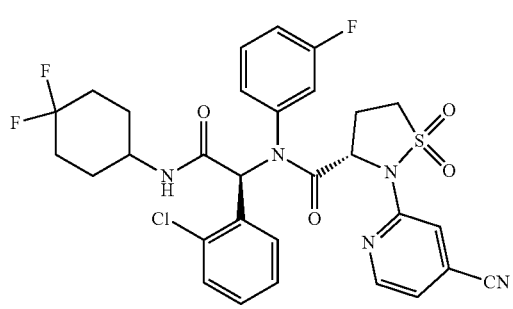
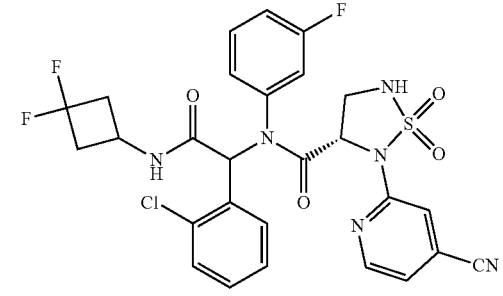

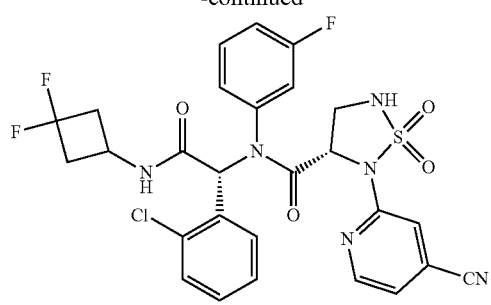
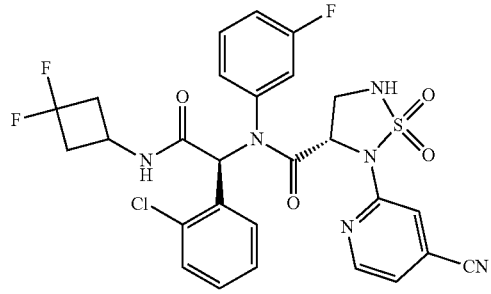
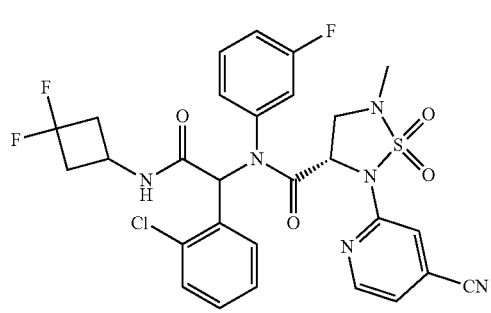
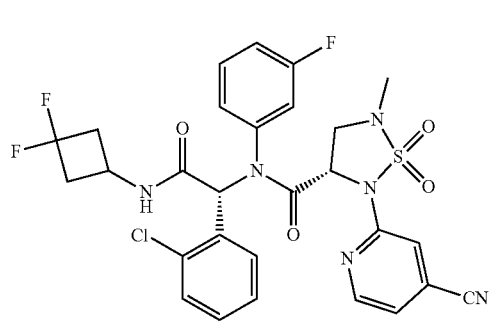
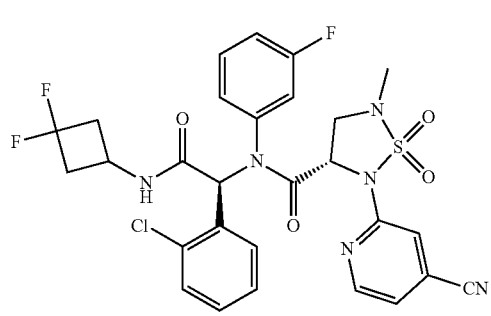
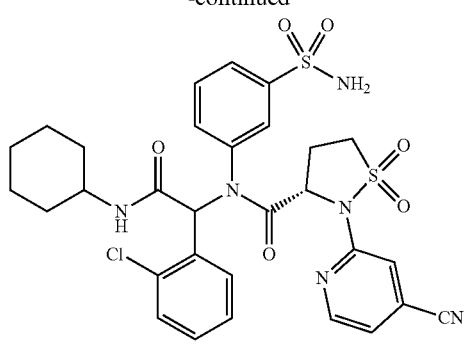
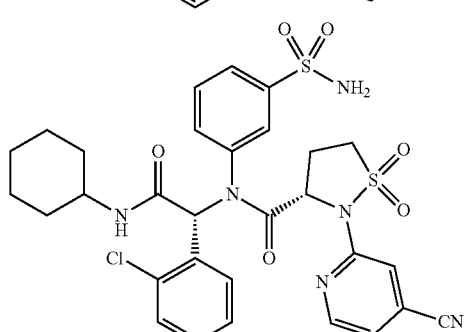
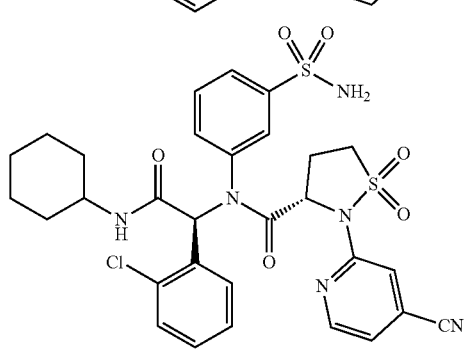
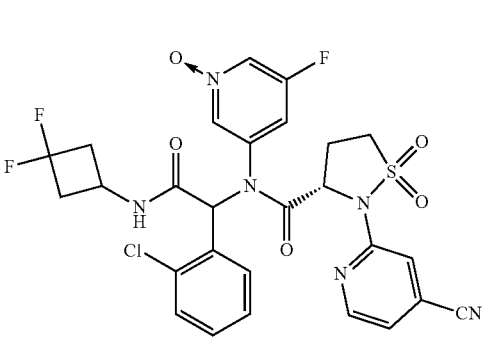
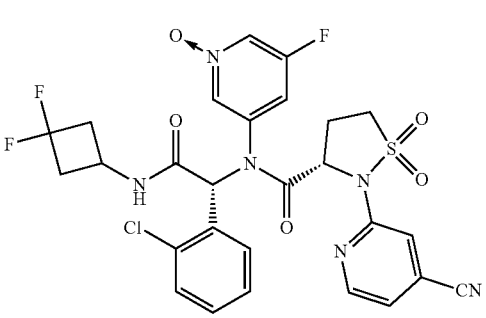

-continued

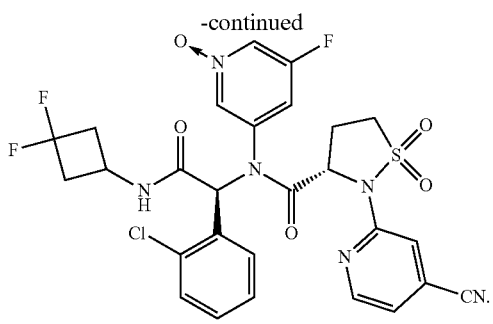

Another aspect of the present application provides a pharmaceutical composition, comprising a therapeutically effective amount of the compound of formula I or the pharmaceutically acceptable salt, solvate or hydrate thereof; and one or more pharmaceutically acceptable carriers or excipients. The pharmaceutical composition of the present application may further contain one or more additional therapeutic agents.

Another aspect of the present application provides a method for treating IDH1 mutation-induced cancers, wherein the IDH1 mutation has R132X mutation. In some embodiments, R132X mutation is selected from R132H, R132C, R132L, R132V, R132S and R132G. In some preferred embodiments, R132X mutation is selected from R132H and R132C. The method comprises administering a therapeutically effective amount of the compound of formula I or II or the pharmaceutically acceptable salt, solvate or hydrate thereof, or the pharmaceutical composition thereof to patients in need thereof.

Another aspect of the present application provides use of the compound of formula I or the pharmaceutically acceptable salt, solvate or hydrate thereof, or the pharmaceutical composition including the same in manufacture of a medicament for treating IDH1 mutation-induced cancers.

Another aspect of the present application provides the compound of formula I or the pharmaceutically acceptable salt, solvate or hydrate thereof, or the pharmaceutical composition including the same for treating IDH1 mutation-induced cancers.

In some embodiments of the present application, the IDH1 mutation-induced cancers are selected from: glioblastoma (neuroglioma), myelodysplastic syndrome (MDS), myeloproliferative neoplasm (MPN), acute myelogenous leukemia (AML), sarcoma (preferably chondrosarcoma, fibrosarcoma), melanoma, non-small cell lung cancer, bile duct cancer or angioimmunoblastic non-Hodgkin's lymphoma (NHL). In more specific embodiments, the cancers to be treated are neuroglioma, myelodysplastic syndrome (MDS), myeloproliferative neoplasm (MPN), acute myelogenous leukemia (AML), bile duct cancer, chondrosarcoma, or angioimmunoblastic non-Hodgkin's lymphoma (NHL), etc., preferably including acute myelogenous leukemia (AML), myelodysplastic syndrome (MDS), neuroglioma, bile duct cancer or chondrosarcoma.

The compound represented by formula I or the pharmaceutically acceptable salt, solvate or hydrate thereof provided herein shows very good inhibitory activity against IDH1, which is comparable or superior to the activity of AG-120, and has a very good metabolism level in vivo and a very long half-life in vivo, and is promising to become a drug more suitable for the treatment of IDH1 mutation-induced cancers.

The pharmaceutical composition of the present application can be prepared by combining a compound of the present application or a pharmaceutically acceptable salt, solvate or hydrate thereof with suitable pharmaceutically acceptable carriers. For example, it can be formulated into solid, semi-solid, liquid or gaseous preparations, such as tablets, pills, capsules, powders, granules, ointments, emulsions, suspensions, solutions, suppositories, injections, inhalants, gels, microspheres, and aerosols, and the like.

Typical administration routes of compounds of the present application or pharmaceutically acceptable salts, solvates or hydrates thereof, or pharmaceutical compositions including the same include, but are not limited to, oral, rectal, transmucosal, intestinal administration, or topical, transdermal, inhalation, parenteral, sublingual, intravaginal, intranasal, intraocular, intraperitoneal, intramuscular, subcutaneous, intravenous administration.

The pharmaceutical composition of the present application may be manufactured by methods well-known in the art, such as conventional mixing method, dissolution method, granulation method, method for preparing sugar-coated pills, grinding method, emulsification method, freeze-drying method and the like.

For oral administration, the pharmaceutical composition can be formulated by mixing an active compound with a pharmaceutically acceptable carrier well-known in the art. These carriers can allow the compounds of the present application to be formulated into tablets, pills, troches, dragees, capsules, liquids, gels, slurries, suspensions and the like, for oral administration to patients.

A solid oral composition can be prepared by conventional mixing, filling or tableting method. For example, it can be obtained by the following method: mixing the active compound with solid excipients, optionally milling the resultant mixture, adding other suitable adjuvants if necessary, and then processing the mixture into granules, to produce tablet cores or dragee cores. Suitable adjuvants include, but are not limited to, adhesives, diluents, disintegrants, lubricants, glidants, sweeteners, flavoring agents or the like. The adjuvants can be, such as, microcrystalline cellulose, glucose solution, acacia mucilage, gelatin solution, sucrose and starch paste; talc, starch, magnesium stearate, calcium stearate or stearic acid; lactose, sucrose, starch, mannitol, sorbitol or dicalcium phosphate; silicon dioxide; croscarmellose sodium, pregelatinized starch, sodium starch glycolate, alginic acid, corn starch, potato starch, methylcellulose, agar, carboxymethyl cellulose, crosslinked polyvinylpyrrolidone and the like. The dragee core can be optionally coated, especially with an enteric coating, according to methods recognized in common drug practice.

The pharmaceutical composition can also be suitable for parenteral administration, such as sterile solutions, suspensions or freeze-dried products in a suitable unit dosage form. An appropriate excipient such as a filler, a buffering agent, or surfactant can be used.

The compound represented by formula I or the pharmaceutically acceptable salt, solvate or hydrate thereof described herein can be administered by any suitable routes and methods, for example orally or parenterally (e.g., intravenously) administered. The therapeutically effective amount of the compound of formula I or II ranges from about 0.0001 mg/Kg of body weight to 20 mg/Kg of body weight per day, for example from 0.001 mg/Kg of body weight to 10 mg/Kg of body weight per day.

The dosing frequency of the compound of formula I depends on needs of individual patients, for example, once or twice every day or more times every day. Administration can be intermittent, for example, during a period of several days, patients receive a daily dose of the compound of formula I or II, and during a period of next several or more days, they do not receive a daily dose of the compound of formula I or II.

Related Definitions

Unless otherwise indicated, the following terms and phrases used herein are intended to have the following meanings. A particular term or phrase should not be considered to be indefinite or unclear in the absence of a specific definition, but should be interpreted as its ordinary meanings. When a trade name appears herein, it is intended to refer to the corresponding commodity or active ingredient thereof.

The term "optional" or "optionally" means that the subsequently described event or situation may occur or not, and the description includes the event or situation occurs and not. For example, an ethyl is "optionally" substituted by a halogen, meaning that the ethyl may be unsubstituted ($CH_2CH_3$), monosubstituted (e.g., $CH_2CH_2F$), polysubstituted (e.g., $CHFCH_2F$, $CH_2CHF_2$, etc.) or completely substituted ($CF_2CF_3$). It can be understood by the skilled in the art that, for any groups containing one or more substituents, any substitutions or substitution patterns that are unable to exist spatially and/or cannot be synthesized will not be introduced.

The $C_{m-n}$ used herein means that this moiety has m-n carbon atoms. For example, "$C_{3-10}$ cycloalkyl" means that said cycloalkyl has 3 to 10 carbon atoms. "$C_{0-6}$ alkylene" means that said alkylene has 0 to 6 carbon atoms, and the alkylene is a bond when this group has 0 carbon atom.

A numerical range herein refers to each integer within a given range. For example, "$C_{1-10}$" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms or 10 carbon atoms.

The term "substituted" means that any one or more of the hydrogen atoms on a specific atom are substituted by a substituent, or means that when a specific atom donates or accepts an electron pair and forms a coordinate bond with another atom, the specific atom is deemed to be substituted by another atom, as long as the valence state of the specific atom is normal and the substituted compound is stable. When the substituent is a ketone group (i.e., =O), it means that two hydrogen atoms are substituted, and the keto-substitution will not occur on an aromatic group.

When any variable (e.g., R) appears more than once in composition or structure of a compound, its definition in each case is independent. Thus, for example, if a group is substituted by 0-2 R, this group may be optionally substituted by at most two R, and R in each case has independent options. Furthermore, the combination of substituents and/or variants thereof is allowed only if such combination results in stable compounds.

Unless otherwise specified, the term "hetero" means a heteroatom or a heteroatom group (i.e., a group containing a heteroatom), i.e., atoms except for carbon and hydrogen atoms or an atom group containing such atoms. A heteroatom is independently selected from oxygen, nitrogen, sulfur, phosphorus, silicon, germanium, aluminum and boron. In an embodiment where two or more heteroatoms are involved, the two or more heteroatoms may be identical, or parts or all of the two or more heteroatoms may be different.

The term "halogen" or "halo/halogenated" refers to any group of fluorine, chlorine, bromine or iodine.

The term "hydroxyl" refers to —OH.

The term "cyano" refers to —CN.

The term "amino" refers to —$NH_2$, —NH(alkyl) and —N(alkyl)$_2$, and specific examples of an amino include, but are not limited to, —$NH_2$, —$NHCH_3$, —$NHCH(CH_3)_2$, —$N(CH_3)_2$, —$NHC_2H_5$, —$N(CH_3)C_2H_5$ and the like.

The term "oxo" means that the substituent on the C atom is a ketone group (i.e., =O) or the substituent on the N atom is O (i.e., N→O).

The term "alkyl" refers to a straight or branched saturated aliphatic hydrocarbon group consisting of carbon atoms and hydrogen atoms, such as, methyl, ethyl, propyl, butyl, pentyl, hexyl, heptyl, octyl, nonyl, decyl and the like. The specific alkyl includes all isomers thereof. For example, propyl includes —$CH_2CH_2CH_3$ and —$CH(CH_3)_2$. For example, butyl includes —$CH_2CH_2CH_2CH_3$, —$CH(CH_3)(CH_2CH_3)$, —$C(CH_3)_3$ and —$CH_2CH(CH_3)_2$. The term "$C_{1-6}$ alkyl" refers to an alkyl having 1 to 6 carbon atoms. The term "$C_{1-4}$ alkyl" refers to an alkyl having 1 to 4 carbon atoms. The term "$C_{1-3}$ alkyl" refers to an alkyl having 1 to 3 carbon atoms. The "alkyl", "$C_{1-8}$ alkyl", "$C_{1-6}$ alkyl" or "$C_{1-3}$ alkyl" may be unsubstituted or substituted with one or more substituents selected from hydroxyl, halogen or amino.

The term "haloalkyl/halogenated alkyl" intends to include monohaloalkyl and polyhaloalkyl. For example, the term "$C_{1-3}$ haloalkyl" intends to include, but is not limited to, trifluoromethyl, 2,2,2-trifluoroethyl, 3-bromopropyl and the like. Examples of the haloalkyl include, but are not limited to, trifluoromethyl, trichloromethyl, pentafluoroethyl and pentachloroethyl.

The term "alkenyl" refers to a straight or branched hydrocarbon chain containing 2 to 12 carbon atoms and having one or more double bonds. Examples of the alkenyl include, but are not limited to, allyl, propenyl, 2-butenyl and 3-hexenyl. One of the double-bonded carbon atoms may be optionally an attachment site of an alkenyl substituent.

The term "alkynyl" refers to a straight or branched hydrocarbon chain containing 2 to 12 carbon atoms and characterized by having one or more triple bonds. Examples of the alkynyl include, but are not limited to, ethynyl, propynyl, propargyl and 3-hexynyl. One of the triple-bonded carbon atoms may be optionally an attachment site of an alkynyl substituent.

The term "cycloalkyl" refers to an all-carbon monocyclic saturated hydrocarbon group consisting of carbon atoms and hydrogen atoms, such as, $C_{3-20}$ cycloalkyl, preferably $C_{3-6}$ cycloalkyl such as cyclopropyl, cyclobutyl, cyclopentyl, cyclohexyl and the like. The cycloalkyl may be unsubstituted or substituted, and the substituent includes, but is not limited to, alkyl, alkoxy, cyano, carboxyl, aryl, heteroaryl, amino, halogen, sulfonyl, sulfinyl, phosphoryl and hydroxyl.

The term "aryl" refers to an all-carbon monocyclic or polycyclic fused aromatic ring group having a conjugated π-electron system, preferably having 6 to 14 carbon atoms, more preferably 6 to 12 carbon atoms, and most preferably 6 carbon atoms. For example, a monocyclic aromatic ring group is selected from such as phenyl; a bicyclic fused aromatic ring group consists of phenyl fused to a 4- to 6-membered aromatic or non-aromatic carbocyclic ring, including naphthyl.

The term "heteroaromatic ring" refers to a single or fused ring having 5 to 12 ring atoms, such as, 5, 6, 7, 8, 9, 10, 11 or 12 ring atoms, wherein 1, 2, 3 or 4 ring atoms are selected from N, O and S, and the rest of ring atom(s) is(are) carbon atom(s), and the ring has a completely conjugated π-electron system.

The term "heteroaryl" refers to a residue after one hydrogen atom is removed from a "heteroaramatic ring" molecule. The heteroaryl may be unsubstituted or substituted, and the substituent includes, but is not limited to, alkyl, alkoxy, aryl, aralkyl, amino, halogen, hydroxyl, cyano, nitro, carbonyl and heteroalcyl. Non-limiting examples of unsubstituted heteroaryl include, but are not limited to, pyrrolyl, furyl, thienyl, imidazolyl, oxazolyl, pyrazolyl, pyridyl, pyrimidyl, pyrazinyl, quinolyl, isoquinolyl, tetrazolyl, triazinyl.

The term "heteroalicyclic ring" refers to a single or fused ring having 3-12 ring atoms, for example, 3, 4, 5, 6, 7, 8, 9, 10, 11 or 12 ring atoms, in which 1 or 2 ring atoms are heteroatoms selected from N, O, S and $S(O)_n$ (wherein n is 0, 1 or 2), and the rest of ring atom(s) is(are) C. Such ring may be saturated or unsaturated (e.g., having one or more double bonds), but it does not have a completely conjugated π-electron system. Examples of 3-membered saturated heteroalicyclic ring include, but are not limited to,

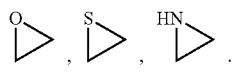

Examples of 4-membered saturated heteroalicyclic ring include, but are not limited to,

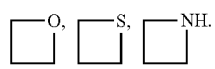

Examples of 5-membered saturated heteroalicyclic ring include, but are not limited to,

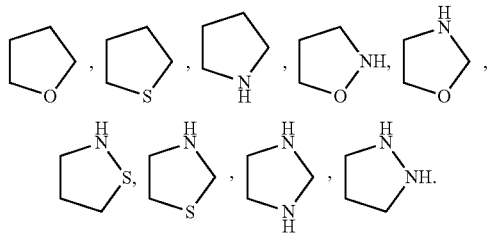

Examples of 6-membered saturated heteroalicyclic ring include, but are not limited to,

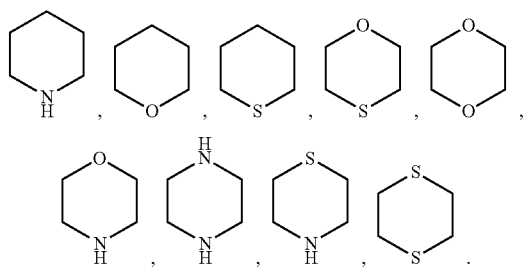

Examples of 7-membered saturated heteroalicyclic ring include, but are not limited to,

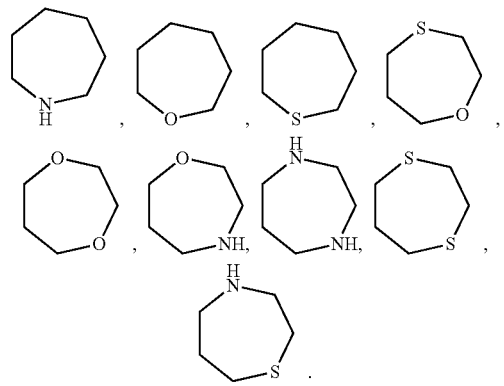

Examples of 5-membered unsaturated heteroalicyclic ring include, but are not limited to,

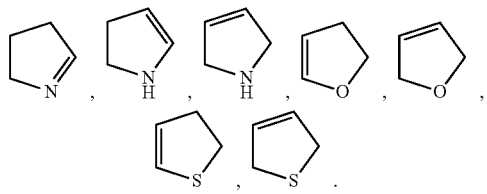

Examples of 6-membered unsaturated heteroalicyclic ring include, but are not limited to,

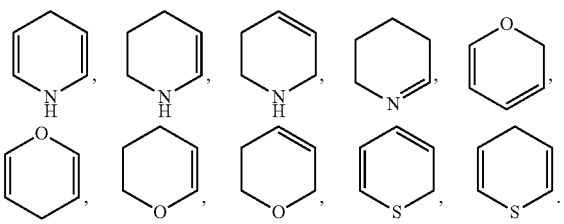

The term "heterocycloalkyl" refers to a residue after one hydrogen atom is removed from a "heteroalicyclic ring" molecule. The heterocycloalkyl may be unsubstituted or the hydrogen atom therein is optionally substituted with a substituent, and the substituent includes, but is not limited to, alkyl, alkoxy, =O, aryl, aralkyl, —COOH, —CN, amino, halogen or hydroxyl.

"DMF" refers to N,N-dimethylformamide.
"DIAD" refers to diisopropyl azodicarboxylate.
"Boc-" refers to tert-butoxycarbonyl.
"TFA" refers to trifluoroacetic acid.
"DCM" refers to dichloromethane.
"PE" refers to petroleum ether.
"EA" refers to ethyl acetate.
"DCM" refers to dichloromethane.
"0.5% MC" refers to 0.5% methylcellulose contained in the formulation of preparations.
"0.2% Tween 80" refers to 0.2% polyoxyethylene sorbitan monooleate 80 contained in the formulation of preparations.
"$Pd_2(dba)_3$" refers to tris(dibenzylideneacetone) dipalladium.
"Xantphos" refers to 4,5-bis(diphenylphosphino)-9,9-dimethylxanthene.

The term "Ugi reaction" refers to a multi-component reaction in which a molecule of a ketone or aldehyde, a molecule of an amine, a molecule of an isonitrile and a molecule of a carboxylic acid are condensed to produce an α-amidoamide.

The term "Goldberg coupling reaction" refers to a reaction in which C atom of an aryl group forms a bond with N, O or C atom catalyzed by copper.

The term "Mitsunobu reaction" refers to a reaction in which alcoholic hydroxyl is substituted with a nucleophilic agent under the action of diethyl azodicarboxylate (DEAD) and triphenylphosphine, and at the same time the carbon atom linked to the hydroxyl group occurs an inversion of configuration; wherein the nucleophilic agent is a donor of electron pair (i.e., lewis base).

The term "pharmaceutically acceptable" refers to the following compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As a pharmaceutically acceptable salt, for example, a metal salt, an ammonium salt, a salt formed with organic base, a salt formed with inorganic acid, a salt formed with organic acid, a salt formed with basic or acidic amino acid, etc. can be mentioned.

The pharmaceutically acceptable salt of the present application can be synthesized from a parent compound containing an acid radical or basic group via conventional chemical methods. In general, such a salt is prepared by a method of allowing these compounds in the form of free acid or base to react with a stoichiometric amount of an appropriate base or acid in water or an organic solvent or a mixture thereof. Generally, a non-aqueous medium, such as, ether, ethyl acetate, ethanol, isopropanol or acetonitrile, and the like, is preferable.

Certain compounds of the present application may exist in a non-solvated or solvated form, including a hydrate form. In general, the solvated form is equivalent to the non-solvated form, both of which are encompassed within the scope of the present application. Certain compounds of the present application may exist in a polymorphic or amorphous form.

Certain compounds of the present application may have an asymmetric carbon atom (optical center) or a double bond. Racemates, diastereomers, geometric isomers and individual isomers are all encompassed within the scope of the present application.

The graphic representations of racemic, ambiscalemic and scalemic, or enantiomerically pure compounds herein are from Maehr, *J. Chem. Ed.* 1985, 62: 114-120. Unless otherwise stated, the absolute configuration of a stereocenter is represented by solid and broken wedges. When the compounds described herein contain olefinic double bonds or other geometric asymmetrical centers, unless otherwise specified, they include E, Z geometric isomers. Likewise, all tautomeric forms are included within the scope of the present invention.

The compound of the present application may exist in specific geometric or stereoisomeric forms. All such compounds envisaged by the present application include cis and trans isomers, (−)- and (+)-enantiomers, (R)- and (S)-enantiomers, diastereomers, (D)-isomers, (L)-isomers, and racemic mixtures and other mixtures thereof, such as enantiomers or diastereomers enriched mixtures, all of which fall within the scope of the present application. Other asymmetric carbon atoms may be present in the substituents such as alkyl. All these isomers and their mixtures are included in the scope of the present application.

The optically active (R)- and (S)-isomers as well as the D and L isomers can be prepared by chiral synthesis or chiral reagents or other conventional techniques. If an enantiomer of a certain compound of the present invention is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by a fractional crystallization or chromatography well-known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compound of the present application may contain non-natural proportions of atomic isotopes on one or more atoms which constitute the compound. For example, the compound may be labeled with a radioisotope, such as tritium ($^3$H), iodine-125 ($^{125}$I) or C-14 ($^{14}$C). Any isotopic composition transformations of the compound of the present application, whether are radioactive or not, are included in the scope of the present application.

The term "pharmaceutically acceptable carrier" refers to a carrier that does not cause significant irritation to an organism ingesting this carrier, and does not deteriorate the biological activity and properties of the active compound. The "pharmaceutically acceptable carrier" refers to an inert material that is administered together with an active ingredient and facilitates the administration of the active ingredient, including but not limited to, any glidants, sweeteners, diluents, preservatives, dyes/coloring agents, flavor enhancers, surfactants, wetting agents, dispersants, disintegrants, suspending agents, stabilizers, isotonic agents, solvent or emulsifier, which are acceptable for human or animal (e.g., livestock) and approved by the China Food and Drug Administration. Non-limited examples of the carriers include calcium carbonate, calcium phosphate, various carbohydrates and various kinds of starches, cellulose derivatives, gelatin, vegetable oils, polyethylene glycol and the like. Other information about carriers can refer to Remington: The Science and Practice of Pharmacy, 21$^{st}$ Ed., Lippincott, Williams & Wilkins (2005), the contents of which are incorporated herein by reference.

The term "excipient" generally refers to the carrier, diluent and/or medium which is required to formulate an effective pharmaceutical composition.

For drugs or pharmacologically active agents, the term "effective amount" or "therapeutically effective amount" refers to a sufficient amount of a drug or agent that is non-toxic but can achieve the desired effect. For the oral dosage form of the present application, the "effective amount" of one active substance in the composition means the amount needed to achieve the desired effect when used in combination with another active substance in the composition. The determination of the effective amount varies with each individual, depending on the age and general condition of the subject, as well as the specific active substance. The appropriate effective amount in each case can be determined by the skilled in the art according to a routine experiment.

The term "active ingredient", "therapeutic agent", "active substance" or "active agent" refers to a chemical entity that can effectively treat target disorders, diseases or conditions.

The compound of the present application can be prepared by a variety of synthetic methods well known by the skilled in the art, including the following exemplified embodiments, the embodiments formed by combining them with other chemical synthesis methods, and equivalent alternatives known to the skilled in the art. Preferred embodiments include, but are not limited to the examples of the present application.

The chemical reactions in the specific embodiments of the present application are completed in appropriate solvents, which should be suitable for the chemical changes of the present application as well as the required reagents and materials thereof. In order to obtain the compounds of the present application, sometimes the person skilled in the art needs to make modifications or alternatives to synthetic steps or reaction processes on the basis of existing embodiments.

The compound of formula II in the present application may be prepared by a person skilled in the organic synthesis field by using a standard method in the art through the following route:

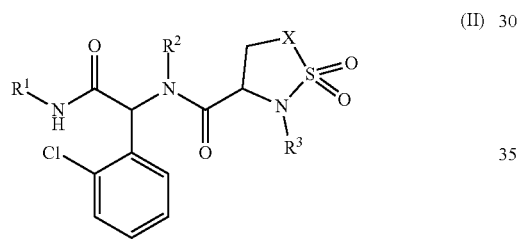

wherein, the definitions of X, $R^1$, $R^2$ and $R^3$ are identical to the above definitions about the compound of formula II.

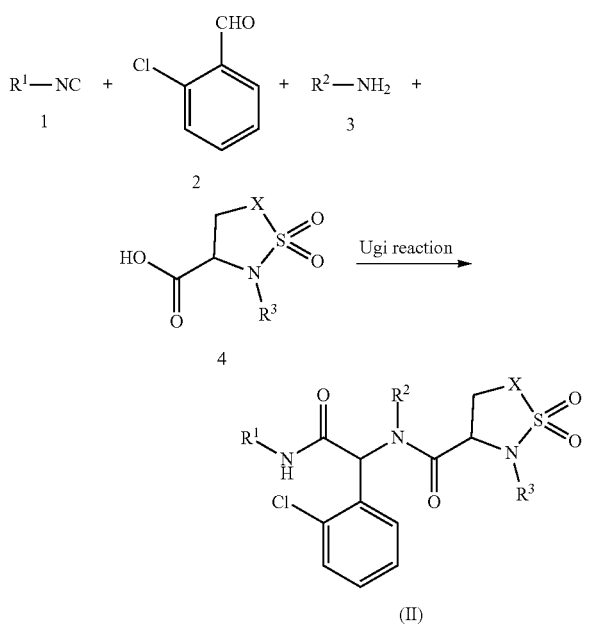

Isonitrile compound 1, o-chlorobenzaldehyde 2, amino compound 3 and sultam carboxylic acid 4 directly undergo Ugi reaction in a suitable solvent (such as methanol and the like), so as to give a compound of formula II.

The compound of formula II in the present application may also be prepared by a person skilled in the organic synthesis field by using a standard method in the art through the following route:

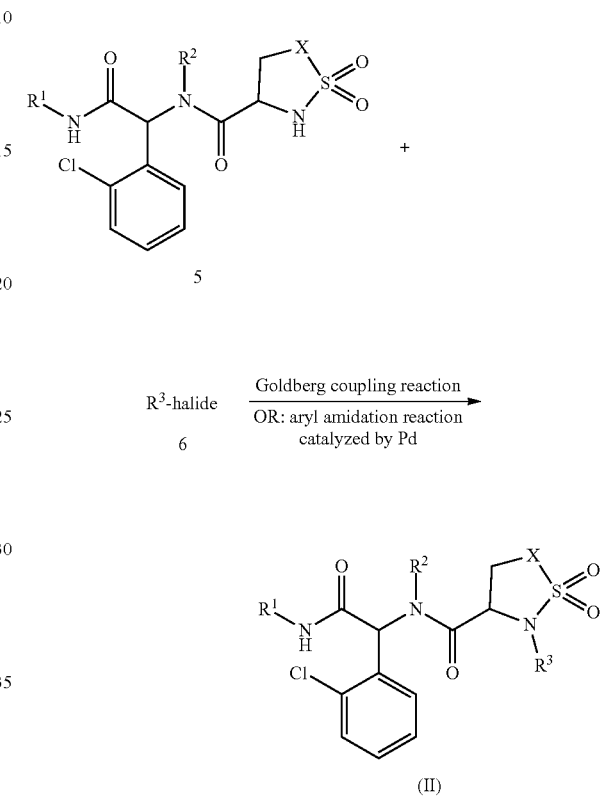

When $R^3$ is H, compound 5 may be obtained by the aforementioned Ugi reaction. Compound 5 is reacted with halogenated compound 6 by Goldberg coupling reaction to give a compound of formula II under the following reaction condition: a suitable copper salt (such as CuI and the like) is used as catalyst, an appropriate ligand (such as N,N'-dimethylethylenediamine and the like) and an alkali (such as cesium carbonate and the like) are added thereto, and they are heated to react in a suitable solvent (such as 1,4-dioxane and the like). Compound 5 may also be reacted with halogenated compound 6 by Pd-catalyzed aryl amidation reaction to give a compound of formula II under the following reaction condition: a suitable palladium (such as $Pd_2(dba)_3$) is used as catalyst, an appropriate ligand (such as Xantphos and the like) and an alkali (such as cesium carbonate and the like) are added thereto, and they are heated to react in a suitable solvent (such as 1,4-dioxane and the like).

The intermediates 1-6 and 1-7 of the present application may be prepared by a person skilled in the organic synthesis field via using a standard method in the art through the following route:

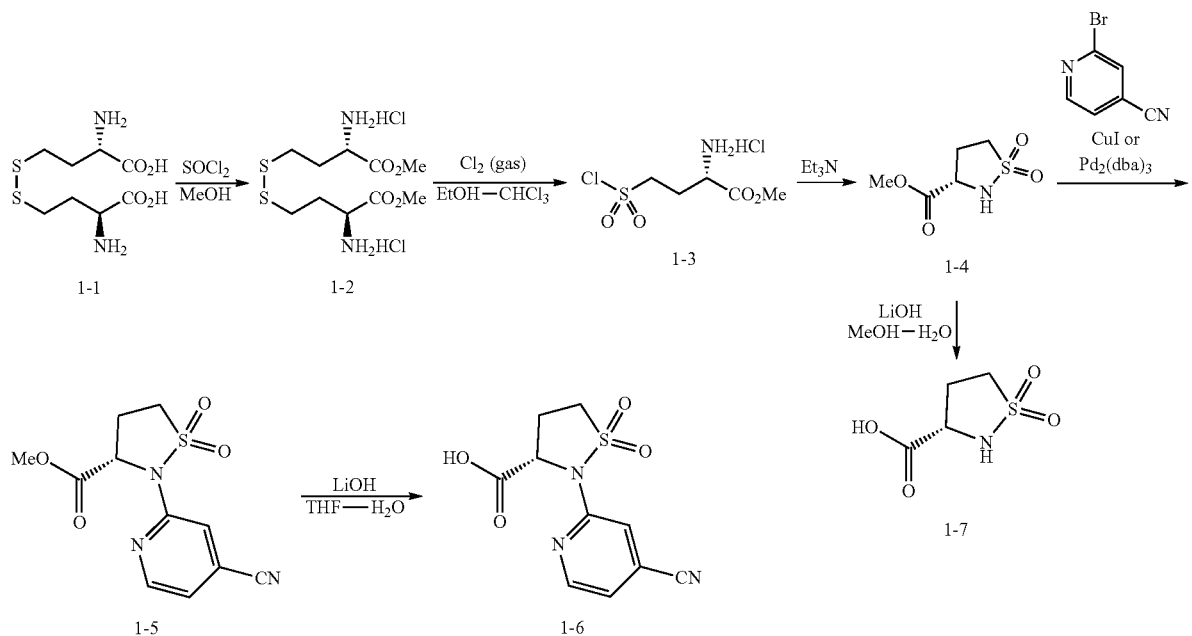

In methanol solution, L-homocysteine 1-1 is reacted with thionyl chloride to give dimethyl L-homocysteinate dihydrochloride 1-2; chlorine gas is flowed into 1-2 to give methyl (S)-2-amino-4-chlorosulfonylbutanoate hydrochloride 1-3; 1-3 is formed a ring under the action of triethylamine to give methyl (S)-isothiazolidine-3-carboxylate 1,1-dioxide 1-4; 1-4 is hydrolyzed to give intermediate (S)-isothiazolidine-3-carboxylic acid 1,1-dioxide 1-7. 1-4 is coupled with 2-bromo-4-cyanopyridine, which is catalyzed by CuI or Pd$_2$(dba)$_3$, to give compound 1-5; 1-5 is hydrolyzed to give intermediate 1-6.

Intermediates 2-6 and 2-10 of the present application may be prepared by a person skilled in the organic synthesis field via using a standard method in the art through the following route:

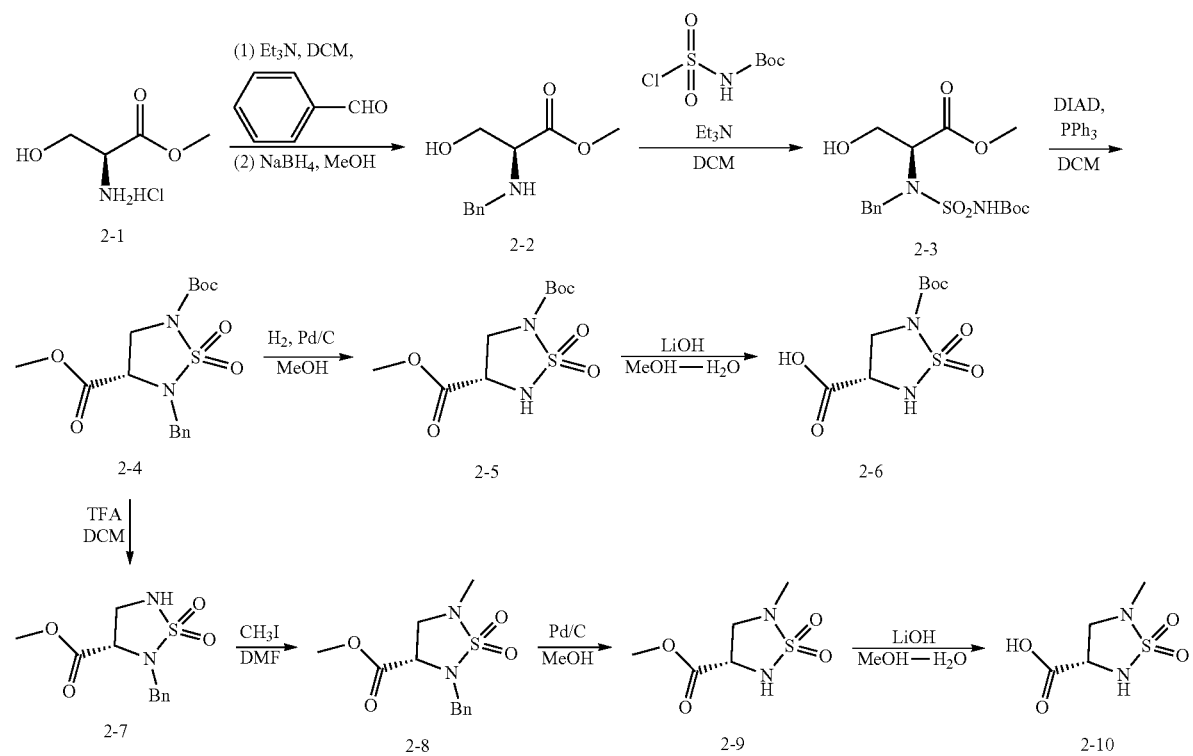

L-serine methyl ester hydrochloride 2-1 undergoes reductive amination reaction to give benzyl-protected compound 2-2; 2-2 is sulfonylated to give compound 2-3; 2-3 undergoes intramolecular cyclization via Mistunbu reaction, to give compound 2-4; 2-4 is debenzylated by hydrogenation to give compound 2-5; 2-5 undergoes hydrolysis to give intermediate 2-6. The Boc protecting group is removed from 2-4 to give compound 2-7; 2-7 takes place N-methylation reaction to give compound 2-8; 2-8 is debenzylated by hydrogenation to give compound 2-9; 2-9 is hydrolyzed to give intermediate 2-10.

DETAILED DESCRIPTION

Figure 1:
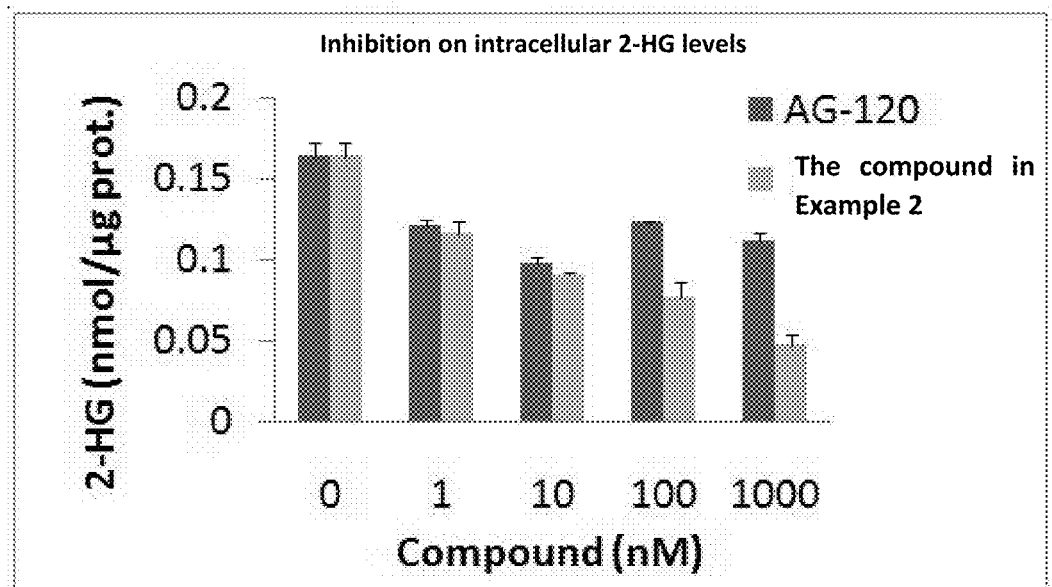
FIG. 1 shows the inhibitory results of the compound in Example 2 and control AG-120 directed to 2-HG in IDH1-mutated HT-1080 cells.

The following specific examples are provided to enable those skilled in the art to more clearly understand and practice the application. They should not be deemed as limiting the scope of the application, but are merely illustrations and typical representatives of the application. Those skilled in the art should understand that there are other synthetic routes for preparing the compounds of the present application, and ones provided below are non-limiting examples.

Unless otherwise stated, the temperature is Celsius temperature. The reagents were purchased from commercial suppliers such as Sinopharm Chemical Reagent Beijing Co., Ltd., Alfa Aesar, or Beijing J&K Scientific Co., Ltd., and the like, and these reagents can be directly used without further purification, unless otherwise stated.

Unless otherwise stated, the following reactions were carried out in an anhydrous solvent, under a positive pressure of nitrogen or argon gas, or using a drying tube. The reaction flasks were equipped with a rubber diaphragm so as to add substrates and reagents by a syringe. The glassware was dried in an oven and/or dried by heating.

Unless otherwise stated, the purification by column chromatography was performed with silica gel (200-300 mesh) produced by Qingdao Haiyang Chemical Co., Ltd. The separation by preparative thin layer chromatography was performed by using thin layer chromatography silica gel prefabricated plates (HSGF254) manufactured by Yantai Chemical Industry Research Institute. MS was measured by using Thermo LCQ Fleet type (ESI) liquid chromatography-mass spectrometer. The optical rotation was measured by using SWG-3 automatic polarimeter from Shanghai Shenguang Instrument Co., Ltd.

Unless otherwise stated, NMR data ($^1$H-NMR) were taken at 400 Hz by using an equipment from Varian. The solvents used for NMR include $CDCl_3$, $CD_3OD$, $D_2O$, DMSO-d and the like, and tetramethylsilane (0.00 ppm) was used as a baseline or residual solvent was used as a baseline ($CDCl_3$: 7.26 ppm; $CD_3OD$: 3.31 ppm; $D_2O$: 4.79 ppm; DMSO-$d_6$: 2.50 ppm). Upon indicating peak shape diversity, the following abbreviations represent different peak shapes: s (singlet), d (doublet), t (triplet), q (quartet), m (multiplet), br (broad), dd (doublet of doublets), dt (doublet of triplets). If a coupling constant is given, the unit thereof is Hertz (Hz).

Unless otherwise indicated, the absolute configuration of the chiral center is not indicated for the title compounds in some Examples of the present application, and a mixture of all enantiomers was obtained during the preparation of such compounds. Although the enantiomers cannot be separated by an ordinary column chromatography, it does not mean that there are no enantiomers for such compounds.

Example 1: (S)—N—((R)-1-(2-chlorophenyl)-2-((3,3-difluorocyclobutyl)amino)-2-oxoethyl)-2-(4-cyanopyridin-2-yl)-N-(5-fluoropyridin-3-yl)-isothiazolidine-3-carboxamide 1,1-dioxide

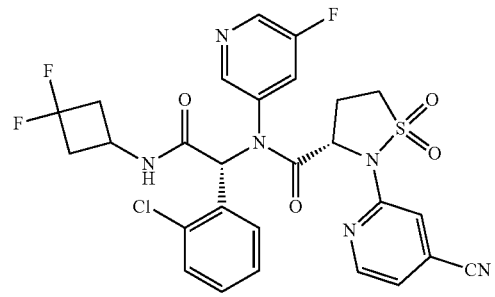

Step A: dimethyl L-homocysteinate dihydrochloride

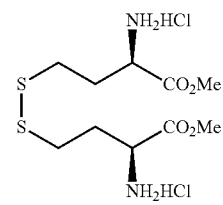

Under stirring in an ice bath, thionyl chloride (10.64 g, 89.4 mmol) was added dropwise into a suspension of L-homocysteine (8.0 g, 29.8 mmol) in methanol. The solution is gradually clear. After the addition was completed, the reaction solution was stirred for 10 min, followed by removing the ice bath, and stirred again at room temperature overnight. The solvent was removed, so as to give dimethyl L-homocysteinate dihydrochloride (10.6 g, yield 100%).

$^1$H-NMR (400 MHz, DMSO-$d_6$): δ=8.79 (s, 6H), 3.75 (s, 6H), 2.95-2.80 (m, 4H), 2.52-2.47 (m, 2H), 2.20-2.10 (m, 4H).

Step B: methyl (S)-2-amino-4-chlorosulfonylbutyrate hydrochloride

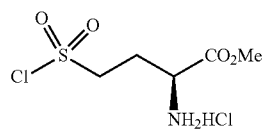

Under stirring in an ice bath, chlorine gas was introduced into a mixed solution of dimethyl L-homocysteinate dihydrochloride (10.6 g, 29.8 mmol) in ethanol (40 mL) and chloroform (80 mL) for 20 minutes, generating a white solid. The reaction solution was filtered and washed with chloroform, to give methyl (S)-2-amino-4-chlorosulfonyl-butyrate hydrochloride (7.5 g, yield 100%).

$^1$H-NMR (400 MHz, DMSO-d$_6$): δ=13.46 (s, 1H), 8.57 (s, 2H), 3.66 (s, 3H), 3.18-2.95 (m, 2H), 2.52-2.45 (m, 1H), 2.22-1.97 (m, 2H).

Step C: methyl (S)-isothiazolidine-3-carboxylate 1,1-dioxide

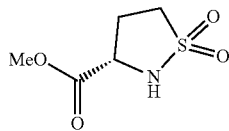 [SMILES: COC(=O)[C@@H]1CCS(=O)(=O)N1]

Under stirring in an ice-salt bath, a solution of triethylamine in chloroform was added dropwise into a suspension of methyl (S)-2-amino-4-chlorosulfonylbutyrate hydrochloride (4.5 g, 17.85 mmol) in chloroform. After the addition of the solution of triethylamine in chloroform was completed, the ice-salt bath was removed. It was stirred overnight at room temperature and the solvent was removed. Then it was filtered with diatomite and washed with ethyl acetate. The solvent was removed to give a light yellow oil, namely methyl (S)-isothiazolidine-3-carboxylate 1,1-dioxide (3.2 g, yield 100%).

$^1$H-NMR (400 MHz, CDCl$_3$): δ=4.98 (s, 1H), 4.21 (dd, J=8.3, 4.6 Hz, 1H), 3.84 (s, 3H), 3.30-3.11 (m, 1H), 3.09-2.90 (m, 1H), 2.90-2.73 (m, 1H), 2.60 (ddd, J=18.4, 8.9, 4.7 Hz, 1H).

Step D: (S)-isothiazolidine-3-carboxylic acid 1,1-dioxide

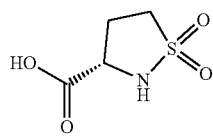

Under stirring in an ice bath, a suspension of lithium hydroxide was added dropwise into a solution of methyl (S)-isothiazolidine-3-carboxylate 1,1-dioxide (2.4 g, 13.4 mmol) in methanol-tetrahydrofuran, reacting overnight, to which 1N hydrochloric acid was added dropwise, so as to make the pH less than 5. The solvent was removed. The residue was filtered and washed with methanol. The solvent was removed to give (S)-isothiazolidine-3-carboxylic acid 1,1-dioxide (2.2 g, yield 100%).

$^1$H-NMR (400 MHz, CDCl$_3$): δ=3.85-3.75 (m, 1H), 3.10-2.85 (m, 2H), 2.55-2.30 (m, 2H).

Step E: (3S)—N-(1-(2-chlorophenyl)-2-((3,3-difluorocyclobutyl)amino)-2-oxoethyl)-N-(5-fluoropyridin-3-yl)-isothiazolidine-3-carboxamide 1,1-dioxide

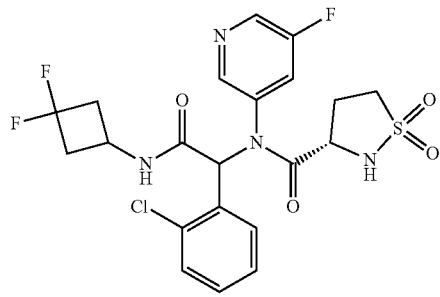 [SMILES: O=C(NC1CC(F)(F)C1)C(c1ccccc1Cl)N(C(=O)[C@@H]1CCS(=O)(=O)N1)c1cncc(F)c1]

At room temperature, 3-amino-5-fluoropyridine (57 mg, 0.508 mmol) and o-chlorobenzaldehyde (72 mg, 0.512 mmol) were dissolved in methanol and stirred for 30 min. (S)-isothiazolidine-3-carboxylic acid 1,1-dioxide (84 mg, 0.508 mmol) was then added into the mixed solution, stirred for 10 min, followed by adding 1,1-difluoro-3-isocyanocyclobutane (prepared according to the method described in patent CN103097340, 60 mg, 0.508 mmol), and stirred overnight. The solvent was removed and the residue was separated by silica gel column chromatography (PE:EA=1:1), to give the desired product (60 mg, yield 22%).

m/z=517 [M+H]$^+$.

Step F: (S)—N—((R)-1-(2-chlorophenyl)-2-((3,3-difluorocyclobutyl)amino)-2-oxoethyl)-2-(4-cyanopyridin-2-yl)-N-(5-fluoropyridin-3-yl)-isothiazolidine-3-carboxamide 1,1-dioxide

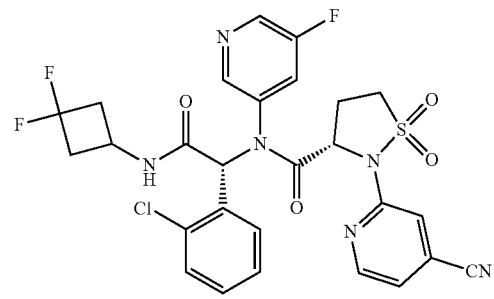 [SMILES: N#Cc1ccnc(N2[C@H](C(=O)N(c3cncc(F)c3)[C@@H](C(=O)NC3CC(F)(F)C3)c3ccccc3Cl)CCS2(=O)=O)c1]

(3S)—N-(1-(2-chlorophenyl)-2-((3,3-difluorocyclobutyl)amino)-2-oxoethyl)-N-(5-fluoropyridin-3-yl)-isothiazolidine-3-carboxamide 1,1-dioxide (60 mg, 0.116 mmol), 2-bromo-4-cyanopyridine (22 mg, 0.139 mmol), cuprous iodide (28 mg, 0.147 mmol), N,N'-dimethylethylenediamine (13 mg, 0.147 mmol) and cesium carbonate (95 mg, 0.29 mmol) were added into a sealed tube reactor, dioxane (8 mL) was added thereto, nitrogen gas was introduced thereto for 5 min and the tube was sealed. They were reacted overnight at 80° C. After the starting materials were consumed, the solvent was removed and then column chromatography (PE:EA=1:1) was performed, to give a racemic product, which was then subjected to thin layer chromatography (DCM:EA=8:1). (S)—N—((R)-1-(2-chlorophenyl)-2-((3,3-difluorocyclobutyl)amino)-2-oxoethyl)-2-(4-cyanopyridin- 2-yl)-N-(5-fluoropyridin-3-yl)-isothiazolidine-3-carboxamide 1,1-dioxide (7 mg, yield 10%) was obtained.

¹H-NMR (400 MHz, CDCl₃): δ=8.56 (d, J=5.1 Hz, 1H), 8.37 (s, 1H), 7.64 (s, 1H), 7.43 (d, J=8.1 Hz, 1H), 7.30-7.05 (m, 6H), 6.35 (s, 1H), 6.20 (s, 1H), 4.65-4.55 (m, 1H), 4.22-4.10 (m, 1H), 3.70-3.60 (m, 1H), 3.42-3.33 (m, 1H), 2.95-2.75 (m, 2H), 2.60-2.50 (m, 2H), 2.35-2.15 (m, 2H).

m/z=619 [M+H]⁺.

HPLC conditions: chiral column: CHIRALPAK®IC-3 column (25 cm); mobile phase: n-hexane/ethanol=85/15; flow rate: 0.8 mL/min; column temperature: 40° C.; wavelength/time: 210 nm, 20 min; retention time: that of the title compound in Example 1 is 17.60 min.

Example 2: (S)—N—((S)-1-(2-chlorophenyl)-2-((3,3-difluorocyclobutyl)amino)-2-oxoethyl)-2-(4-cyanopyridin-2-yl)-N-(5-fluoropyridin-3-yl)-isothiazolidine-3-carboxamide 1,1-dioxide

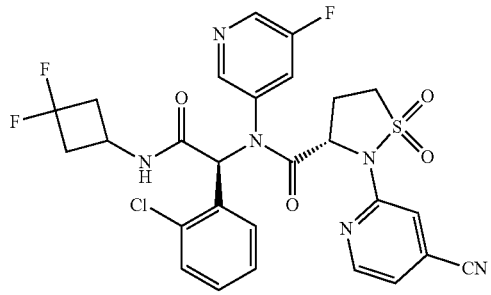 [SMILES: N#Cc1ccnc(N2[C@H](C(=O)N(c3cncc(F)c3)[C@H](C(=O)NC3CC(F)(F)C3)c3ccccc3Cl)CCS2(=O)=O)c1]

In Step F of Example 1, (S)—N—((S)-1-(2-chlorophenyl)-2-((3,3-difluorocyclobutyl)amino)-2-oxoethyl)-2-(4-cyanopyridin-2-yl)-N-(5-fluoropyridin-3-yl)-isothiazolidine-3-carboxamide 1,1-dioxide was isolated by thin layer chromatography.

¹H-NMR (400 MHz, CDCl₃): δ=8.47 (d, J=5.1 Hz, 1H), 8.31 (s, 1H), 8.08 (d, J=8.1 Hz, 1H), 7.62 (s, 1H), 7.30-6.75 (m, 6H), 6.56 (s, 1H), 6.22 (s, 1H), 4.80-4.70 (m, 1H), 4.40-4.30 (m, 1H), 3.75-3.65 (m, 1H), 3.40-3.33 (m, 1H), 3.10-2.98 (m, 2H), 2.60-2.40 (m, 4H).

m/z=619 [M+H]⁺.

HPLC conditions: chiral column: CHIRALPAK®IC-3 column (25 cm); mobile phase: n-hexane/ethanol=85/15; flow rate: 0.8 mL/min; column temperature: 40° C.; wavelength/time: 210 nm, 20 min; retention time: that of the title compound in Example 2 is 17.91 min.

Example 3: (S)—N—((R)-1-(2-chlorophenyl)-2-((3,3-difluorocyclobutyl)amino)-2-oxoethyl)-2-(4-cyanopyridin-2-yl)-N-(3,5-difluorophenyl)-isothiazolidine-3-carboxamide 1,1-dioxide

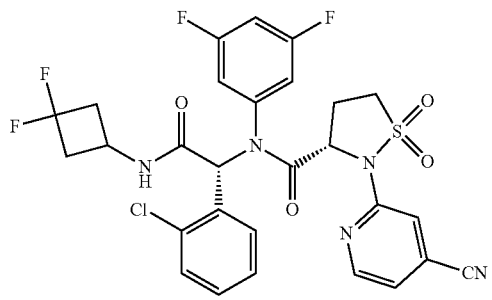 [SMILES: N#Cc1ccnc(N2[C@H](C(=O)N(c3cc(F)cc(F)c3)[C@@H](C(=O)NC3CC(F)(F)C3)c3ccccc3Cl)CCS2(=O)=O)c1]

Step A: (3S)—N-(1-(2-chlorophenyl)-2-((3,3-difluorocyclobutyl)amino)-2-oxoethyl)-N-(3,5-difluorophenyl)-isothiazolidine-3-carboxamide 1,1-dioxide

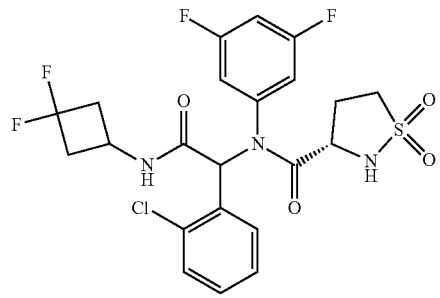 [SMILES: O=C(NC1CC(F)(F)C1)C(c1ccccc1Cl)N(C(=O)[C@@H]1CCS(=O)(=O)N1)c1cc(F)cc(F)c1]

Referring to Step E in Example 1, the reaction material 3-amino-5-fluoropyridine was replaced with 3,5-difluoroaniline to give the desired product of (3S)—N-(1-(2-chlorophenyl)-2-((3,3-difluorocyclobutyl)amino)-2-oxoethyl)-N-(3,5-difluorophenyl)-isothiazolidine-3-carboxamide 1,1-dioxide (yield 13%).

m/z=534 [M+H]⁺.

Step B: (S)—N—((R)-1-(2-chlorophenyl)-2-((3,3-difluorocyclobutyl)amino)-2-oxoethyl)-2-(4-cyanopyridin-2-yl)-N-(3,5-difluorophenyl)-isothiazolidine-3-carboxamide 1,1-dioxide

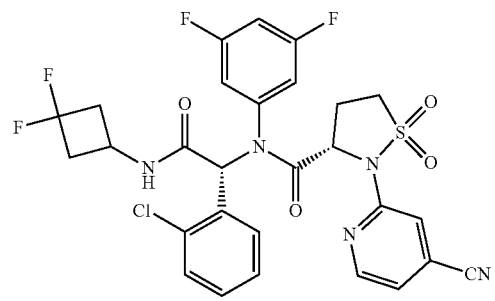

Referring to Step F in Example 1, (S)—N—((R)-1-(2-chlorophenyl)-2-((3,3-difluorocyclobutyl)amino)-2-oxoethyl)-2-(4-cyanopyridin-2-yl)-N-(3,5-difluorophenyl)-isothiazolidine-3-carboxamide 1,1-dioxide was obtained with a yield of 35%.

¹H-NMR (400 MHz, CDCl₃): δ=8.54 (d, J=5.0 Hz, 1H), 7.67 (s, 1H), 7.43-6.76 (m, 8H), 6.11 (s, 1H), 6.01 (s, 1H), 4.80-4.72 (m, 1H), 4.16-4.2 (m, 1H), 3.68-3.65 (m, 1H), 3.38-3.34 (m, 1H), 2.80-2.98 (m, 2H), 2.58-2.54 (m, 2H), 2.28-2.30 (m, 2H).

m/z=636 [M+H]⁺.

Example 4: (S)—N—((S)-1-(2-chlorophenyl)-2-((3,3-difluorocyclobutyl)amino)-2-oxoethyl)-2-(4-cyanopyridin-2-yl)-N-(3,5-difluorophenyl)-isothiazolidine-3-carboxamide 1,1-dioxide

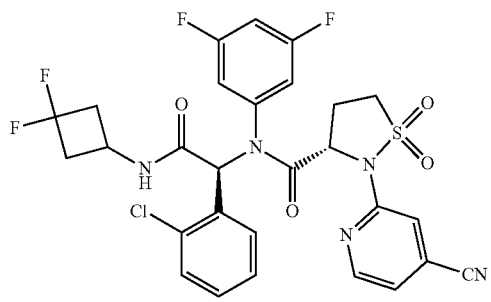 [SMILES: N#Cc1ccnc(N2[C@H](C(=O)N(c3cc(F)cc(F)c3)[C@H](C(=O)NC3CC(F)(F)C3)c3ccccc3Cl)CCS2(=O)=O)c1]

In Step B of Example 3, the title compound was isolated by thin layer chromatography with a yield of 40%.
¹H-NMR (400 MHz, CDCl₃): δ=8.45 (d, J=5.0 Hz, 1H), 7.67 (s, 1H), 7.35-6.66 (m, 8H), 6.46 (s, 1H), 5.93 (d, J=6.8, 1H), 4.85-4.83 (m, 1H), 4.40-4.23 (m, 1H), 3.72-3.69 (m, 1H), 3.37-3.34 (m, 1H), 3.03-2.99 (m, 2H), 2.60-2.20 (m, 4H).
m/z=636 [M+H]⁺.

Example 5: (S)—N—((R)-1-(2-chlorophenyl)-2-((3,3-difluorocyclobutyl)amino)-2-oxoethyl)-2-(4-cyanopyridin-2-yl)-N-(3-trifluoromethylphenyl)-isothiazolidine-3-carboxamide 1,1-dioxide

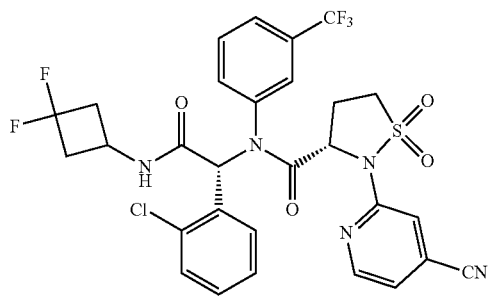 [SMILES: N#Cc1ccnc(N2[C@H](C(=O)N(c3cccc(C(F)(F)F)c3)[C@@H](C(=O)NC3CC(F)(F)C3)c3ccccc3Cl)CCS2(=O)=O)c1]

Step A: (3S)—N-(1-(2-chlorophenyl)-2-((3,3-difluorocyclobutyl)amino)-2-oxoethyl)-N-(3-trifluoromethylphenyl)-isothiazolidine-3-carboxamide 1,1-dioxide

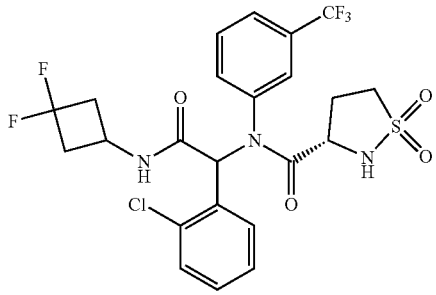 [SMILES: O=C(NC1CC(F)(F)C1)C(c1ccccc1Cl)N(C(=O)[C@@H]1CCS(=O)(=O)N1)c1cccc(C(F)(F)F)c1]

Referring to Step E in Example 1, the reaction material 3-amino-5-fluoropyridine was replaced with 3-trifluoromethylaniline to give the target product, (3S)—N-(1-(2-chlorophenyl)-2-((3,3-difluorocyclobutyl)amino)-2-oxoethyl)-N-(3-trifluoromethylphenyl)-isothiazolidine-3-carboxamide 1,1-dioxide, with a yield of 50%.
¹H-NMR (400 MHz, CDCl₃): δ=8.10 and 8.00 (s, 0.5 and 0.5H), 7.58-6.60 (m, 7H), 6.55 and 6.39 (s, 0.5 and 0.5H), 5.90 (s, 1H), 5.23 and 5.18 (d, J=7.2, 0.5 and 0.5H), 4.40-4.30 (m, 1H), 4.00-3.90 (m, 1H), 3.11-2.96 (m, 4H), 2.59-2.26 (m, 4H).
m/z=566 [M+H]⁺.

Step B: (S)—N—((R)-1-(2-chlorophenyl)-2-((3,3-difluorocyclobutyl)amino)-2-oxoethyl)-2-(4-cyanopyridin-2-yl)-N-(3-trifluoromethylphenyl)-isothiazolidine-3-carboxamide 1,1-dioxide

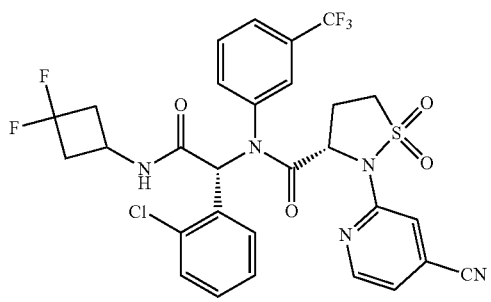

Referring to Step F in Example 1, (S)—N—((R)-1-(2-chlorophenyl)-2-((3,3-difluorocyclobutyl)amino)-2-oxoethyl)-2-(4-cyanopyridin-2-yl)-N-(3-trifluoromethylphenyl)-isothiazolidine-3-carboxamide 1,1-dioxide was obtained with a yield of 16%.
¹H-NMR (400 MHz, CDCl₃): δ=8.54 (d, J=5.0 Hz, 1H), 8.40 (brs, 1H), 7.64-7.05 (m, 9H), 6.32 (m, 2H), 4.68-4.65 (m, 1H), 4.22-4.04 (m, 1H), 3.64-3.59 (m, 1H), 3.34-3.28 (m, 1H), 2.98-2.65 (m, 2H), 2.60-2.43 (m, 2H), 2.38-2.15 (m, 2H).
m/z=668 [M+H]⁺.

Example 6: (S)—N—((S)-1-(2-chlorophenyl)-2-((3,3-difluorocyclobutyl)amino)-2-oxoethyl)-2-(4-cyanopyridin-2-yl)-N-(3-trifluoromethylphenyl)-isothiazolidine-3-carboxamide 1,1-dioxide

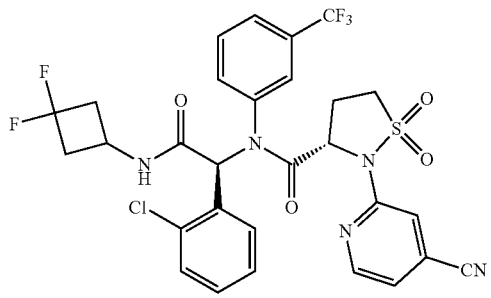

In Step B of Example 5, (S)—N—((S)-1-(2-chlorophenyl)-2-((3,3-difluorocyclobutyl)amino)-2-oxoethyl)-2-(4-cyanopyridin-2-yl)-N-(3-trifluoromethylphenyl)-isothiazolidine-3-carboxamide 1,1-dioxide was isolated by thin layer chromatography with a yield of 23%.

$^1$H-NMR (400 MHz, CDCl$_3$): δ=8.46 (d, J=5.0 Hz, 1H), 8.14 (s, 1H), 7.69-6.81 (m, 9H), 6.45 (s, 1H), 5.88-5.80 (m, 1H), 4.80-4.65 (m, 1H), 4.40-4.25 (m, 1H), 3.82-3.65 (m, 1H), 3.40-3.25 (m, 1H), 3.10-2.90 (m, 2H), 2.70-2.40 (m, 4H).

m/z=668 [M+H]$^+$.

Example 7: (S)—N—((R)-1-(2-chlorophenyl)-2-((3,3-difluorocyclobutyl)amino)-2-oxoethyl)-2-(4-cyanopyridin-2-yl)-N-(3-cyano-5-fluorophenyl)-isothiazolidine-3-carboxamide 1,1-dioxide

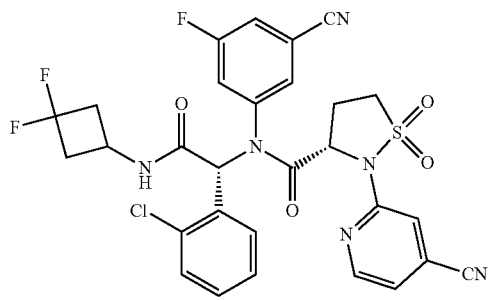 [SMILES: N#Cc1cc(F)cc(N(C(=O)[C@@H]2CCS(=O)(=O)N2c2cc(C#N)ccn2)[C@@H](C(=O)NC2CC(F)(F)C2)c2ccccc2Cl)c1]

Step A: (3S)—N-(1-(2-chlorophenyl)-2-((3,3-difluorocyclobutyl)amino)-2-oxoethyl)-N-(3-cyano-5-fluorophenyl)-isothiazolidine-3-carboxamide 1,1-dioxide

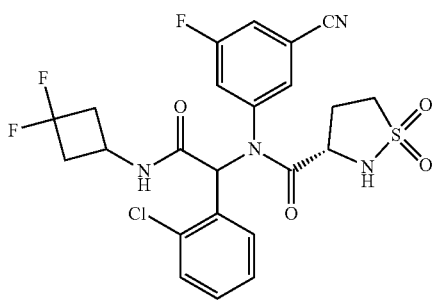 [SMILES: N#Cc1cc(F)cc(N(C(=O)[C@@H]2CCS(=O)(=O)N2)C(C(=O)NC2CC(F)(F)C2)c2ccccc2Cl)c1]

Referring to Step E in Example 1, the starting material 3-amino-5-fluoropyridine was replaced with 3-fluoro-5-cyanoaniline to give the target product with a yield of 17%.

m/z=541 [M+H]$^+$.

Step B: (S)—N—((R)-1-(2-chlorophenyl)-2-((3,3-difluorocyclobutyl)amino)-2-oxoethyl)-2-(4-cyanopyridin-2-yl)-N-(3-cyano-5-fluorophenyl)-isothiazolidine-3-carboxamide 1,1-dioxide

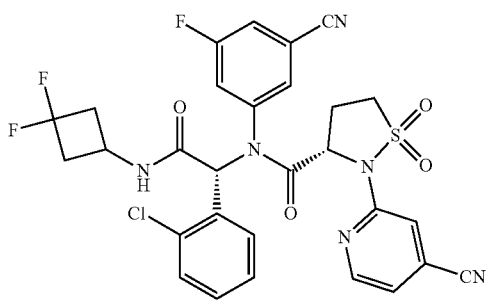

Referring to Step F in Example 1, (S)—N—((R)-1-(2-chlorophenyl)-2-((3,3-difluorocyclobutyl)amino)-2-oxoethyl)-2-(4-cyanopyridin-2-yl)-N-(3-cyano-5-fluorophenyl)-isothiazolidine-3-carboxamide 1,1-dioxide was obtained with a yield of 15%.

$^1$H-NMR (400 MHz, CDCl$_3$): δ=8.83 (d, J=6.0 Hz, 1H), 8.57 (d, J=5.0 Hz, 1H), 7.66-7.12 (m, 8H), 6.29 (s, 1H), 6.16 (s, 1H), 4.63-4.61 (m, 1H), 4.21-4.10 (m, 1H), 3.70-3.60 (m, 1H), 3.40-3.25 (m, 1H), 3.30-2.82 (m, 2H), 2.61-2.42 (m, 2H), 2.40-2.20 (m, 2H).

m/z=643 [M+H]$^+$.

Example 8: (S)—N—((S)-1-(2-chlorophenyl)-2-((3,3-difluorocyclobutyl)amino)-2-oxoethyl)-2-(4-cyanopyridin-2-yl)-N-(3-cyano-5-fluorophenyl)-isothiazolidine-3-carboxamide 1,1-dioxide

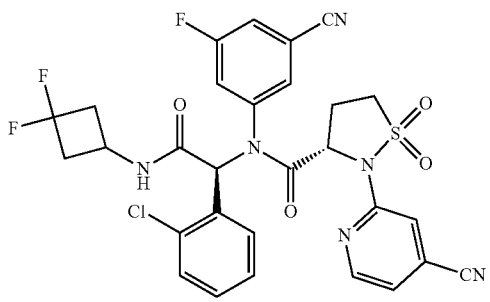

In Step B of Example 7, the title compound was isolated by thin layer chromatography with a yield of 20%.

$^1$H-NMR (400 MHz, CDCl$_3$): δ=8.47-6.85 (m, 10H), 6.50 (d, J=9.77 Hz, 1H), 5.97 (s, 1H), 4.75-4.73 (m, 1H), 4.40-4.30 (m, 1H), 3.80-3.65 (m, 1H), 3.42-3.27 (m, 1H), 3.15-2.30 (m, 6H).

m/z=643 [M+H]$^+$.

Example 9: (S)—N—((R)-1-(2-chlorophenyl)-2-((3,3-difluorocyclobutyl)amino)-2-oxoethyl)-2-(4-cyanopyridin-2-yl)-N-(3,4-difluorophenyl)-isothiazolidine-3-carboxamide 1,1-dioxide

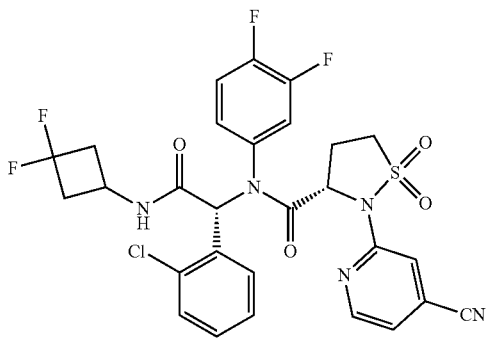 [SMILES: N#Cc1ccnc(N2[C@H](C(=O)N(c3ccc(F)c(F)c3)[C@@H](C(=O)NC3CC(F)(F)C3)c3ccccc3Cl)CCS2(=O)=O)c1]

Step A: (3S)—N-(1-(2-chlorophenyl)-2-((3,3-difluorocyclobutyl)amino)-2-oxoethyl)-N-(3,4-difluorophenyl)-isothiazolidine-3-carboxamide 1,1-dioxide

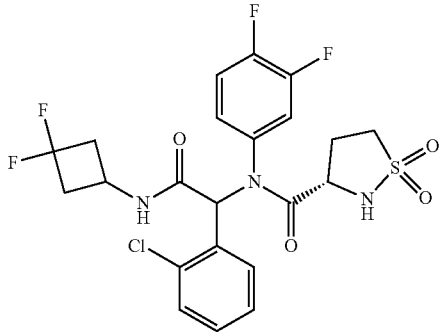 [SMILES: O=C(NC1CC(F)(F)C1)C(c1ccccc1Cl)N(C(=O)[C@@H]1CCS(=O)(=O)N1)c1ccc(F)c(F)c1]

Referring to Step E of Example 1, the starting material 3-amino-5-fluoropyridine was replaced with 3,4-difluoroaniline to give the target product with a yield of 18%.
m/z=534 [M+H]$^+$.

Step B: (S)—N—((R)-1-(2-chlorophenyl)-2-((3,3-difluorocyclobutyl)amino)-2-oxoethyl)-2-(4-cyanopyridin-2-yl)-N-(3,4-difluorophenyl)-isothiazolidine-3-carboxamide 1,1-dioxide

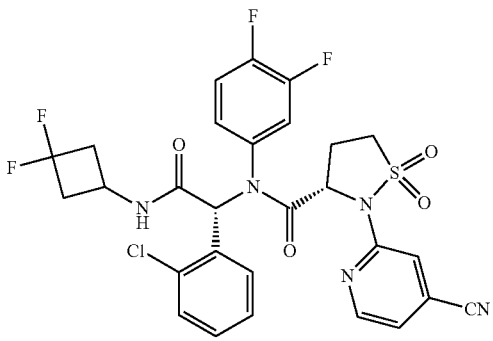 [SMILES: N#Cc1ccnc(N2[C@H](C(=O)N(c3ccc(F)c(F)c3)[C@@H](C(=O)NC3CC(F)(F)C3)c3ccccc3Cl)CCS2(=O)=O)c1]

Referring to Step F of Example 1, (S)—N—((R)-1-(2-chlorophenyl)-2-((3,3-difluorocyclobutyl)amino)-2-oxoethyl)-2-(4-cyanopyridin-2-yl)-N-(3,4-difluorophenyl)-isothiazolidine-3-carboxamide 1,1-dioxide was obtained with a yield of 30%.

$^1$H-NMR (400 MHz, CDCl$_3$): δ=8.55 (s, 1H), 7.62 (s, 1H), 7.40-7.15 (m, 8H), 6.43 (s, 1H), 6.27 (s, 1H), 4.70-4.68 (m, 1H), 4.15-4.11 (m, 1H), 3.61-3.53 (m, 1H), 3.32-3.26 (m, 1H), 2.89-2.69 (m, 2H), 2.57-2.53 (m, 2H), 2.28-2.11 (m, 2H).

m/z=636 [M+H]$^+$.

Example 10: (S)—N—((S)-1-(2-chlorophenyl)-2-((3,3-difluorocyclobutyl)amino)-2-oxoethyl)-2-(4-cyanopyridin-2-yl)-N-(3,4-difluorophenyl)-isothiazolidine-3-carboxamide 1,1-dioxide

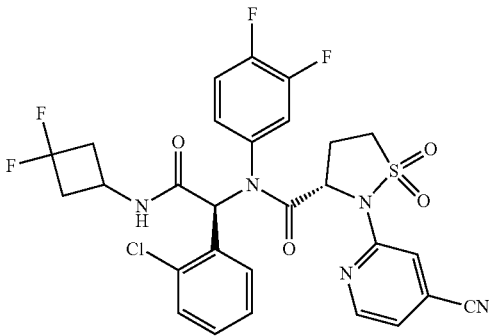 [SMILES: N#Cc1ccnc(N2[C@H](C(=O)N(c3ccc(F)c(F)c3)[C@H](C(=O)NC3CC(F)(F)C3)c3ccccc3Cl)CCS2(=O)=O)c1]

In Step B of Example 9, the title compound was isolated by thin layer chromatography with a yield of 35%.

$^1$H-NMR (400 MHz, CDCl$_3$): δ=8.47-8.43 (m, 1H), 7.66 (s, 1H), 7.35-6.82 (m, 8H), 6.44 (d, J=5.78, 1H), 5.97 (d, J=6.57, 1H), 4.81-4.79 (m, 1H), 4.33-4.32 (m, 1H), 3.73-3.69 (m, 1H), 3.36-3.33 (m, 1H), 3.02-2.99 (m, 2H), 2.61-2.40 (m, 4H).

m/z=636 [M+H]$^+$.

Example 11: (S)—N—((R)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide

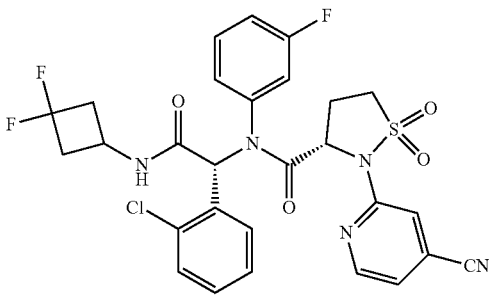 [SMILES: N#Cc1ccnc(N2[C@H](C(=O)N(c3cccc(F)c3)[C@@H](C(=O)NC3CC(F)(F)C3)c3ccccc3Cl)CCS2(=O)=O)c1]

Step A: methyl (S)-2-(4-cyanopyridin-2-yl)isothiazolidine-3-carboxylate 1,1-dioxide

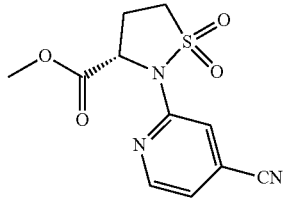 [SMILES: COC(=O)[C@@H]1CCS(=O)(=O)N1c1cc(C#N)ccn1]

Methyl (S)-isothiazolidine-3-carboxylate 1,1-dioxide (prepared by Step C of Example 1, 200 mg, 1.11 mmol), 2-bromo-4-cyanopyridine (204 mg, 1.11 mmol), cuprous iodide (105 mg, 0.55 mmol), N,N'-dimethylethylenediamine (98 mg, 1.11 mmol) and cesium carbonate (723 mg, 2.22 mmol) were added into a sealed tube reactor, dioxane (8 mL) was added thereto, nitrogen gas was introduced thereto for 5 min and the tube was sealed. They were reacted overnight at 80° C. After the starting materials were consumed, the solvent was removed and then separation by column chromatography (PE:EA=1:1) was performed. The target product methyl (S)-2-(4-cyanopyridin-2-yl)isothiazolidine-3-carboxylate 1,1-dioxide (230 mg, yield 74%) was obtained.

$^1$H-NMR (400 MHz, CDCl$_3$): δ=8.40 (dd, J=5.2, 0.8 Hz, 1H), 7.69 (t, J=1.0 Hz, 1H), 7.19 (dd, J=5.2, 1.0 Hz, 1H), 5.01 (dd, J=8.0, 3.6 Hz, 1H), 3.78 (s, 3H), 3.64-3.55 (m, 1H), 3.48-3.42 (m, 1H), 2.95-2.84 (m, 1H), 2.65-2.52 (m, 1H).

Step B: (S)-2-(4-cyanopyridin-2-yl)isothiazolidine-3-carboxylic acid 1,1-dioxide

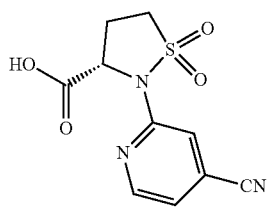 [SMILES: N#Cc1ccnc(N2[C@H](C(=O)O)CCS2(=O)=O)c1]

Under stirring in an ice bath, a suspension of lithium hydroxide was added dropwise into a solution of methyl (S)-2-(4-cyanopyridin-2-yl)isothiazolidine-3-carboxylate 1,1-dioxide (116 mg, 0.41 mmol) in methanol-tetrahydrofuran, reacting overnight. After the reaction was finished, it was diluted with 10 mL water, and extracted with ethyl acetate to remove impurities. The aqueous phase was added dropwise with 1 N hydrochloric acid to make the pH thereof less than 5, and then extracted with ethyl acetate. The solvent was removed to give (S)-2-(4-cyanopyridin-2-yl)isothiazolidine-3-carboxylic acid 1,1-dioxide (103 mg, yield 94%).

$^1$H-NMR (400 MHz, DMSO-d$_6$): δ=13.5 (s, 1H), 8.54 (d, J=5.0, 1H), 7.51 (dd, J=3.74, 4.76 Hz, 1H), 7.45 (s, 1H), 4.95-4.90 (m, 1H), 3.75-3.60 (m, 2H), 2.85-2.72 (m, 1H), 2.46-2.38 (m, 1H).

Step C: (S)—N—((R)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide

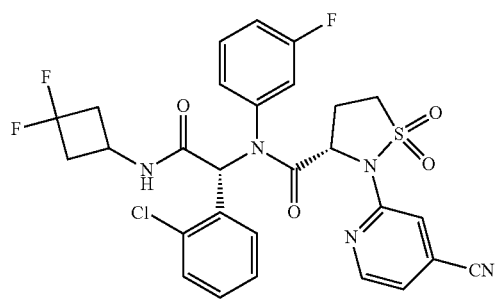 [SMILES: N#Cc1ccnc(N2[C@H](C(=O)N(c3cccc(F)c3)[C@@H](C(=O)NC3CC(F)(F)C3)c3ccccc3Cl)CCS2(=O)=O)c1]

Referring to Step E in Example 1, the starting material (S)-isothiazolidine-3-carboxylic acid 1,1-dioxide was replaced with (S)-2-(4-cyanopyridin-2-yl)isothiazolidine-3-carboxylic acid 1,1-dioxide to give the target product, (S)—N—((R)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide, with a yield of 30%.

$^1$H-NMR (400 MHz, CDCl$_3$): δ=8.56 (d, J=5.0 Hz, 1H), 7.62 (s, 1H), 7.39 (d, J=8.1 Hz, 1H), 7.21-6.99 (m, 8H), 6.43 (s, 1H), 6.23 (s, 1H), 4.73 (dd, J=6.5, 3.1 Hz, 1H), 4.20-4.05 (m, 1H), 3.57 (dd, J=20.0, 11.9 Hz, 1H), 3.27 (dd, J=11.9, 3.5 Hz, 1H), 2.84-2.72 (m, 2H), 2.55 (dd, J=14.9, 9.3 Hz, 2H), 2.28-2.13 (m, 2H).

m/z=618 [M+H]$^+$.

Example 12: (S)—N—((S)-1-(2-chlorophenyl)-2-((3,3-difluorocyclobutyl)amino)-2-oxoethyl)-2-(4-cyanopyridin-2-yl)-N-(3-fluorophenyl)-isothiazolidine-3-carboxamide 1,1-dioxide

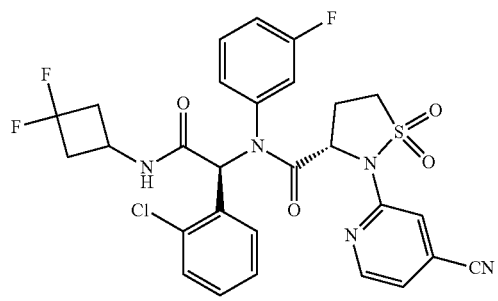 [SMILES: N#Cc1ccnc(N2[C@H](C(=O)N(c3cccc(F)c3)[C@H](C(=O)NC3CC(F)(F)C3)c3ccccc3Cl)CCS2(=O)=O)c1]

In Step C of Example 11, the title compound was isolated by thin layer chromatography with a yield of 33%.

$^1$H-NMR (400 MHz, CDCl$_3$): δ=8.46 (m, 1H), 7.67 (d, J=8.8 Hz, 1H), 7.63 (s, 1H), 7.22-6.84 (m, 8H), 6.47 (d, J=3.6, 1H), 6.08 (s, 1H), 4.82 (d, J=6.1 Hz, 1H), 4.33 (m, 1H), 3.68-3.60 (m, 1H), 3.40-3.28 (m, 1H), 3.10-2.98 (m, 2H), 2.68-2.38 (m, 4H).

m/z=618 [M+H]$^+$.

Example 13: (S)—N—((R)-1-(2-chlorophenyl)-2-(cyclohexylamino)-2-oxoethyl)-2-(pyrimidin-2-yl)-N-(3-fluorophenyl)-isothiazolidine-3-carboxamide 1,1-dioxide

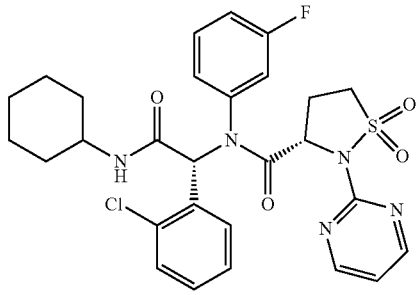 [SMILES: O=C(NC1CCCCC1)[C@@H](c1ccccc1Cl)N(C(=O)[C@@H]1CCS(=O)(=O)N1c1ncccn1)c1cccc(F)c1]

Step A: (S)—N-(1-(2-chlorophenyl)-2-(cyclohexylamino)-2-oxoethyl)-N-(3-fluorophenyl)-isothiazolidine-3-carboxamide 1,1-dioxide

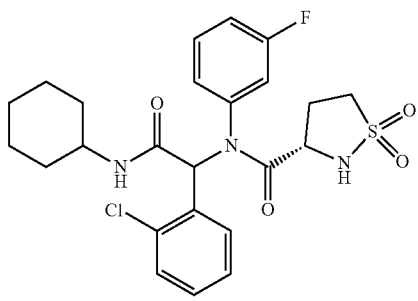 [SMILES: O=C(NC1CCCCC1)C(c1ccccc1Cl)N(C(=O)[C@@H]1CCS(=O)(=O)N1)c1cccc(F)c1]

Referring to Step E in Example 1, the reaction materials 2,2-difluorocyclobutyl isocyanide and 3-amino-5-fluoropyridine were replaced with cyclohexyl isocyanide and 3-fluoroaniline. The target product was obtained with a yield of 81%.
$^1$H-NMR (400 MHz, CDCl$_3$): δ=7.70-6.86 (m, 8H), 6.50-6.25 (m, 1H), 5.41-5.35 (m, 1H), 5.25-5.10 (m, 1H), 4.05-4.95 (m, 1H), 3.90-3.80 (m, 1H), 3.12-2.90 (m, 2H), 2.65-1.00 (m, 12H).
m/z=508 [M+H]$^+$.

Step B: (S)—N—((R)-1-(2-chlorophenyl)-2-(cyclohexylamino)-2-oxoethyl)-2-(pyrimidin-2-yl)-N-(3-fluorophenyl)-isothiazolidine-3-carboxamide 1,1-dioxide

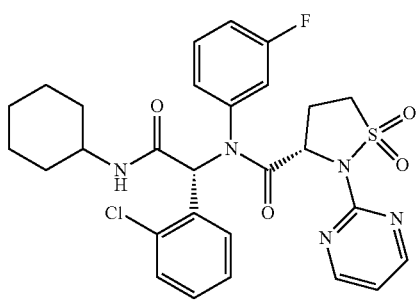 [SMILES: O=C(NC1CCCCC1)[C@@H](c1ccccc1Cl)N(C(=O)[C@@H]1CCS(=O)(=O)N1c1ncccn1)c1cccc(F)c1]

Referring to Step F in Example 1, (S)—N—((R)-1-(2-chlorophenyl)-2-(cyclohexylamino)-2-oxoethyl)-2-(pyrimidin-2-yl)-N-(3-fluorophenyl)-isothiazolidine-3-carboxamide 1,1-dioxide was obtained with a yield of 26%.
$^1$H-NMR (400 MHz, CDCl$_3$): δ=8.61 (d, J=4.9 Hz, 2H), 7.75 (brs, 1H), 7.42-7.37 (m, 2H), 7.26-7.21 (m, 2H), 7.01-7.07 (m, 1H), 7.02-6.96 (m, 2H), 6.85 (brs, 1H), 6.12 (s, 1H), 5.71 (d, J=8.4 Hz, 1H), 4.75 (d, J=5.6 Hz, 1H), 3.76-3.68 (m, 2H), 3.34-3.30 (m, 1H), 2.53-2.46 (m, 2H), 1.86-1.78 (m, 2H), 1.52-1.62 (m, 4H), 1.24-1.30 (m, 2H), 1.12-0.73 (m, 2H).
m/z=586 [M+H]$^+$.

Example 14: (S)—N—((S)-1-(2-chlorophenyl)-2-(cyclohexylamino)-2-oxoethyl)-2-(pyrimidin-2-yl)-N-(3-fluorophenyl)-isothiazolidine-3-carboxamide 1,1-dioxide

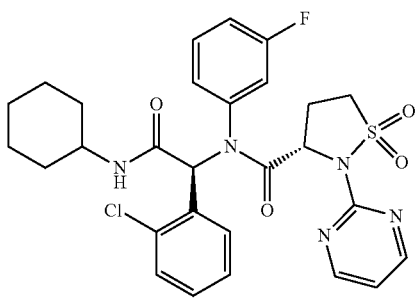 [SMILES: O=C(NC1CCCCC1)[C@H](c1ccccc1Cl)N(C(=O)[C@@H]1CCS(=O)(=O)N1c1ncccn1)c1cccc(F)c1]

In Step B of Example 13, the title compound was isolated by thin layer chromatography with a yield of 30%.
$^1$H-NMR (400 MHz, CDCl$_3$): δ=8.57 (d, J=4.9 Hz, 2H), 7.74 (s, 1H), 7.43-6.88 (m, 7H), 6.49 (s, 1H), 5.40 (d, J=7.9 Hz, 1H), 4.79 (s, 1H), 3.84-3.75 (m, 2H), 3.33-3.30 (m, 1H), 2.62-2.37 (m, 2H), 1.86-1.78 (m, 2H), 1.52-1.62 (m, 4H), 1.24-1.30 (m, 2H), 1.12-0.73 (m, 2H).
m/z=586 [M+H]$^+$.

Example 15: (S)—N—((R)-1-(2-chlorophenyl)-2-(cyclohexylamino)-2-oxoethyl)-2-(4-cyanopyridin-2-yl)-N-(3-fluorophenyl)-isothiazolidine-3-carboxamide 1,1-dioxide

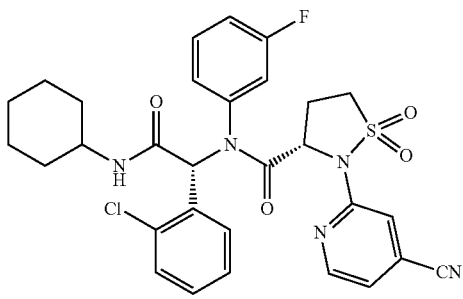 [SMILES: N#Cc1ccnc(N2[C@H](C(=O)N(c3cccc(F)c3)[C@@H](C(=O)NC3CCCCC3)c3ccccc3Cl)CCS2(=O)=O)c1]

Referring to Step F in Example 1, the target product was obtained from (S)—N-(1-(2-chlorophenyl)-2-(cyclohexylamino)-2-oxoethyl)-N-(3-fluorophenyl)-isothiazolidine-3-carboxamide 1,1-dioxide (prepared by Step A of Example 13) with a yield of 39%.

¹H-NMR (400 MHz, CDCl₃): δ=8.56 (d, J=5.0 Hz, 1H), 7.70 (s, 1H), 7.67 (s, 1H), 7.35-6.99 (m, 8H), 6.12 (s, 1H), 5.70 (d, J=7.4 Hz, 1H), 4.75-4.74 (m, 1H), 3.76-3.56 (m, 2H), 3.34-3.36 (m, 1H), 2.66-2.43 (m, 2H), 1.85-1.71 (m, 2H), 1.62-1.56 (m, 4H), 1.28-1.24 (m, 2H), 1.12-0.85 (m, 2H).

m/z=610 [M+H]⁺.

Example 16: (S)—N—((S)-1-(2-chlorophenyl)-2-(cyclohexylamino)-2-oxoethyl)-2-(4-cyanopyridin-2-yl)-N-(3-fluorophenyl)-isothiazolidine-3-carboxamide 1,1-dioxide

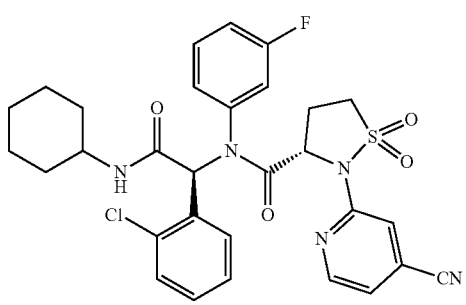 [SMILES: N#Cc1ccnc(N2[C@H](C(=O)N(c3cccc(F)c3)[C@H](C(=O)NC3CCCCC3)c3ccccc3Cl)CCS2(=O)=O)c1]

In Step B of Example 15, the title compound was isolated by thin layer chromatography with a yield of 39%.

¹H-NMR (400 MHz, CDCl₃): δ=8.46 (d, J=5.0 Hz, 1H), 7.75-6.88 (m, 10H), 6.45 (s, 1H), 5.36-5.30 (m, 1H), 4.82-4.81 (m, 1H), 3.82-3.74 (m, 2H), 3.34-3.32 (m, 1H), 2.67-2.65 (m, 1H), 2.45-2.40 (m, 1H), 1.97-1.94 (m, 2H), 1.74-1.59 (m, 4H), 1.38-1.24 (m, 2H), 1.17-1.01 (m, 2H).

m/z=610 [M+H]⁺.

Example 17: (S)—N—((R)-1-(2-chlorophenyl)-2-(cyclohexylamino)-2-oxoethyl)-2-(4-fluoropyridin-2-yl)-N-(3-fluorophenyl)-isothiazolidine-3-carboxamide 1,1-dioxide

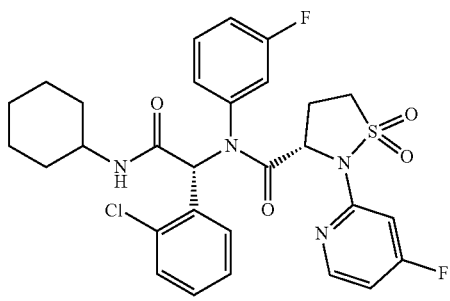 [SMILES: O=C(NC1CCCCC1)[C@@H](c1ccccc1Cl)N(C(=O)[C@@H]1CCS(=O)(=O)N1c1cc(F)ccn1)c1cccc(F)c1]

Referring to Step F in Example 1, (S)—N-(1-(2-chlorophenyl)-2-(cyclohexylamino)-2-oxoethyl)-N-(3-fluorophenyl)-isothiazolidine-3-carboxamide 1,1-dioxide (prepared by Step A of Example 13) was coupled with 2-bromo-4-fluoropyridine to give the target product with a yield of 25%.

¹H-NMR (400 MHz, CDCl₃): δ=8.32 (dd, J=8.4, 5.9 Hz, 1H), 7.45-6.73 (m, 10H), 6.03 (s, 1H), 5.73 (s, 1H), 4.88-4.68 (m, 1H), 3.76-3.62 (m, 2H), 3.29 (ddd, J=12.0, 6.7, 2.6 Hz, 1H), 2.67-2.39 (m, 2H), 1.85-1.75 (m, 2H), 1.62-1.56 (m, 2H), 1.32-1.25 (m, 3H), 1.05-0.91 (m, 3H).

m/z=603 [M+H]⁺.

Example 18: (S)—N—((S)-1-(2-chlorophenyl)-2-(cyclohexylamino)-2-oxoethyl)-2-(4-fluoropyridin-2-yl)-N-(3-fluorophenyl)-isothiazolidine-3-carboxamide 1,1-dioxide

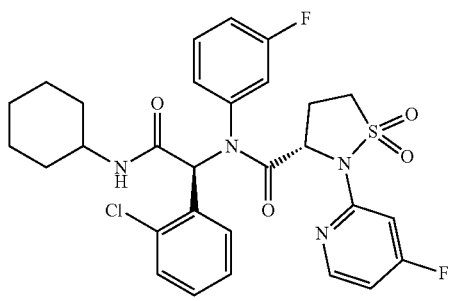

In Step B of Example 17, the title compound was isolated by thin layer chromatography with a yield of 25%.

¹H-NMR (400 MHz, CDCl₃): δ=8.26 (s, 1H), 7.37-6.72 (m, 10H), 6.45 (s, 1H), 5.37 (d, J=8.1, 1H), 4.83 (d, J=7.7, 1H), 3.83-3.70 (m, 2H), 3.29 (ddd, J=12.0, 6.7, 2.6 Hz, 1H), 2.65-2.62 (m, 1H), 2.42-2.25 (m, 1H), 1.94-1.91 (m, 2H), 1.68-1.56 (m, 2H), 1.32-1.25 (m, 3H), 1.05-0.91 (m, 3H).

m/z=603 [M+H]⁺.

Example 19: (3S)—N-(1-(2-chlorophenyl)-2-(cyclohexylamino)-2-oxoethyl)-N-(3-fluorophenyl)-2-(4-ethynylpyridin-2-yl)isothiazolidine-3-carboxamide 1,1-dioxide

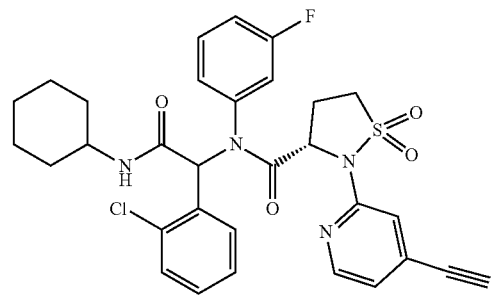 [SMILES: C#Cc1ccnc(N2[C@H](C(=O)N(c3cccc(F)c3)C(C(=O)NC3CCCCC3)c3ccccc3Cl)CCS2(=O)=O)c1]

Step A: 2-bromo-4-(2,2-dibromovinyl)pyridine

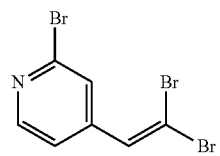 [SMILES: BrC(Br)=Cc1ccnc(Br)c1]

At 0° C., triphenylphosphine (4.23 g, 16.13 mmol) was added to a solution of carbon tetrabromide (2.68 g, 8.08 mmol) in dichloromethane, stirring the same for 5 min, followed by adding 2-bromo-4-aldehyde pyridine (0.50 g, 2.69 mmol) in methanol, warming up the same to room temperature and continuing to stir for a further 30 min. After being completed, the reaction was stopped by adding water. It was extracted with ethyl acetate (30 mL×3) and the organic phase was dried over anhydrous sodium sulfate. The product (140 mg, yield 15%) was obtained by isolating through silica gel column chromatography (PE:EA=10:1).

$^1$H-NMR (400 MHz, CDCl$_3$): δ=8.39-8.38 (m, 1H), 7.63-7.62 (m, 1H), 7.40-7.38 (m, 2H).

Step B: 2-bromo-4-((trimethylsilyl)ethynyl)pyridine

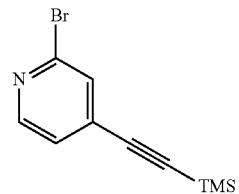 [SMILES: C[Si](C)(C)C#Cc1ccnc(Br)c1]

At −78° C., 2.4M n-butyllithium (358 μL, 0.86 mmol) was added dropwise to a solution of 2-bromo-4-(2,2-dibromovinyl)pyridine (140 mg, 0.41 mmol) in tetrahydrofuran. After stirring for 30 min, trimethylchlorosilane (53 μL, 0.61 mmol) was further added thereto. They were stirred at −78° C. for 1 h, then warmed up to room temperature and further stirred for 30 min. After being completed, the reaction was stopped by adding water. It was extracted with ethyl acetate (30 mL×3) and the organic phase was dried over anhydrous sodium sulfate. The product (30 mg, yield 29%) was obtained by isolating through silica gel column chromatography (PE:EA=20:1).

$^1$H-NMR (400 MHz, CDCl$_3$): δ=8.32-8.30 (m, 1H), 7.52-7.51 (m, 1H), 7.27-7.24 (m, 1H), 0.28-0.25 (m, 9H).

Step C: (3S)—N-(1-(2-chlorophenyl)-2-(cyclohexylamino)-2-oxoethyl)-N-(3-fluorophenyl)-2-(4-ethynylpyridin-2-yl)isothiazolidine-3-carboxamide 1,1-dioxide

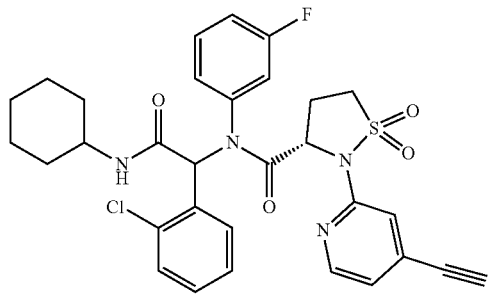 [SMILES: C#Cc1ccnc(N2[C@H](C(=O)N(c3cccc(F)c3)C(C(=O)NC3CCCCC3)c3ccccc3Cl)CCS2(=O)=O)c1]

At 80° C., in 1,4-dioxane (8 mL), (S)—N-(1-(2-chlorophenyl)-2-(cyclohexylamino)-2-oxoethyl)-N-(3-fluorophenyl)-isothiazolidine-3-carboxamide 1,1-dioxide (prepared by Step A of Example 13, 60 mg, 0.12 mmol), 2-bromo-4-[(trimethylsilyl)ethynyl]pyridine (30 mg, 0.12 mmol), cuprous iodide (12 mg, 0.06 mmol), N,N'-dimethylethylenediamine (13 μL, 0.12 mmol) and cesium carbonate (77 mg, 0.24 mmol) were stirred overnight. After the reaction was completed, the mixture was filtered and the mother liquor was concentrated. The title compound (5 mg, yield 7%) was obtained by isolating through silica gel column chromatography (PE:EA=1:1).

$^1$H-NMR (400 MHz, CDCl$_3$): δ=8.36-8.30 (m, 1H), 7.73 (m, 1H), 7.55 (m, 1H), 7.46-7.30 (m, 2H), 7.24-6.88 (m, 6H), 6.46 and 6.03 (s, 1H), 5.74 and 5.39 (d, J=6.4 Hz, 1H), 4.80 and 4.75 (m, 1H), 3.81-3.66 (m, 3H), 3.31-3.28 (m, 1H), 2.62-2.49 (m, 2H), 2.05-1.55 (m, 6H), 1.15-0.84 (m, 4H).

m/z=609 [M+H]$^+$.

Example 20: (3S)—N-(1-(2-chlorophenyl)-2-(cyclohexylamino)-2-oxoethyl)-2-(4-cyanopyridin-2-yl)-N-(3-(N-(4-cyanopyridin-2-yl)aminosulfonyl)phenyl)-isothiazolidine-3-carboxamide 1,1-dioxide

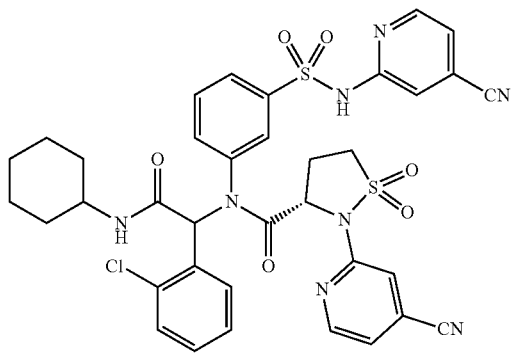 [SMILES: N#Cc1ccnc(NS(=O)(=O)c2cccc(N(C(=O)[C@@H]3CCS(=O)(=O)N3c3cc(C#N)ccn3)C(C(=O)NC3CCCCC3)c3ccccc3Cl)c2)c1]

Step A: (3S)—N-(1-(2-chlorophenyl)-2-(cyclohexylamino)-2-oxoethyl)-2-N-(3-aminosulfonyl)-isothiazolidine-3-carboxamide 1,1-dioxide

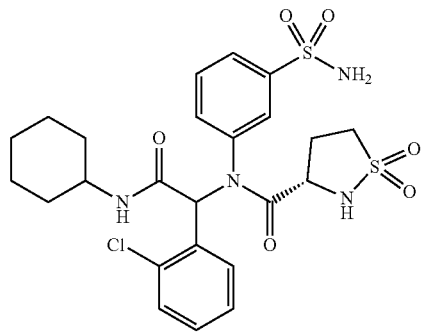 [SMILES: NS(=O)(=O)c1cccc(N(C(=O)[C@@H]2CCS(=O)(=O)N2)C(C(=O)NC2CCCCC2)c2ccccc2Cl)c1]

Referring to Step E in Example 1, the starting material 3-fluoro-5-aminopyridine was replaced with 3-aminobenzenesulfonamide, so as to give the target product with a yield of 53%.

m/z=569 [M+H]$^+$.

Step B: (3S)—N-(1-(2-chlorophenyl)-2-(cyclohexylamino)-2-oxoethyl)-2-(4-cyanopyridin-2-yl)-N-(3-(N-(4-cyanopyridin-2-yl)aminosulfonyl)phenyl)-isothiazolidine-3-carboxamide 1,1-dioxide

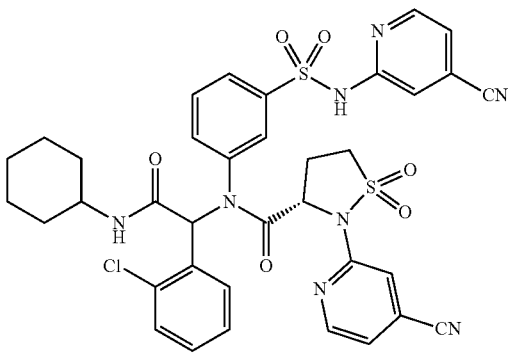 [SMILES: N#Cc1ccnc(NS(=O)(=O)c2cccc(N(C(=O)[C@@H]3CCS(=O)(=O)N3c3cc(C#N)ccn3)C(C(=O)NC3CCCCC3)c3ccccc3Cl)c2)c1]

Referring to Step F of Example 1, the title compound was obtained with a yield of 25%.

$^1$H-NMR (400 MHz, CDCl$_3$): δ=8.60-6.60 (m, 14H), 6.41-6.39 (s, 1H), 6.18-5.56 (s, 1H), 5.44-5.36 (m, 1H), 4.62-4.59 (m, 1H), 3.90-3.61 (m, 2H), 3.40-3.33 (m, 1H), 2.60-2.24 (m, 2H), 2.00-0.80 (m, 10H).

m/z=773 [M+H]$^+$.

Example 21: (S)—N-(1-(2-chlorophenyl)-2-(cyclohexylamino)-2-oxoethyl)-2-(3-cyanophenylethyl)-N-(3-fluorophenyl)-isothiazolidine-3-carboxamide 1,1-dioxide

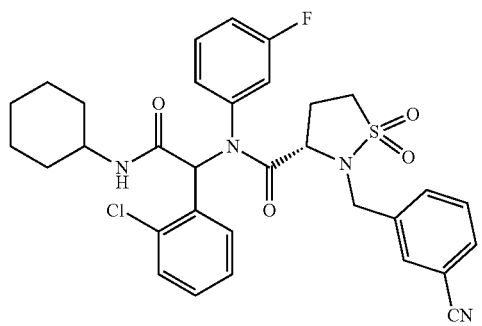 [SMILES: N#Cc1cccc(CN2[C@H](C(=O)N(c3cccc(F)c3)C(C(=O)NC3CCCCC3)c3ccccc3Cl)CCS2(=O)=O)c1]

Step A: methyl (S)-2-(3-cyanophenylethyl-2-yl) isothiazolidine-3-carboxylate 1,1-dioxide

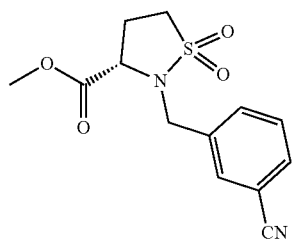 [SMILES: COC(=O)[C@@H]1CCS(=O)(=O)N1Cc1cccc(C#N)c1]

Methyl (S)-isothiazolidine-3-carboxylate 1,1-dioxide (179 mg, 1.0 mmol), 3-cyanobenzyl bromide (392 mg, 2.0 mmol), tetrabutylammonium iodide (37 mg, 0.1 mmol) were dissolved in DMF (3 mL). The reaction solution was stirred overnight at room temperature, diluted by adding water, extracted with ethyl acetate, dried, filtered and concentrated. The crude product was obtained by isolating through silica gel column chromatography to give the target product (260 mg, yield 88%)

$^1$H-NMR (400 MHz, CDCl$_3$): δ=7.66 (s, 1H), 7.65-7.59 (m, 2H), 7.47 (t, J=7.6 Hz, 1H), 4.41 (q, J=15.6 Hz, 2H), 3.85-3.82 (m, 1H), 3.63 (s, 3H) 3.40-3.25 (m, 1H), 3.23-3.16 (m, 1H), 2.66-2.42 (m, 2H).

Step B: (S)-methyl 2-(3-cyanophenylethyl-2-yl) isothiazolidine-3-carboxylic acid 1,1-dioxide

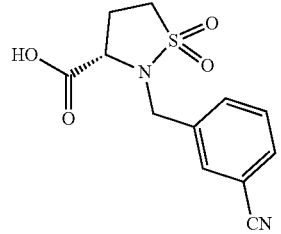 [SMILES: N#Cc1cccc(CN2[C@H](C(=O)O)CCS2(=O)=O)c1]

Referring to Step B in Example 11, the target product was obtained with a yield of 75%.

$^1$H-NMR (400 MHz, CDCl$_3$): δ=7.81 (s, 1H), 7.77-7.54 (m, 3H), 4.35 (s, 2H), 3.98-3.96 (m, 1H), 3.38-3.26 (m, 2H), 2.66-2.50 (m, 1H), 2.49-2.26 (m, 1H).

Step C: (S)—N-(1-(2-chlorophenyl)-2-(cyclohexylamino)-2-oxoethyl)-2-(3-cyanophenylethyl)-N-(3-fluorophenyl)-isothiazolidine-3-carboxamide 1,1-dioxide

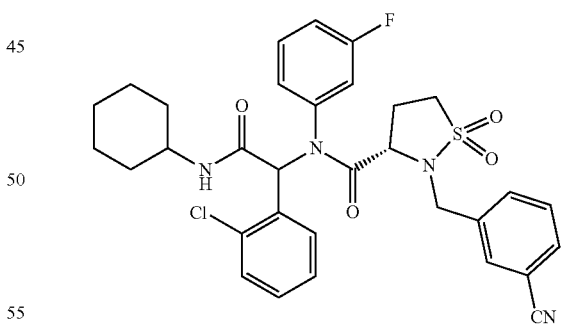

Referring to Step E in Example 1, the title compound was obtained with a yield of 79%.

$^1$H-NMR (400 MHz, CDCl$_3$): δ=7.80-6.75 (m, 12H), 6.41 and 6.37 (s, 0.5 and 0.5H), 5.41 and 5.35 (m, 0.5 and 0.5H), 4.62 and 4.53 (d, J=16, 0.5 and 0.5H), 4.15 and 4.04 (d, J=15.2, 16, 0.5 and 0.5H), 3.96-3.78 (m, 1H), 3.65-3.60 (m, 1H), 3.45-3.40 (m, 1H), 3.18-3.02 (m, 1H), 2.40-2.20 (m, 2H), 2.02-1.80 (m, 2H), 1.79-1.45 (m, 4H), 1.40-1.02 (m 4H).

m/z=623 [M+H]$^+$.

Example 22: (S)—N—((R)-1-(2-chlorophenyl)-2-((4,4-difluorocyclohexyl)amino))-2-oxoethyl)-2-(4-cyanopyridin-2-yl)-N-(3-fluorophenyl)-isothiazolidine-3-carboxamide 1,1-dioxide

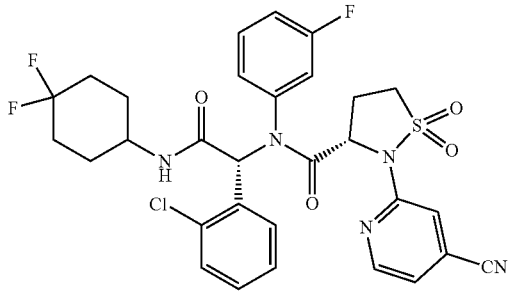 [SMILES: N#Cc1ccnc(N2[C@H](C(=O)N(c3cccc(F)c3)[C@@H](C(=O)NC3CCC(F)(F)CC3)c3ccccc3Cl)CCS2(=O)=O)c1]

Step A: (3S)—N-(1-(2-chlorophenyl)-2-((4,4-difluorocyclohexyl)amino)-2-oxoethyl)-N-(3-fluorophenyl)isothiazolidine-3-carboxamide 1,1-dioxide

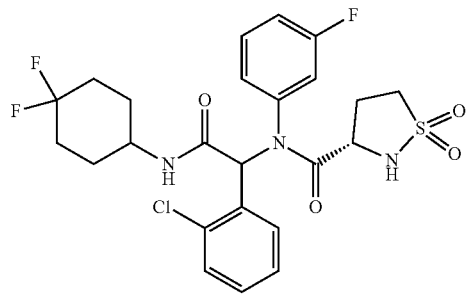 [SMILES: O=C(NC1CCC(F)(F)CC1)C(c1ccccc1Cl)N(C(=O)[C@@H]1CCS(=O)(=O)N1)c1cccc(F)c1]

Under stirring at room temperature, in MeOH (6.0 mL), 2-chloro-benzaldehyde (85 mg, 0.605 mmol) and 3-fluoroaniline (67 mg, 0.605 mmol) were mixed for 30 min. (S)-isothiazolinone-3-carboxylic acid 1,1-dioxide (150 mg, 0.908 mmol) was added and the reaction mixture was stirred for 10 min, followed by adding 1,1-difluoro-4-isocyanocyclohexane (88 mg, 0.605 mmol), and stirring overnight at room temperature. The solvent was removed under vacuum. (3S)—N-(1-(2-chlorophenyl)-2-((4,4-difluorocyclohexyl)amino)-2-oxoethyl)-N-(3-fluorophenyl)isothiazolidine-3-carboxamide 1,1-dioxide (114 mg, yield 34.7%), which was directly used in the next step, was obtained by isolating through silica gel column chromatography.
m/z=544 [M+H]$^+$.

Step B: (S)—N—((R)-1-(2-chlorophenyl)-2-((4,4-difluorocyclohexyl)amino))-2-oxoethyl)-2-(4-cyanopyridin-2-yl)-N-(3-fluorophenyl)-isothiazolidine-3-carboxamide 1,1-dioxide

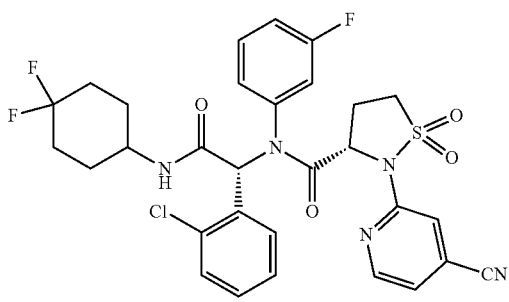 [SMILES: N#Cc1ccnc(N2[C@H](C(=O)N(c3cccc(F)c3)[C@@H](C(=O)NC3CCC(F)(F)CC3)c3ccccc3Cl)CCS2(=O)=O)c1]

(3S)—N-(1-(2-chlorophenyl)-2-((4,4-difluorocyclohexyl)amino)-2-oxoethyl)-N-(3-fluorophenyl)isothiazolidine-3-carboxamide 1,1-dioxide (114 mg, 0.210 mmol), 2-bromo-4-cyanopyridine (47 mg, 0.252 mmol), cuprous iodide (21 mg, 0.11 mmol), N,N'-dimethylethylenediamine (19 mg, 0.21 mmol) and cesium carbonate (206 mg, 0.63 mmol) were added into a sealed tube reactor, dioxane (8 mL) was added thereto, nitrogen gas was introduced thereto for 5 min, the tube was sealed and the reaction was carried out at 80° C. overnight. After the solvent was removed, the column chromatography (PE:EA=1:1) was performed to give a racemic product, which was then subjected to thin layer chromatography (DCM:EA=8:1), so as to give the pure chiral compound (S)—N—((R)-1-(2-chlorophenyl)-2-((4,4-difluorocyclohexyl)amino))-2-oxoethyl)-2-(4-cyanopyridin-2-yl)-N-(3-fluorophenyl)-isothiazolidine-3-carboxamide 1,1-dioxide (39 mg, yield 28.7%).

$^1$H-NMR (400 MHz, CDCl$_3$): δ=8.55 (d, J=4.7 Hz, 1H), 7.67 (s, 1H), 7.39 (d, J=7.7 Hz, 1H), 7.33-7.18 (m, 5H), 7.07 (dd, J=24.5, 16.7 Hz, 2H), 6.95-6.69 (m, 1H), 6.10 (s, 1H), 5.70 (d, J=5.6 Hz, 1H), 4.76 (d, J=6.9 Hz, 1H), 3.72-3.70 (m, 2H), 3.36-3.31 (m, 1H), 2.58-2.54 (m, 2H), 2.07-1.64 (m, 5H), 1.41-1.17 (m, 3H).

m/z=646 [M+H]$^+$.

Example 23: (S)—N—((S)-1-(2-chlorophenyl)-2-((4,4-difluorocyclohexyl)amino)-2-oxoethyl)-2-(4-cyanopyridin-2-yl)-N-(3-fluorophenyl)-isothiazolidine-3-carboxamide 1,1-dioxide

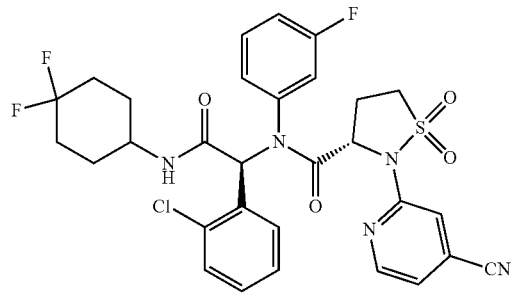 [SMILES: N#Cc1ccnc(N2[C@H](C(=O)N(c3cccc(F)c3)[C@H](C(=O)NC3CCC(F)(F)CC3)c3ccccc3Cl)CCS2(=O)=O)c1]

In Step B of Example 22, (S)—N—((S)-1-(2-chlorophenyl)-2-((4,4-difluorocyclohexyl)amino)-2-oxoethyl)-2-(4-cyanopyridin-2-yl)-N-(3-fluorophenyl)-isothiazolidine-3-carboxamide 1,1-dioxide (40 mg, yield 29.4%) was obtained by isolating through thin layer chromatography.

$^1$H-NMR (400 MHz, CDCl$_3$): δ=8.46 (s, 1H), 7.71-7.68 (m, 2H), 7.33 (d, J=13.3 Hz, 1H), 7.08-7.01 (m, 6H), 6.45 (s, 1H), 5.43 (d, J=7.6 Hz, 1H), 4.81 (d, J=7.2 Hz, 1H), 3.98-3.93 (m, 1H), 3.75-3.70 (m, 1H), 3.34 (s, 1H), 2.63 (s, 1H), 2.46 (s, 1H), 2.11-2.05 (m, 4H), 1.89-1.81 (m, 2H), 1.63-1.35 (m, 2H), 0.88 (s, 1H).

m/z=646 [M+H]$^+$.

Example 24: (S)—N—((S)-1-(2-chlorophenyl)-2-((3,3-difluorocyclobutyl)amino)-2-oxoethyl)-2-(4-cyanopyridin-2-yl)-N-(3-fluorophenyl)-1,2,5-thiadiazolidine-3-carboxamide 1,1-dioxide

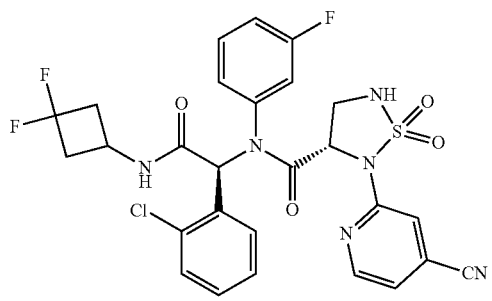 [SMILES: N#Cc1ccnc(N2[C@H](C(=O)N(c3cccc(F)c3)[C@H](C(=O)NC3CC(F)(F)C3)c3ccccc3Cl)CNS2(=O)=O)c1]

Step A: methyl (S)-2-(benzylamino)-3-hydroxypropionate

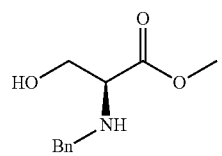

Under stirring at room temperature, benzaldehyde (13.6 g, 128.6 mmol) and anhydrous sodium sulfate (6.0 g) were added into a 500 mL round-bottomed flask, which contained a solution of the mixture of L-serine methyl ester hydrochloride (20 g, 128.6 mmol) and triethylamine (13 g, 128.6 mmol) in dichloromethane. They were stirred to react overnight at room temperature. After the reaction was completed, it was filtered and concentrated. The concentrated residue was dissolved by adding methanol, and sodium borohydride (4.86 g, 128.6 mmol) was carefully added in portions under an ice bath. They were reacted for 1 hour at room temperature. Methanol was removed, and it was diluted with dichloromethane, washed with saturated aqueous solution of sodium bicarbonate, extracted with dichloromethane for three times. The combined organic phase was washed with brine, dried over sodium sulfate, filtered and concentrated under vacuum. Methyl (S)-2-(benzylamino)-3-hydroxypropionate (20.6 g, yield 77%) was obtained.

$^1$H-NMR (400 MHz, CDCl$_3$): δ=7.38-7.26 (m, 5H), 4.48 (d, J=12.8 Hz, 1H), 3.8-3.72 (m, 6H), 3.61 (dd, J=10.8, 10.8 Hz, 1H), 3.54 (dd, J=6.8, 6.4 Hz, 1H).

Step B: methyl (S)-2-(benzyl(N-(tert-butoxycarbonyl)sulfonyl)amino)-3-hydroxypropionate

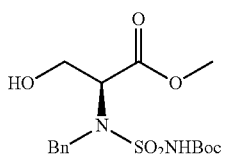

Under stirring in an ice bath, triethylamine (7.25 g, 71.69 mmol) and tert-butyl chlorosulfonyl carbamate (10.3 g, 47.79 mmol) were added into a solution of methyl (S)-2-(benzylamino)-3-hydroxypropionate (10.0 g, 47.79 mmol) in dichloromethane. They were reacted with stirring overnight at room temperature. After the reaction was completed, it was diluted by adding dichloromethane, quenched by adding water, extracted with dichloromethane for three times. The combined organic phase was washed with brine, dried over sodium sulfate, filtered and concentrated under vacuum. Methyl (S)-2-(benzyl(N-(tert-butoxycarbonyl)sulfonyl)amino)-3-hydroxypropionate (6.43 g, yield 35%) was obtained by isolating through column chromatography.

$^1$H-NMR (400 MHz, CDCl$_3$): δ=7.44-7.28 (m, 6H), 4.67 (dd, J=14.3, 6.1 Hz, 2H), 4.56 (d, J=15.6 Hz, 1H), 4.00 (d, J=7.2 Hz, 2H), 3.69 (s, 3H), 2.84 (s, 1H), 1.48 (s, 9H).

Step C: (S)-2-tert-butyl-4-methyl-5-benzyl-1,2,5-thiadiazolidine-2,4-dicarboxylate 1,1-dioxide

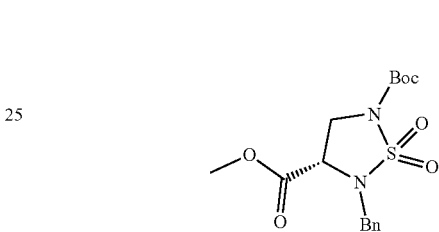

Under stirring in an ice bath, DIAD (4.0 g, 19.84 mmol) was added into a solution of methyl (S)-2-(benzyl(N-(tert-butoxycarbonyl)sulfonyl)amino)-3-hydroxypropionate (6.42 g, 16.54 mmol) and triphenylphosphine (5.2 g, 19.84 mmol) in dichloromethane. They were reacted for 2 h at room temperature. After the reaction was completed, it was diluted with dichloromethane, quenched with water, extracted with dichloromethane for three times. The combined organic phase was washed with brine, dried over sodium sulfate, filtered and concentrated under vacuum. The target compound (5.77 g, yield 94.3%) was obtained by isolating through column chromatography.

$^1$H-NMR (400 MHz, CDCl$_3$): δ=7.43-7.28 (m, 5H), 4.54 (d, J=14.4 Hz, 1H), 4.44 (d, J=14.4 Hz, 1H), 4.07-4.00 (m, 1H), 3.89 (t, J=2.9 Hz, 2H), 3.72 (s, 3H), 1.55 (s, 9H).

Step D: (S)-2-tert-butyl 4-methyl-1,2,5-thiadiazolidine-2,4-dicarboxylate 1,1-dioxide

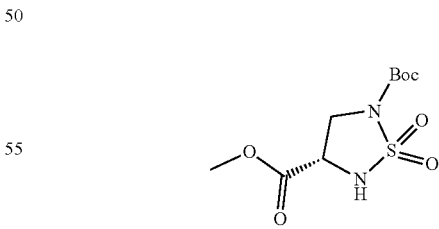

Under stirring at room temperature, 10 wt % palladium carbon (10 g) was added into a solution of (S)-2-tert-butyl-4-methyl-5-benzyl-1,2,5-thiadiazolidine-2,4-dicarboxylate 1,1-dioxide in dichloromethane (2.97 g, 8.02 mmol). The gas was exchanged 10 times by circulating water pump. Under the protection of hydrogen gas, they were reacted overnight at room temperature. After the reaction was completed, it was filtered and concentrated. (S)-2-tert-butyl 4-methyl-1,2,5-thiadiazolidine-2,4-dicarboxylate 1,1-dioxide (1.49 g, yield 66%) was obtained by isolating through column chromatography.

¹H-NMR (400 MHz, CDCl₃): δ=5.17 (d, J=8.4 Hz, 1H), 4.39 (dd, J=16, 7.6 Hz, 1H), 4.18 (dd, J=10.0, 2.4 Hz, 1H), 3.88-3.83 (m, 4H), 1.52 (s, 9H).

Step E: (S)-5-(tert-butoxycarbonyl)-1,2,5-thiadiazolidine-3-carboxylic acid 1,1-dioxide

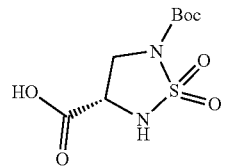 [SMILES: CC(C)(C)OC(=O)N1C[C@@H](C(=O)O)NS1(=O)=O]

Under stirring in an ice bath, lithium hydroxide monohydrate (342 mg, 14.27 mmol) was added to a solution of (S)-2-tert-butyl 4-methyl-1,2,5-thiadiazolidine-2,4-dicarboxylate 1,1-dioxide (800 mg, 2.854 mmol) in 10 mL methanol/water (the volume ratio being 5/1). They were reacted overnight at room temperature. After the reaction was completed, methanol was removed by rotary evaporation. The system was adjusted to a pH less than 3 with 4N HCl and extracted with ethyl acetate for three times. The combined organic phase was washed with brine, dried over sodium sulfate, filtered and concentrated under vacuum. (S)-5-(tert-butoxycarbonyl)-1,2,5-thiadiazolidine-3-carboxylic acid 1,1-dioxide (759 mg, yield 100%) was obtained by isolating through column chromatography.

¹H-NMR (400 MHz, CDCl₃): δ=5.39-5.33 (m, 1H), 4.46 (s, 1H), 4.23 (dd, J=10, 5.6 Hz, 1H), 3.98 (dd, J=9.6, 7.6 Hz, 1H), 1.50 (s, 9H).

Step F: (3S)—N-(1-(2-chlorophenyl)-2-((3,3-difluorocyclobutyl)amino)-2-oxoethyl)-N-(3-fluorophenyl)-5-tert-butoxycarbonyl-1,2,5-thiadiazolidine-3-carboxamide 1,1-dioxide

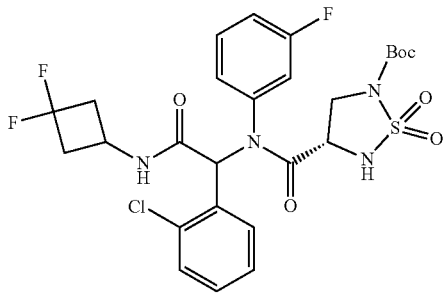 [SMILES: CC(C)(C)OC(=O)N1C[C@@H](C(=O)N(c2cccc(F)c2)C(C(=O)NC2CC(F)(F)C2)c2ccccc2Cl)NS1(=O)=O]

Under stirring at room temperature, in MeOH (6.0 mL), 2-chloro-benzaldehyde (400 mg, 2.85 mmol) and 3-fluoroaniline (317 mg, 2.85 mmol) were mixed and stirred for 30 min. (S)-5-(tert-butoxycarbonyl)-1,2,5-thiadiazolidine-3-carboxylic acid 1,1-dioxide (759 mg, 2.85 mmol) was added thereto and the reaction mixture was stirred for 10 min. Then, 1,1-difluoro-4-isocyanocyclobutane (333 mg, 2.85 mmol) was added thereto and the reaction mixture was stirred overnight at room temperature. The solvent was removed under vacuum. (3S)—N-(1-(2-chlorophenyl)-2-((3,3-difluorocyclobutyl)amino)-2-oxoethyl)-N-(3-fluorophenyl)-5-tert-butoxycarbonyl-1,2,5-thiadiazolidine-3-carboxamide 1,1-dioxide (578 mg, yield 32.9%) was obtained by isolating through column chromatography.

m/z=617 [M+H]⁺.

Step G: (3S)—N-(1-(2-chlorophenyl)-2-((3,3-difluorocyclobutyl)amino)-2-oxoethyl)-2-(4-cyanopyridin-2-yl)-N-(3-fluorophenyl)-5-tert-butoxycarbonyl-1,2,5-thiadiazolidine-3-carboxamide 1,1-dioxide

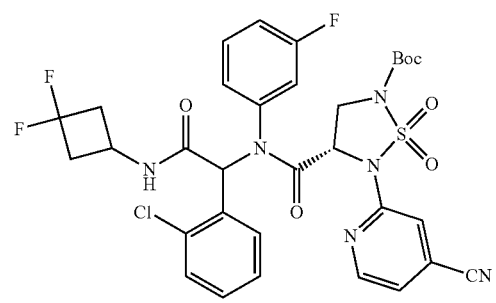

(3S)—N-(1-(2-chlorophenyl)-2-((3,3-difluorocyclobutyl)amino)-2-oxoethyl)-N-(3-fluorophenyl)-5-tert-butoxycarbonyl-1,2,5-thiadiazolidine-3-carboxamide 1,1-dioxide (570 mg, 0.924 mmol), 2-bromo-4-cyanopyridine (186 mg, 1.10 mmol), cuprous iodide (88 mg, 0.462 mmol), N,N'-dimethylethylenediamine (82 mg, 0.924 mmol) and cesium carbonate (903 mg, 2.772 mmol) were added into a sealed tube reactor, dioxane (8 mL) was added thereto, nitrogen gas was introduced thereto for 5 min and the tube was sealed to react overnight at 80° C. The solvent was removed. (3S)—N-(1-(2-chlorophenyl)-2-((3,3-difluorocyclobutyl)amino)-2-oxoethyl)-2-(4-cyanopyridin-2-yl)-N-(3-fluorophenyl)-5-tert-butoxycarbonyl-1,2,5-thiadiazolidine-3-carboxamide 1,1-dioxide (190 mg, yield 28.6%) was obtained by column chromatography (PE:EA=1:1).

m/z=719 [M+H]⁺.

Step H: (S)—N—((S)-1-(2-chlorophenyl)-2-((3,3-difluorocyclobutyl)amino)-2-oxoethyl)-2-(4-cyanopyridin-2-yl)-N-(3-fluorophenyl)-1,2,5-thiadiazolidine-3-carboxamide 1,1-dioxide

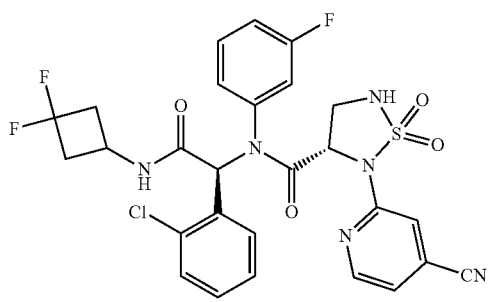 [SMILES: N#Cc1ccnc(N2[C@H](C(=O)N(c3cccc(F)c3)[C@H](C(=O)NC3CC(F)(F)C3)c3ccccc3Cl)CNS2(=O)=O)c1]

Under stirring in an ice bath, trifluoroacetic acid (2.0 mL) was added into a solution of (3S)—N-(1-(2-chlorophenyl)-2-((3,3-difluorocyclobutyl)amino)-2-oxoethyl)-2-(4-cyanopyridin-2-yl)-N-(3-fluorophenyl)-5-tert-butoxycarbonyl-1,2,5-thiadiazolidine-3-carboxamide 1,1-dioxide (190 mg, 0.264 mmol) in dichloromethane. Under the protection of nitrogen gas, they were reacted overnight at room temperature. After the reaction was completed, it was concentrated. (S)—N—((S)-1-(2-chlorophenyl)-2-((3,3-difluorocyclobutyl)amino)-2-oxoethyl)-2-(4-cyanopyridin-2-yl)-N-(3-fluorophenyl)-1,2,5-thiadiazolidine-3-carboxamide 1,1-dioxide (7 mg, yield 4.3%) was obtained by isolating through column chromatography.

¹H-NMR (400 MHz, CDCl₃): δ=8.43 (t, J=5.6 Hz, 1H), 7.63 (d, J=8.1 Hz, 1H), 7.56 (s, 1H), 7.40-7.27 (m, 2H), 7.18 (d, J=6.1 Hz, 2H), 7.10-6.83 (m, 4H), 6.47 (d, J=6.7 Hz, 1H), 6.04 (d, J=6.3 Hz, 1H), 5.74 (d, J=28.7 Hz, 1H), 4.83 (s, 1H), 4.25 (d, J=39.4 Hz, 1H), 3.77 (d, J=9.7 Hz, 1H), 3.68-3.46 (m, 1H), 3.17-2.90 (m, 2H), 2.45 (m, 2H).

m/z=619 [M+H]⁺.

Example 25: (3S)—N-(1-(2-chlorophenyl)-2-((3,3-difluorocyclobutyl)amino)-2-oxoethyl)-2-(4-cyanopyridin-2-yl)-N-(3-fluorophenyl)-5-methyl-1,2,5-thiadiazolidine-3-carboxamide 1,1-dioxide

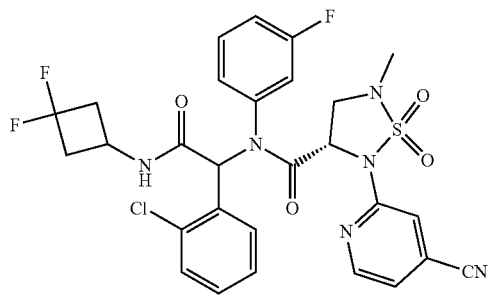

Step A: methyl (S)-2-benzyl-1,2,5-thiadiazolidine-3-carboxylate 1,1-dioxide

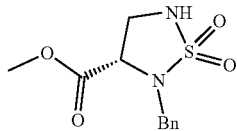 [SMILES: COC(=O)[C@@H]1CNS(=O)(=O)N1Cc1ccccc1]

Under stirring in an ice bath, trifluoroacetic acid (15.0 mL) was added into a solution of (S)-2-tert-butyl 4-methyl-5-benzyl-1,2,5-thiadiazolidine-2,4-dicarboxylate 1,1-dioxide (2.8 g, 7.559 mmol) in dichloromethane. Under the protection of nitrogen gas, they were reacted overnight at room temperature. After the reaction was completed, it was concentrated. Methyl (S)-2-benzyl-1,2,5-thiadiazolidine-3-carboxylate 1,1-dioxide (1.54 g, yield 75.5%) was obtained by isolating through column chromatography.

Step B: methyl (S)-2-benzyl-5-methyl-1,2,5-thiadiazolidine-3-carboxylate 1,1-dioxide

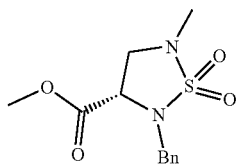 [SMILES: COC(=O)[C@@H]1CN(C)S(=O)(=O)N1Cc1ccccc1]

Under stirring at room temperature, methyl iodide (629 mg, 4.44 mmol) was added to a solution of methyl (S)-2-benzyl-1,2,5-thiadiazolidine-3-carboxylate 1,1-dioxide (600 mg, 2.22 mmol) and potassium carbonate (920 mg, 6.66 mmol) in DMF (6 mL). Under the protection of nitrogen gas, they were reacted overnight at room temperature. After the reaction was completed, it was diluted with ethyl acetate, quenched by adding water and extracted with ethyl acetate for three times. The combined organic phase was washed with brine, dried over sodium sulfate, filtered and concentrated under vacuum. Methyl (S)-2-benzyl-5-methyl-1,2,5-thiadiazolidine-3-carboxylate 1,1-dioxide (616 mg, yield 97.6%) was obtained by isolating through column chromatography.

¹H-NMR (400 MHz, CDCl₃): δ=7.40-7.31 (m, 5H), 4.48 (d, J=1.2 Hz, 2H), 3.86 (dd, J=8, 7.6 Hz, 1H), 3.66 (s, 3H), 3.54 (dd, J=10, 9.6 Hz, 1H), 3.35 (dd, J=10, 10 Hz, 1H), 2.77 (s, 3H).

Step C: methyl (S)-5-methyl-1,2,5-thiadiazolidine-3-carboxylate 1,1-dioxide

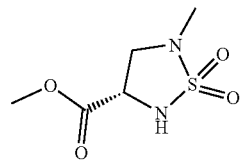

Under stirring at room temperature, 10 wt % palladium carbon (300 mg) was added into a solution of methyl (S)-2-benzyl-5-methyl-1,2,5-thiadiazolidine-3-carboxylate 1,1-dioxide (616 mg, 2.166 mmol) in dichloromethane. The gas was exchanged 10 times by circulating water pump. Under the protection of hydrogen gas, they were reacted overnight at room temperature. After the reaction was completed, it was filtered and concentrated. Methyl (S)-5-methyl-1,2,5-thiadiazolidine-3-carboxylate 1,1-dioxide (342 mg, yield 81.4%) was obtained by isolating through column chromatography.

¹H-NMR (400 MHz, CDCl₃): δ=5.19-5.13 (m, 1H), 4.26-4.20 (m, 1H), 3.88 (s, 3H), 3.63 (dd, J=10.4, 10.0 Hz, 1H), 3.55 (dd, J=10.0, 10.0 Hz, 1H), 2.72 (s, 3H).

Step D: (S)-5-methyl-1,2,5-thiadiazolidine-3-carboxylic acid 1,1-dioxide

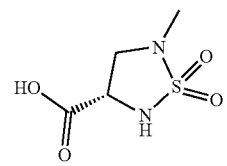

Under stirring in an ice bath, lithium hydroxide monohydrate (210 mg, 8.755 mmol) was added to a solution of methyl (S)-5-methyl-1,2,5-thiadiazolidine-3-carboxylate 1,1-dioxide (340 mg, 1.751 mmol) in 10 mL methanol/water (the volume ratio being 5/1). They were reacted overnight at room temperature. After the reaction was completed, methanol was removed by rotary evaporation. The system was adjusted to a pH less than 3 with 4N HCl and extracted with ethyl acetate for three times. The combined organic phase was washed with bine, dried over sodium sulfate, filtered and concentrated under vacuum. (S)-5-methyl-1,2,5-thiadiazolidine-3-carboxylic acid 1,1-dioxide (315 mg, yield 100%) was obtained by isolating through column chromatography.

Step E: (3S)—N-(1-(2-chlorophenyl)-2-((3,3-difluorocyclobutyl)amino)-2-oxoethyl)-N-(3-fluorophenyl))-5-methyl-1,2,5-thiadiazolidine-3-carboxamide 1,1-dioxide

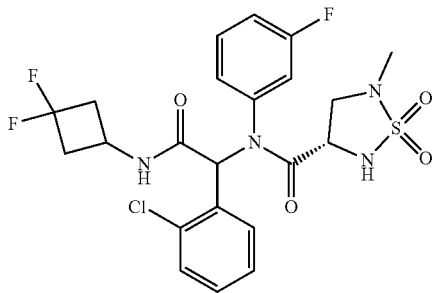 [SMILES: CN1C[C@@H](C(=O)N(c2cccc(F)c2)C(C(=O)NC2CC(F)(F)C2)c2ccccc2Cl)NS1(=O)=O]

Under stirring at room temperature, 2-chloro-benzaldehyde (156 mg, 1.11 mmol) and 3-fluoroaniline (124 mg, 1.11 mmol) were mixed in MeOH (6.0 mL) for 30 min. (S)-5-methyl-1,2,5-thiadiazolidine-3-carboxylic acid 1,1-dioxide (200 mg, 1.11 mmol) was added thereto and the reaction mixture was stirred for 10 min. Then, 1,1-difluoro-4-isocyanocyclobutane (130 mg, 1.11 mmol) was added thereto and the reaction mixture was stirred overnight at room temperature. The solvent was removed under vacuum. (3S)—N-(1-(2-chlorophenyl)-2-((3,3-difluorocyclobutyl)amino)-2-oxoethyl)-N-(3-fluorophenyl))-5-methyl-1,2,5-thiadiazolidine-3-carboxamide 1,1-dioxide (240 mg, yield 41.0%) was obtained by isolating through silica gel column chromatography.

¹H-NMR (400 MHz, CDCl3): δ=7.63-7.57 (m, 1H), 7.42 (d, J=8.0 Hz, 0.5H), 7.32 (d, J=7.6 Hz, 0.5H), 7.29-7.20 (m, 1H), 7.14-6.92 (m, 4H), 6.78-6.6 (m, 1H), 6.55 (s, 0.5H), 6.34 (s, 0.5H), 6.14 (d, J=6.4 Hz, 0.5H), 6.01 (d, J=6.4 Hz, 0.5H), 5.72-5.52 (m, 1H), 4.35-4.29 (m, 1H), 4.20-4.06 (m, 1H), 3.56-3.41 (m, 1H), 3.09-2.80 (m, 3H), 2.66 (s, 3H), 2.61-2.31 (m, 2H).

m/z=531 [M+H]⁺.

Step F: (3S)—N-(1-(2-chlorophenyl)-2-((3,3-difluorocyclobutyl)amino)-2-oxoethyl)-2-(4-cyanopyridin-2-yl)-N-(3-fluorophenyl)-5-methyl-1,2,5-thiadiazolidine-3-carboxamide 1,1-dioxide

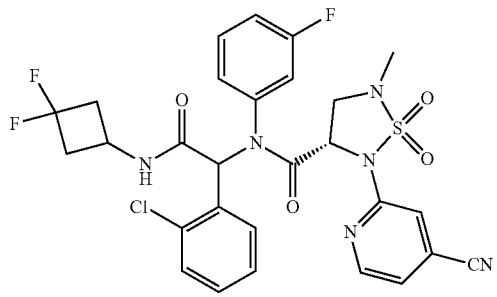 [SMILES: CN1C[C@@H](C(=O)N(c2cccc(F)c2)C(C(=O)NC2CC(F)(F)C2)c2ccccc2Cl)N(c2cc(C#N)ccn2)S1(=O)=O]

(3S)—N-(1-(2-chlorophenyl)-2-((3,3-difluorocyclobutyl)amino)-2-oxoethyl)-N-(3-fluorophenyl))-5-methyl-1,2,5-thiadiazolidine-3-carboxamide 1,1-dioxide (140 mg, 0.264 mmol), 2-bromo-4-cyanopyridine (91 mg, 0.291 mmol), cuprous iodide (50 mg, 0.132 mmol), N,N'-dimethylethylenediamine (42 mg, 0.264 mmol) and cesium carbonate (441 mg, 0.792 mmol) were added into a sealed tube reactor, dioxane (8 mL) was added thereto, nitrogen gas was introduced thereto for 5 min and the tube was sealed to react overnight at 80° C. The solvent was removed. (3S)—N-(1-(2-chlorophenyl)-2-((3,3-difluorocyclobutyl)amino)-2-oxoethyl)-2-(4-cyanopyridin-2-yl)-N-(3-fluorophenyl)-5-methyl-1,2,5-thiadiazolidine-3-carboxamide 1,1-dioxide (81 mg, yield 48.5%) was obtained through column chromatography (PE:EA=1:1).

¹H-NMR (400 MHz, CDCl₃): δ=8.55-8.47 (m, 1H), 7.90-7.65 (m, 1H), 7.51 (d, J=5.2 Hz, 0.5H), 7.34 (d, J=6.4 Hz, 0.5H), 7.29-7.16 (m, 4H), 7.14 (m, 4H), 6.75-6.70 (m, 1H), 6.55 (d, J=4.4 Hz, 1H), 6.16 (d, J=12 Hz, 1H), 4.95-4.73 (m, 1H), 4.19-4.11 (m, 1H), 3.53-3.44 (m, 1H), 3.34 (t, J=7.8 Hz, 1H), 3.0-2.81 (m, 4H), 2.41-2.31 (m, 2H).

m/z=633 [M+H]⁺.

Example 26: (3S)—N-(1-(2-chlorophenyl)-2-(cyclohexylamino)-2-oxoethyl)-2-(4-cyanopyridin-2-yl)-N-(3-aminosulfonylphenyl)-isothiazolidine-3-carboxamide 1,1-dioxide

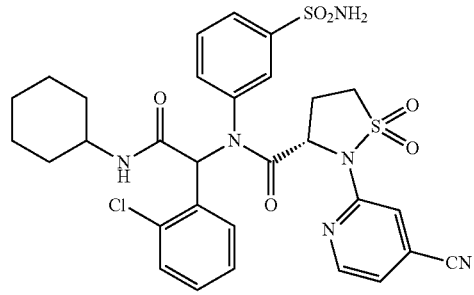 [SMILES: N#Cc1ccnc(N2[C@H](C(=O)N(c3cccc(S(N)(=O)=O)c3)C(C(=O)NC3CCCCC3)c3ccccc3Cl)CCS2(=O)=O)c1]

Referring to Step E in Example 1, the reaction materials 2,2-difluorocyclobutyl isocyanide, 3-amino-5-fluoropyridine and (S)-isothiazolidine-3-carboxylic acid 1,1-dioxide were replaced with cyclohexyl isocyanide, 3-aminobenzenesulfonamide and (S)-2-(4-cyanopyridin-2-yl)isothiazolidine-3-carboxylic acid 1,1-dioxide (prepared in Step B of Example 11), respectively. The title compound was obtained with a yield of 36%.

¹H-NMR (400 MHz, CDCl₃): δ=8.58 (d, J=5.0 Hz, 1H), 8.14-6.84 (m, 12H), 6.52 (s, 1H), 5.53 (m, 1H), 4.76 (m, 1H), 3.88-3.78 (m, 1H), 3.80-3.65 (m, 1H), 3.39-3.36 (m, 1H), 2.69-2.63 (m, 1H), 2.50-2.42 (m, 1H), 1.95-1.90 (m, 2H), 1.74-1.59 (m, 4H), 1.38-1.24 (m, 2H), 1.17-0.94 (m, 2H).

m/z=671 [M+H]⁺.

Example 27: 3-((S)—N—((S)-1-(2-chlorophenyl)-2-((3,3-difluorocyclobutyl)amino)-2-oxoethyl)-2-(4-cyanopyridin-2-yl)-1,1-dioxoisothiazolidine-3-carboxamido)-5-fluoropyridine-1-oxide

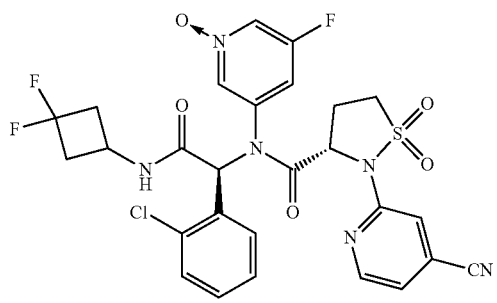 [SMILES: N#Cc1ccnc(N2[C@H](C(=O)N(c3cc(F)c[n+]([O-])c3)[C@H](C(=O)NC3CC(F)(F)C3)c3ccccc3Cl)CCS2(=O)=O)c1]

(S)—N—((S)-1-(2-chlorophenyl)-2-((3,3-difluorocyclobutyl)amino)-2-oxoethyl)-2-(4-cyanopyridin-2-yl)-N-(5-fluoropyridin-3-yl)-isothiazolidine-3-carboxamide 1,1-dioxide (50 mg, 0.081 mmol, prepared in Example 2) and 3-chloroperoxybenzoic acid (28 mg, 0.16 mmol) were added to dichloromethane (10 mL) and they were stirred overnight at room temperature. The solvent was removed by vacuum concentration, and the residue was isolated by silica gel thin layer chromatography (EA) to give 3-((S)—N—((S)-1-(2-chlorophenyl)-2-((3,3-difluorocyclobutyl)amino)-2-oxoethyl)-2-(4-cyanopyridin-2-yl)-1,1-dioxoisothiazolidine-3-carboxamido)-5-fluoropyridine-1-oxide (22 mg, yield 43%).

$^1$H-NMR (400 MHz, CDCl$_3$): δ 8.72 (s, 0.5H), 8.13 (s, 0.5H), 8.48-8.41 (m, 1H), 7.94 (s, 1H), 7.80-7.68 (m, 1H), 7.41 (d, J=8.0 Hz, 1H), 7.26-7.15 (m, 4H), 7.05-6.95 (m, 1H), 6.49 (s, 1H), 6.01 (s, 0.5H), 5.90 (s, 0.5H), 4.86-4.82 (m, 1H), 4.34 (s, 1H), 3.78-3.68 (m, 1H), 3.45-3.35 (m, 1H), 3.10-3.00 (m, 2H), 2.61-2.38 (m, 4H).

m/z=635 [M+H]$^+$.

Bioactivity Experiments

Enzyme Assay:

Resazurin is a traditional redox dye, and after a redox reaction, it can be reduced from a blue resazurin without fluorescence to a pink fluorescent substance, resorufin, which can be measured and quantified with relative fluorescence unit (RFU) of fluorophotometer ($E_x$=530-570 nm, Em=590-620 nm). At present, resazurin is widely used for determining the viability of bacteria, cells, etc. and the enzyme activity detection of oxidoreductase. We detected the decrease of cofactor NADPH to determine the inhibitory activity of a compound against IDH1m and detected the generation of cofactor NADPH to determine the inhibitory activity of a compound against IDH WT. The compound was pre-incubated with IDH1m and NADPH, and then the reaction was initiated by adding α-KG and performed for certain time under a linear condition. Then, diaphorase (lipoamide dehydrogenase) and the corresponding substrate resazurin were added thereto for detection. Lipoamide dehydrogenase terminated the IDH1m reaction by decreasing the available cofactor NADPH, which oxidized NADPH to NADP, and reduced resazurin to high fluorescent resorufin. The amount of the remaining cofactor NADPH after a specific reaction time was quantified via an easily detectable fluorophore.

The compound was pre-incubated with IDH-WT and NADP, and then the reaction was initiated by adding isocitric acid, diaphorase (lipoamide dehydrogenase) and the corresponding substrate resazurin, and performed for certain time under a linear condition, and followed by detecting the amount of fluorescent substance. NADP was reduced to NADPH in this experiment, and the latter reduced resazurin to high fluorescent resorufin under the action of lipoamide dehydrogenase. The amount of the generated cofactor NADPH after a specific reaction time was quantified via a detectable fluorophore, so as to calculate the inhibitory effect of the compound on IDH-WT.

The specific operation was as follows: 2.5 μl of the compound diluted in a 3-fold gradient was added to a 384-well plate, followed by adding 5 μl of the reaction buffer (20 mM Tris-HCl, pH 7.5; 150 mM NaCl; 10 mM MgCl$_2$; 0.4 mg/mL BSA (Bovine Serum Albumin) and 2 mM DTT (dithiothreitol)) containing 40 nM IDH1 (R132H/R132C) and 20 μM NADPH. Then, the above test mixture was incubated at 23° C. for 16 hours, and then 2.5 μl of the reaction buffer containing 4 mM α-KG was added to initiate the reaction. After they were incubated for 60 minutes at room temperature, 5 μl of the termination mixture (0.4 U/ml diaphorase and 20 μM resazurin) formulated with the reaction buffer was added to convert resazurin to resorufin, so as to measure the amount of the remaining NADPH. After incubating at 23° C. for 10 minutes, fluorescence values were determined through Flexstation 3 at Ex535/Em595. The enzyme activity of each compound was respectively determined at 12 concentrations, and the data were calculated using the software GraFit6.0 (Erithacus Software) to obtain the IC$_{50}$ value of each compound.

2-HG Determination:

In the presence of 2-HG, phosphoglycerate dehydrogenase PHGDH can reduce NAD to NADPH, and the latter may be quantitatively determined by lipoamide dehydrogenase and the substrate thereof, resazurin.

HT-1080 cell is a human fibrosarcoma cell line with an IDH1 mutation (R132C). U87 cell is a human glioblastoma cell line with an IDH1 mutation (R132H). They were cultured in RPMI-1640 medium supplemented with 10% fetal bovine serum, 100 units/mL penicillin and 0.1 mg/mL streptomycin.

Cells was digested with trypsin, and inoculated into a 6-well plate at a density of 5×10$^5$, and cultured overnight in an incubator at 37° C. Next day, the test compound was added (the final concentration of DMSO is 0.1%) thereto and cultured for another 24 hours. Culture medium of each sample was sucked out and centrifuged at 1000 rpm for 10 min. The supernatant was sucked out to detect the content of 2-HG therein. Additionally, cells were washed with PBS (phosphate buffered saline), digested with trypsin and collected. After the collected cells were washed with PBS for one time, the determination of intracellular 2-HG content was performed.

The method for determining the intracellular 2-HG was as follows: cells were re-suspended with 300 μL reaction buffer (40 mM Tris-HCl, pH 8.5; 150 mM NaCl) and disrupted by ultrasonication. They were centrifuged for 10 min at 12,000 rpm and 4° C. to remove insoluble substances. 25 μL supernatant was sucked out to determine the protein concentration by a BCA kit. Another 200 μL supernatant was transferred to a new group of centrifuge tubes, each of which was added with 4 μL of 3 M HCl, placed at room temperature for 5 min and centrifuged at 12,000 rpm for 5 min at room temperature. 100 μL supernatant was sucked out and transferred to a 96-well "V" bottom plate, and 3.6 μL of 2 M Tris base (tromethamine) was added to each well, it was placed at room temperature for 5 min and centrifuged at 12,000 rpm for 2 min. The pH was approximately equal to 8.0 through detection by pH test paper.

Preparation of standard curve of 2-HG: 2-HG stock solution was diluted to 500 μM with reaction buffer, and then 200 μL was taken therefrom for a 2-fold gradient dilution, 10 concentrations in total. The following operations were same as described above, including the steps for acid treatment and alkali neutralization.

The aforementioned samples, the test cell samples or standard samples, were diluted in 5 folds, and then 5 μL of each sample was taken therefrom and added to a 384-well plate. 10 μL of the detection mixture (8 μM PHGDH (phosphoglycerate dehydrogenase); 0.5 mM NAD; 0.1 U/ml diaphorase and 10 μM resazurin) was added to each well, and they were reacted for 60 min at 23° C. Fluorescence values were determined through Flexstation 3 at Ex535/Em595.

The measured fluorescence values were compared after being corrected with the protein concentrations of the corresponding samples.

The method for determining extracellular 2-HG was as follows: 500 μL of each culture medium supernatant was taken. 10 μL of 3 M HCl was added into each tube and placed for 5 min at room temperature. Then, 18 μL of 2 M Tris base was added into each tube and placed for 5 min at room temperature. It was centrifuged at 12,000 rpm for 2 min. The pH was approximately equal to 8.0 detected by pH test paper. Preparation of standard curve of 2-HG: 2-HG stock solution was diluted to 500 μM with complete medium, and then 500 μL was taken therefrom for a 2-fold gradient dilution, 10 concentrations in total. The following operations were same as described above, including the steps for acid treatment and alkali neutralization. The aforementioned samples, the test culture supernatant samples or standard samples, were diluted in 5 folds, and then 5 μL was taken therefrom and added to a 384-well plate. 10 μL of the detection mixture (8 μM PHGDH; 0.5 mM NAD; 0.1 U/mL diaphorase and 10 μM resazurin) was added to each well and reacted for 60 min at 2300. Fluorescence values were determined through Flexstation 3 at Ex535/Em595.

The selected compounds prepared as described above were analyzed according to the biological methods herein, and the results are as follows:

1. The inhibitory activities ($IC_{50}$) of the compounds against IDH1 mutants (R132H and R132C) were shown in Table 1.

TABLE 1

| Example No. | IDH1 (R132H) $IC_{50}$ (nM) | IDH1 (R132C) $IC_{50}$ (nM) |
|---|---|---|
| 1 | <10000 | — |
| 2 | <20 | <20 |
| 3 | <500 | — |
| 4 | <20 | — |
| 5 | <1000 | — |
| 6 | <20 | — |
| 7 | <500 | — |
| 8 | <20 | — |
| 9 | <1000 | — |
| 10 | <20 | — |
| 11 | <500 | — |
| 12 | <20 | <20 |
| 13 | <1000 | — |
| 14 | <20 | — |
| 15 | <500 | — |
| 16 | <20 | — |
| 17 | <10000 | — |
| 18 | <100 | — |
| 19 | <1000 | — |

TABLE 1-continued

| Example No. | IDH1 (R132H) $IC_{50}$ (nM) | IDH1 (R132C) $IC_{50}$ (nM) |
|---|---|---|
| 20 | <20 | — |
| 21 | <10000 | — |
| 22 | <1000 | — |
| 23 | <20 | — |
| 24 | <20 | — |
| 25 | 20 | — |
| 26 | <20 | — |
| 27 | 20 | — |

Note:
— means not determined.

Figure 2:
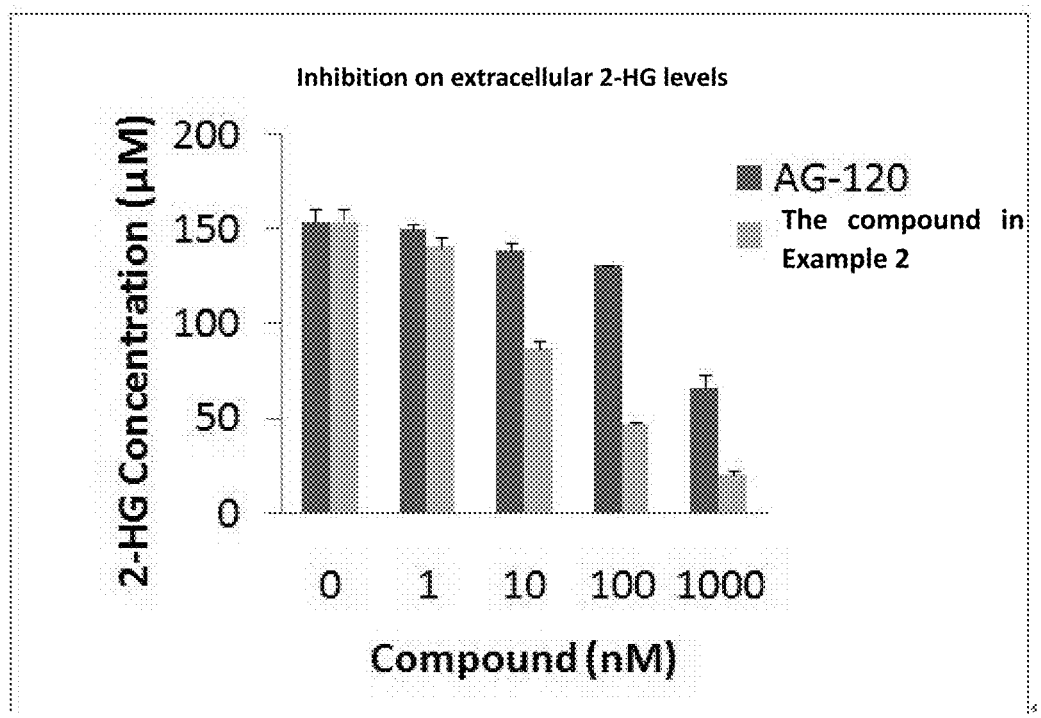
FIG. 2 shows the inhibitory results of the compound in Example 2 and control AG-120 directed to 2-HG outside IDH1-mutated HT-1080 cells.

2. The inhibitory results of the compound in Example 2 on 2-HG in IDH1-mutated HT-1080 cells were shown in FIG. 1. The inhibitory results of the compound in Example 2 on 2-HG outside IDH1-mutated HT-1080 cells were shown in FIG. 2.

Figure 3:
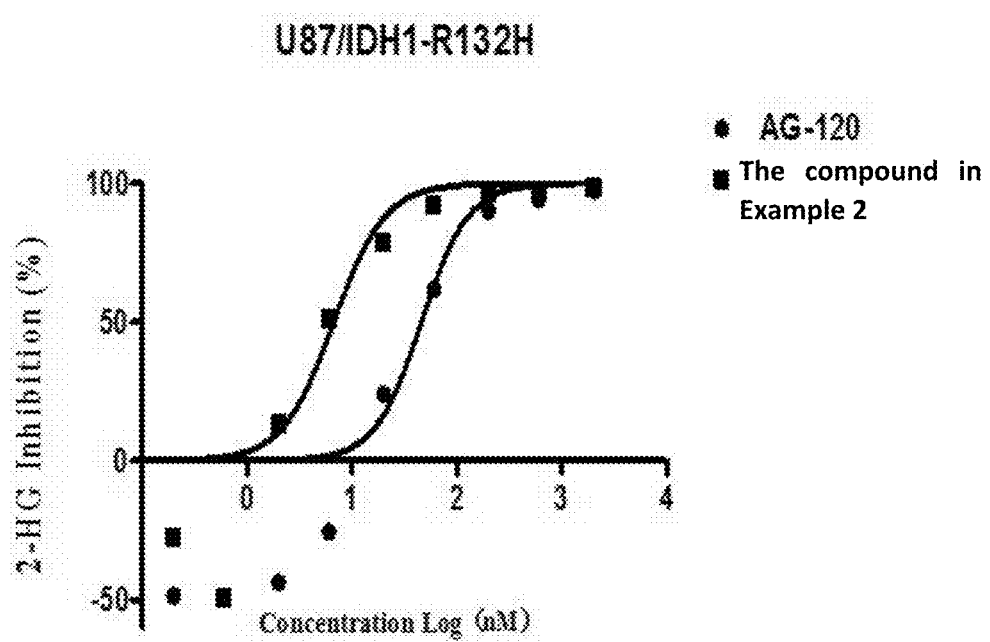
FIG. 3 shows the inhibitory results of the compound in Example 2 and control AG-120 directed to 2-HG in IDH1-mutated U87 cells.

3. The inhibitory results of the compound in Example 2 on 2-HG in IDH1-mutated U87 cells were shown in FIG. 3.

4. The inhibitory activities ($IC_{50}$) of the compound in Example 2 on IDH1-mutated U87 cells were shown in Table 2 below.

TABLE 2

| Compound | U87/IDH1 (R132H) $IC_{50}$ (nM) |
|---|---|
| AG-120 | 46 |
| The compound in Example 2 | 6.7 |

Pharmacokinetic Experiments

Male SD rats were from Beijing Vital River Laboratory Animal Technology Co., Ltd., and divided into groups (3 rats per group). The rats were intragastrically administered with the test sample suspension (5 mg/kg) via a single peroral administration, respectively. The animals were fasted overnight before this study. The fasting time period was from 10 hours before administration to 4 hours after administration. Blood samples were taken at 0.25, 0.5, 1, 2, 4, 6, 8 and 24 hours after administration. After the rats were anesthetized with isoflurane using an anesthesia machine for small animal, and then 0.3 mL whole blood samples were taken from the fundus venous plexus. The blood samples were placed in heparin anticoagulant tubes, and centrifuged for 5 min at 4° C. and 4000 rpm. The plasma was transferred to centrifuge tubes, and stored at −80° C. until analysis. The samples in plasma were extracted through protein precipitation. The liquid extract was analyzed by LC-MS/MS, wherein HPLC conditions were as follows: flow rate 0.4 mL/min; mobile phase A: water/formic acid (99.9/0.1, v/v); mobile phase B: acetonitrile/formic acid (99.9/0.1, v/v); injection volume: 5 μL; column temperature: RT; autosampler temperature: RT; run time: 2.5 min.

PK data of the compound in Example 12 and AG-120 were shown in Table 3:

TABLE 3

| | Example 12 | AG-120 |
|---|---|---|
| Gender of rats | Male | Male |
| Oral dose (mg/kg) | 5 | 5 |
| $T_{1/2}$(hr) | 10.7 | 3.28 |

TABLE 3-continued

|  | Example 12 | AG-120 |
| --- | --- | --- |
| Tmax(hr) | 4.0 | 0.67 |
| Cmax(ng/mL) | 556 | 719 |
| AUC$_{INF\_obs}$(hr*ng/mL) | 10567 | 6315 |
| Formulation of dosage forms | 0.5% MC, 0.2% Tween80 | |

From the PK data, it can be known that the compound in Example 12 had a drug exposure in plasma far higher than that of AG-120 at the same oral dose. The half-life of the compound in Example 12 was up to 10.7 hours and pharmacokinetic properties thereof were significantly superior to that of AG-120.

What is claimed is:

1. A compound represented by formula I or a pharmaceutically acceptable salt thereof,

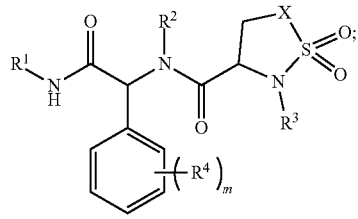

wherein,

X is $CH_2$ or $NR^5$;

$R^1$ is $C_{3-6}$ cycloalkyl or 3- to 6-membered heterocycloalkyl containing 1 to 2 heteroatoms selected from the group consisting of N, O and S, which may be optionally substituted with one or more groups $R^6$;

$R^2$ is phenyl or 5- to 6-membered heteroaryl containing 1 to 2 heteroatoms selected from the group consisting of N, O and S, which may be optionally substituted with one or more groups $R^7$;

$R^3$ is phenyl, 5- to 6-membered heteroaryl containing 1 to 2 heteroatoms selected from the group consisting of N, O and S, phenyl $CH_2$—, or 5- to 6-membered heteroaryl $CH_2$— containing 1 to 2 heteroatoms selected from the group consisting of N, O and S, which may be optionally substituted with one or more groups $R^8$;

$R^4$ is halogen, amino, hydroxyl, $C_{1-3}$ haloalkyl or $C_{1-6}$ alkyl;

$R^5$ is hydrogen or $C_{1-6}$ alkyl;

$R^6$ is halogen, amino, hydroxyl, cyano, $C_{1-3}$ haloalkyl, $C_{1-6}$ alkyl or $C_{3-6}$ cycloalkyl;

$R^7$ is halogen, amino, hydroxyl, cyano, $C_{1-3}$ haloalkyl,

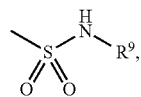

$C_{1-6}$ alkyl or $C_{3-6}$ cycloalkyl; or $R^7$ forms a O→N coordination linkage with N atom in $R^2$;

$R^8$ is halogen, amino, hydroxyl, cyano, $C_{1-3}$ haloalkyl, $C_{1-6}$ alkyl, $C_{3-6}$ cycloalkyl, $C_{2-6}$ alkenyl or $C_{2-6}$ alkynyl;

$R^9$ is H, $C_{1-6}$ alkyl, $C_{3-6}$ cycloalkyl, 3- to 6-membered heterocycloalkyl containing 1 to 2 heteroatoms selected from the group consisting of N, O, S, phenyl, or 5- to 6-membered heteroaryl containing 1 to 2 heteroatoms selected from the group consisting of N, O and S, which may be optionally substituted with one or more groups $R^{10}$;

$R^{10}$ is halogen, amino, hydroxyl, cyano, $C_{1-3}$ haloalkyl, $C_{1-6}$ alkyl or $C_{3-6}$ cycloalkyl;

m is 0 or 1.

2. The compound or the pharmaceutically acceptable salt thereof according to claim 1, wherein, X is $CH_2$ or $NR^5$;

$R^1$ is $C_{3-6}$ cycloalkyl or 3- to 6-membered heterocycloalkyl containing 1 to 2 heteroatoms selected from the group consisting of N, O and S, which may be optionally substituted with one or more groups $R^6$;

$R^2$ is phenyl or 5- to 6-membered heteroaryl containing 1 to 2 heteroatoms selected from the group consisting of N, O and S, which may be optionally substituted with one or more groups $R^7$;

$R^3$ is phenyl, 5- to 6-membered heteroaryl containing 1 to 2 heteroatoms selected from the group consisting of N, O and S, phenyl $CH_2$—, or 5- to 6-membered heteroaryl $CH_2$— containing 1 to 2 heteroatoms selected from the group consisting of N, O and S, which may be optionally substituted with one or more groups $R^8$;

$R^4$ is halogen, amino, hydroxyl, $C_{1-3}$ haloalkyl or $C_{1-6}$ alkyl;

$R^5$ is hydrogen or $C_{1-6}$ alkyl;

$R^6$ is halogen, amino, hydroxyl, cyano, $C_{1-3}$ haloalkyl, $C_{1-6}$ alkyl or $C_{3-6}$ cycloalkyl;

$R^7$ is halogen, amino, hydroxyl, cyano, $C_{1-3}$ haloalkyl, aminosulfonyl, N-substituted aminosulfonyl, $C_{1-6}$ alkyl or $C_{3-6}$ cycloalkyl;

$R^8$ is halogen, amino, hydroxyl, cyano, $C_{1-3}$ haloalkyl, $C_{1-6}$ alkyl, $C_{3-6}$ cycloalkyl, $C_{2-6}$ alkenyl or $C_{2-6}$ alkynyl;

m is 0 or 1.

3. The compound or the pharmaceutically acceptable salt thereof according to claim 1, wherein the compound is represented by formula II,

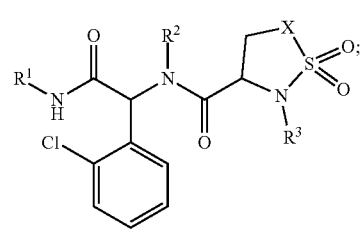

wherein,

X is $CH_2$ or $NR^5$;

$R^1$ is $C_{3-6}$ cycloalkyl or 3- to 6-membered heterocycloalkyl containing 1 to 2 heteroatoms selected from the group consisting of N, O and S, which may be optionally substituted with one or more groups $R^6$;

$R^2$ is phenyl or 5- to 6-membered heteroaryl containing 1 to 2 heteroatoms selected from the group consisting of N, O and S, which may be optionally substituted with one or more groups $R^7$;

$R^3$ is phenyl, 5- to 6-membered heteroaryl containing 1 to 2 heteroatoms selected from the group consisting of N, O and S, phenyl $CH_2$—, or 5- to 6-membered heteroaryl $CH_2$— containing 1 to 2 heteroatoms selected from the group consisting of N, O and S, which may be optionally substituted with one or more groups $R^8$;

$R^5$ is hydrogen or $C_{1-6}$ alkyl;

$R^6$ is halogen, amino, hydroxyl, cyano, $C_{1-3}$ haloalkyl, $C_{1-6}$ alkyl or $C_{3-6}$ cycloalkyl;

$R^7$ is halogen, amino, hydroxyl, cyano, $C_{1-3}$ haloalkyl,

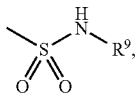

$C_{1-6}$ alkyl or $C_{3-6}$ cycloalkyl; or $R^7$ forms a O→N coordination linkage with N atom in $R^2$, $R^7$ is halogen, amino, hydroxyl, cyano, $C_{1-3}$ haloalkyl, $C_{1-6}$ alkyl, $C_{3-6}$ cycloalkyl, $C_{2-6}$ alkenyl or $C_{2-6}$ alkynyl;

$R^9$ is H, $C_{1-6}$ alkyl, $C_{3-6}$ cycloalkyl, 3- to 6-membered heterocycloalkyl containing 1 to 2 heteroatoms selected from the group consisting of N, O and S, phenyl, or 5- to 6-membered heteroaryl containing 1 to 2 heteroatoms selected from the group consisting of N, O and S, which may be optionally substituted with one or more groups $R^{10}$;

$R^{10}$ is halogen, amino, hydroxyl, cyano, $C_{1-3}$ haloalkyl, $C_{1-6}$ alkyl or $C_{3-6}$ cycloalkyl.

4. The compound or the pharmaceutically acceptable salt thereof according to claim 3, wherein, X is $CH_2$ or $NR^5$;

$R^1$ is $C_{3-6}$ cycloalkyl or 3- to 6-membered heterocycloalkyl containing 1 to 2 heteroatoms selected from the group consisting of N, O and S, which may be optionally substituted with one or more groups $R^6$;

$R^2$ is phenyl or 5- to 6-membered heteroaryl containing 1 to 2 heteroatoms selected from the group consisting of N, O and S, which may be optionally substituted with one or more groups $R^7$;

$R^3$ is phenyl, 5- to 6-membered heteroaryl containing 1 to 2 heteroatoms selected from the group consisting of N, O and S, phenyl $CH_2$—, or 5- to 6-membered heteroaryl $CH_2$— containing 1 to 2 heteroatoms selected from the group consisting of N, O and S, which may be optionally substituted with one or more groups $R^8$;

$R^5$ is hydrogen or $C_{1-6}$ alkyl;

$R^6$ is halogen, amino, hydroxyl, cyano, $C_{1-3}$ haloalkyl, $C_{1-6}$ alkyl or $C_{3-6}$ cycloalkyl;

$R^7$ is halogen, amino, hydroxyl, cyano, $C_{1-3}$ haloalkyl, aminosulfonyl, N-substituted aminosulfonyl, $C_{1-6}$ alkyl or $C_{3-6}$ cycloalkyl;

$R^8$ is halogen, amino, hydroxyl, cyano, $C_{1-3}$ haloalkyl, $C_{1-6}$ alkyl, $C_{3-6}$ cycloalkyl, $C_{2-6}$ alkenyl or $C_{2-6}$ alkynyl.

5. The compound or the pharmaceutically acceptable salt thereof according to claim 1, X is $CH_2$, NH or $N(CH_3)$.

6. The compound or the pharmaceutically acceptable salt thereof according to claim 1, $R^5$ is hydrogen, methyl, ethyl, propyl, isopropyl, butyl, isobutyl or tert-butyl.

7. The compound or the pharmaceutically acceptable salt thereof according to claim 1, $R^1$ is cyclopropyl, cyclobutyl, cyclopentyl, cyclohexyl, pyrrolidinyl or piperidyl, which may be optionally substituted with one or more groups $R^6$.

8. The compound or the pharmaceutically acceptable salt thereof according to claim 1, $R^6$ is F, Cl or Br.

9. The compound or the pharmaceutically acceptable salt thereof according to claim 1, $R^2$ is phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl or triazinyl, which may be optionally substituted with one or more groups $R^7$.

10. The compound or the pharmaceutically acceptable salt thereof according to claim 1, wherein $R^2$ is phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl or triazinyl, which may be optionally substituted with one or more groups $R^7$; $R^7$ is F, Cl, Br, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl, aminosulfonyl or N-substituted aminosulfonyl.

11. The compound or the pharmaceutically acceptable salt thereof according to claim 1, $R^7$ is F, Cl, Br, cyano, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl, or

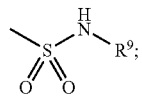

or $R^7$ forms a O→N coordination linkage with N atom in $R^2$.

12. The compound or the pharmaceutically acceptable salt thereof according to claim 1, $R^9$ is H, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl or triazinyl, which may be optionally substituted with one or more groups $R^{10}$.

13. The compound or the pharmaceutically acceptable salt thereof according to claim 1, $R^3$ is phenyl, furyl, thienyl, pyrrolyl, pyrazolyl, imidazolyl, pyridyl, pyrimidyl, pyridazinyl, pyrazinyl, thiazolyl, isothiazolyl, oxazolyl, isoxazolyl, tetrazolyl, triazinyl, benzyl, furanylmethylene, thienylmethylene, pyrrolylmethylene, pyrazolylmethylene, imidazolylmethylene, pyridylmethylene, pyrimidinylmethylene, pyridazinylmethylene, pyrazinylmethylene, thiazolylmethylene, isothiazolylmethylene, oxazolylmethylene, isoxazolylmethylene, tetrazolylmethylene or triazinylmethylene, which may be optionally substituted with one or more groups $R^8$.

14. The compound or the pharmaceutically acceptable salt thereof according to claim 1, $R^8$ is F, Cl, Br, cyano, ethynyl, 1-propynyl or 1-butynyl.

15. The compound or the pharmaceutically acceptable salt thereof according to claim 1, wherein the compound is as follows:

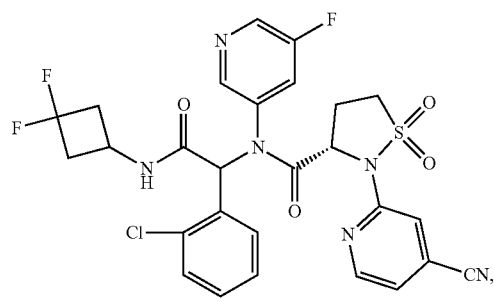

71
-continued
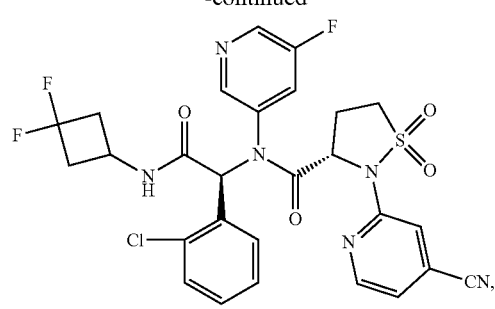
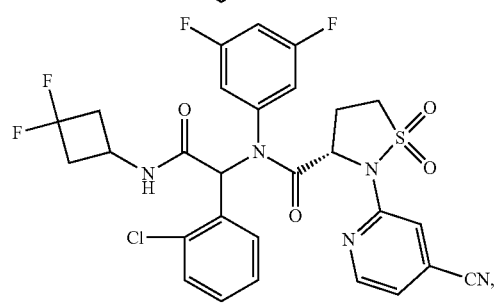
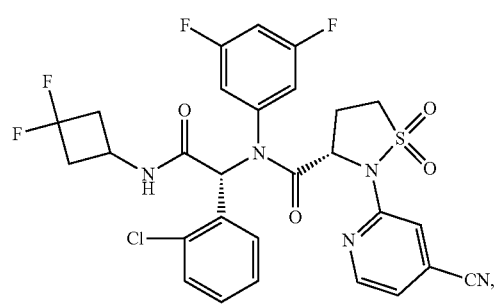
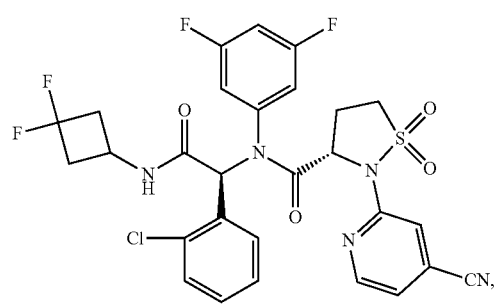
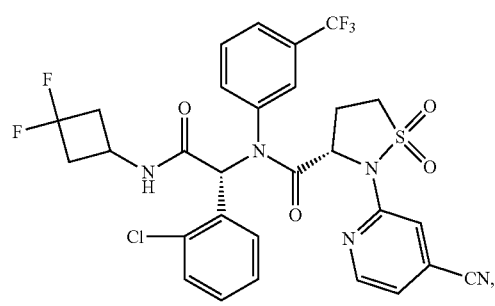
72
-continued
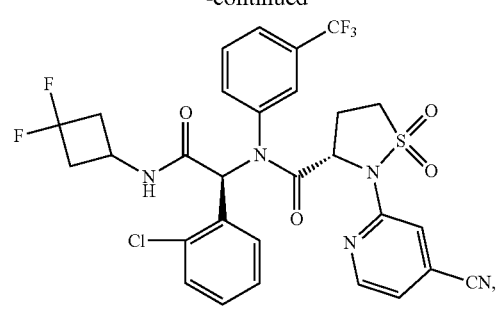
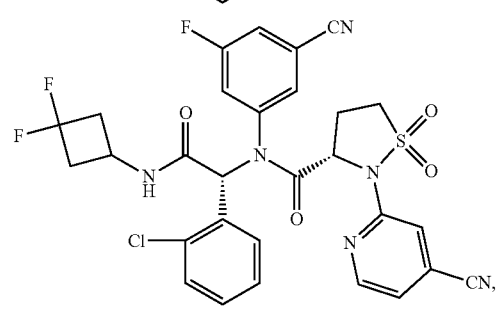
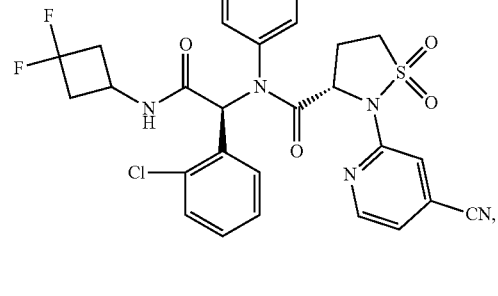
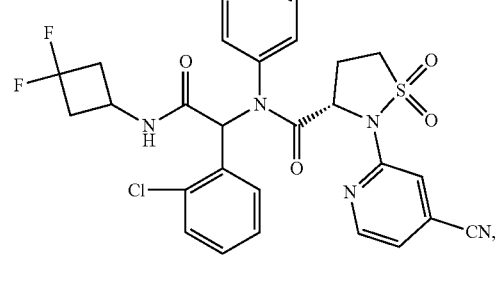
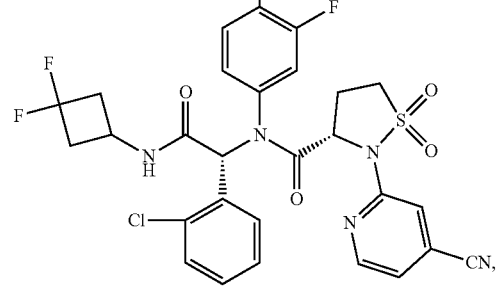

73
-continued
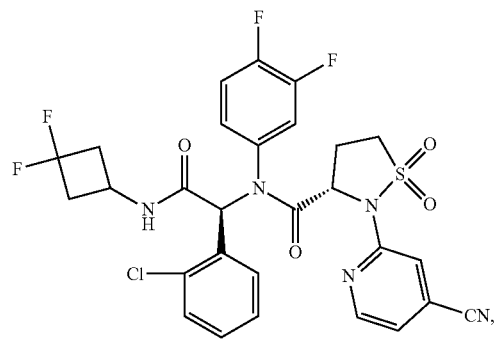
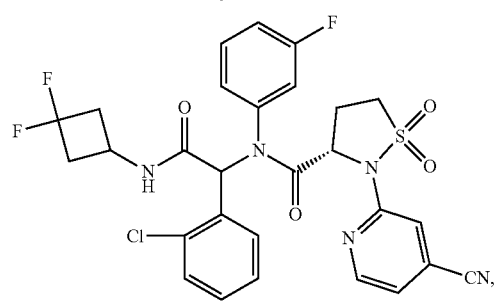
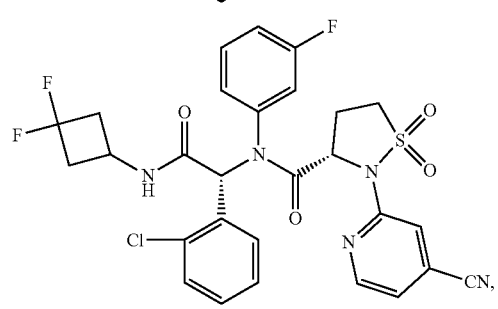
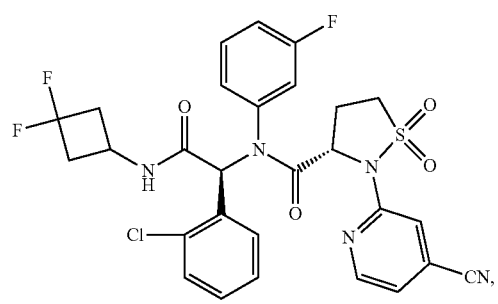
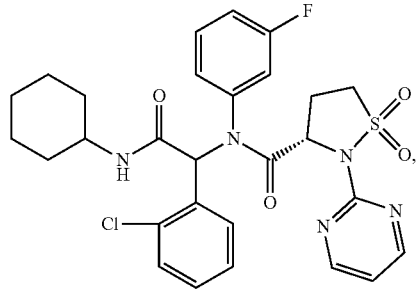
74
-continued
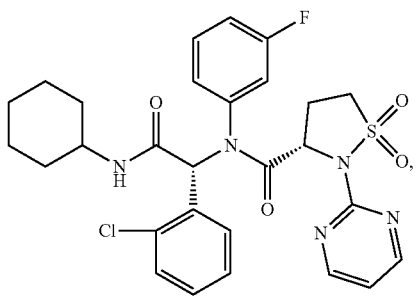
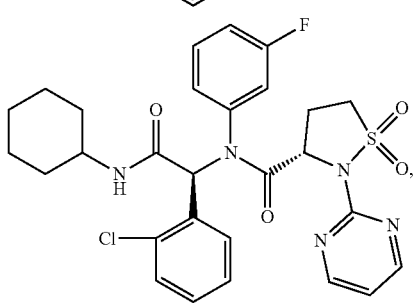
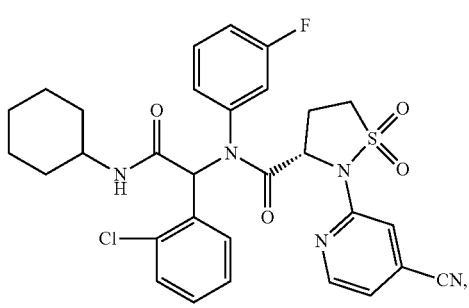
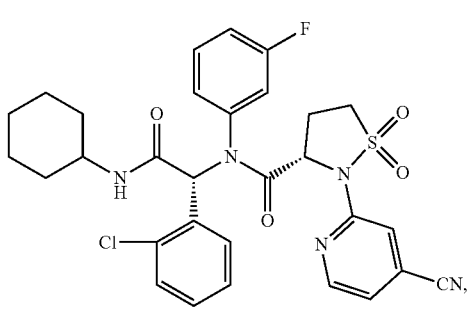
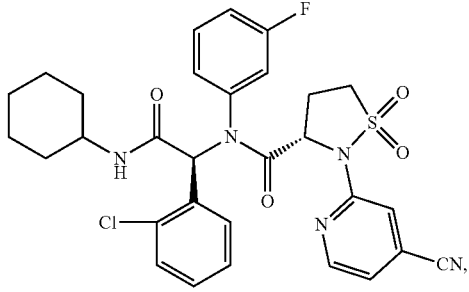

75
-continued
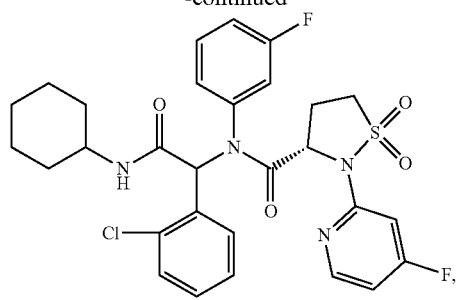
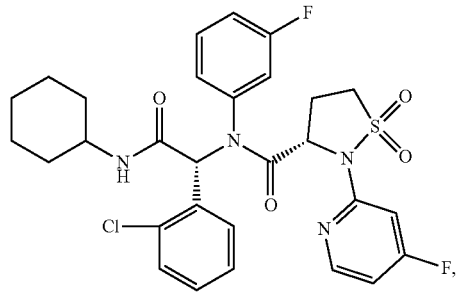
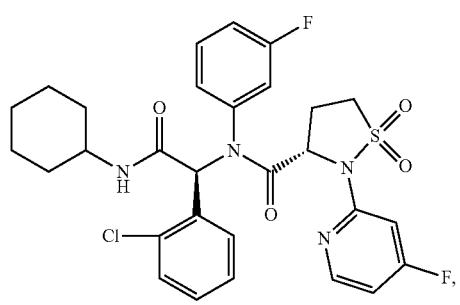
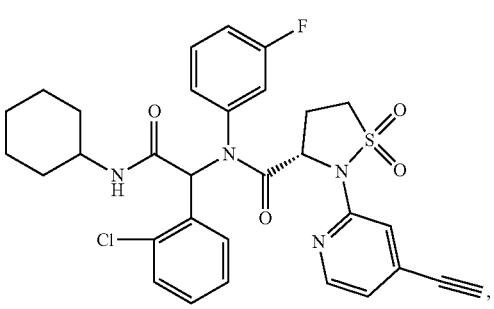
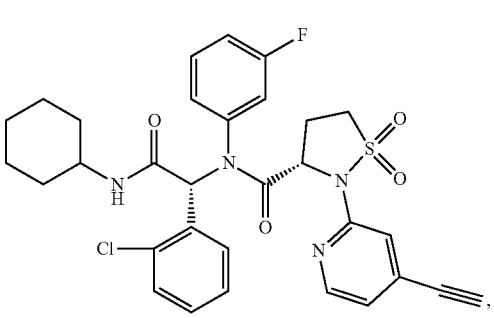
76
-continued
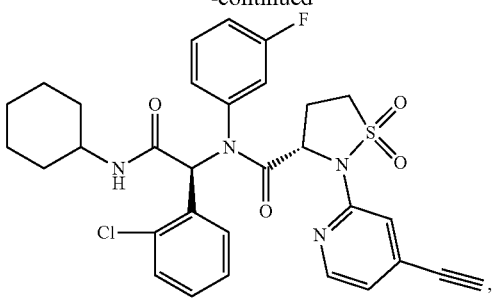
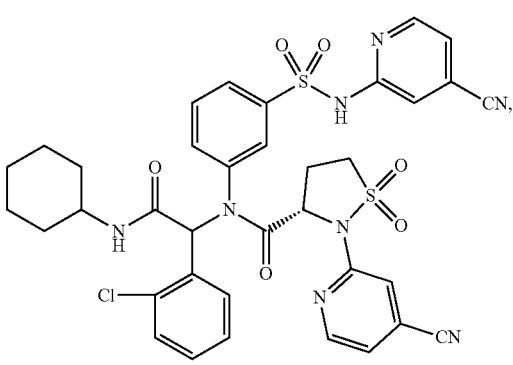
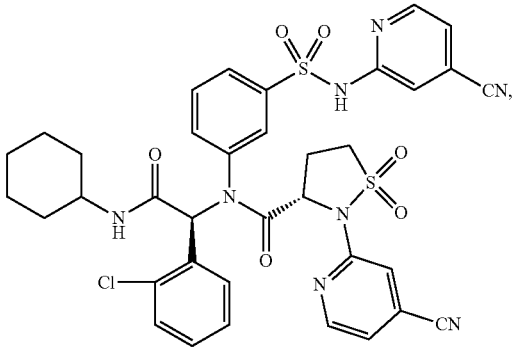
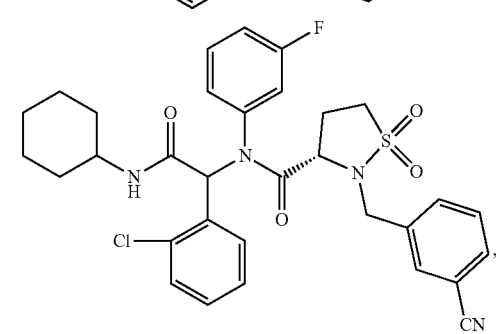
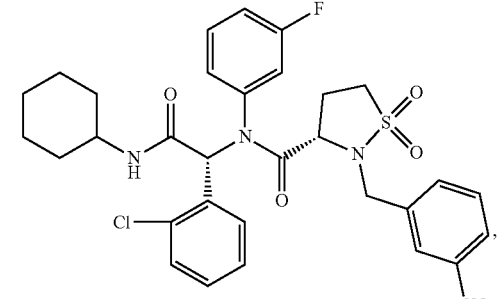

77
-continued
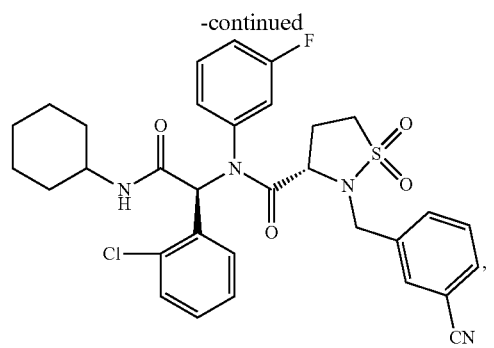
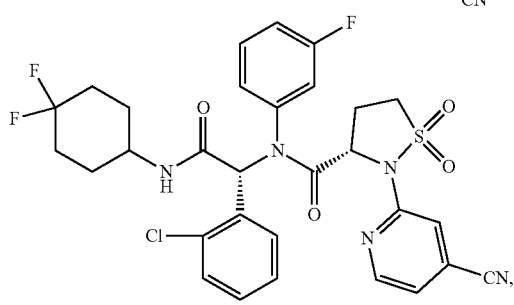
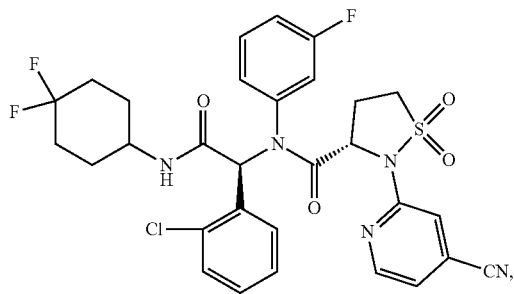
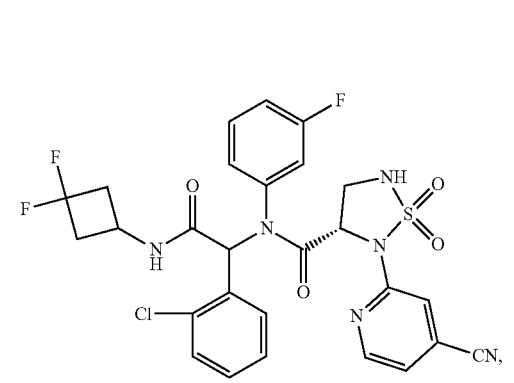
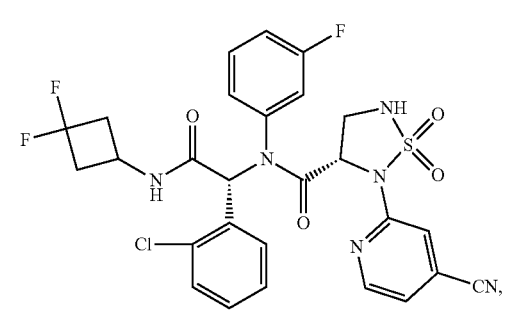
78
-continued
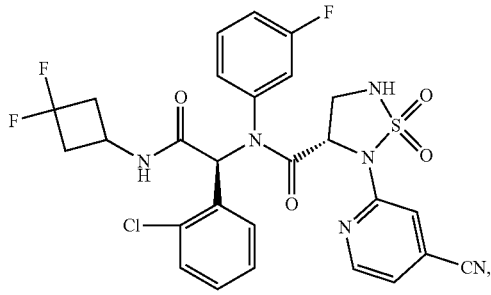
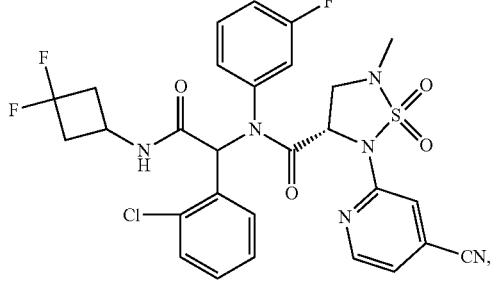
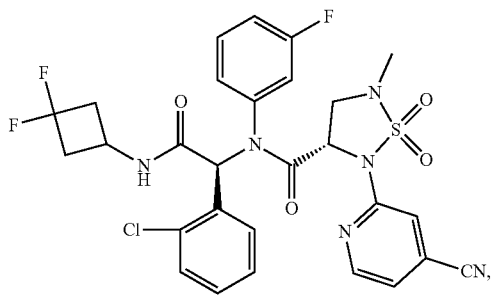
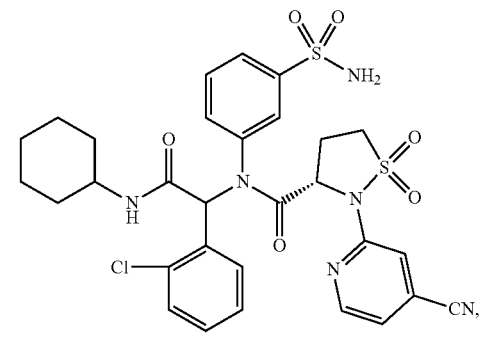
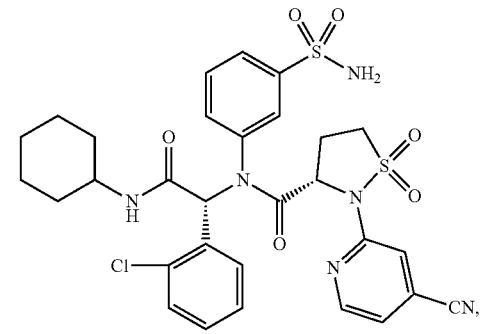

-continued

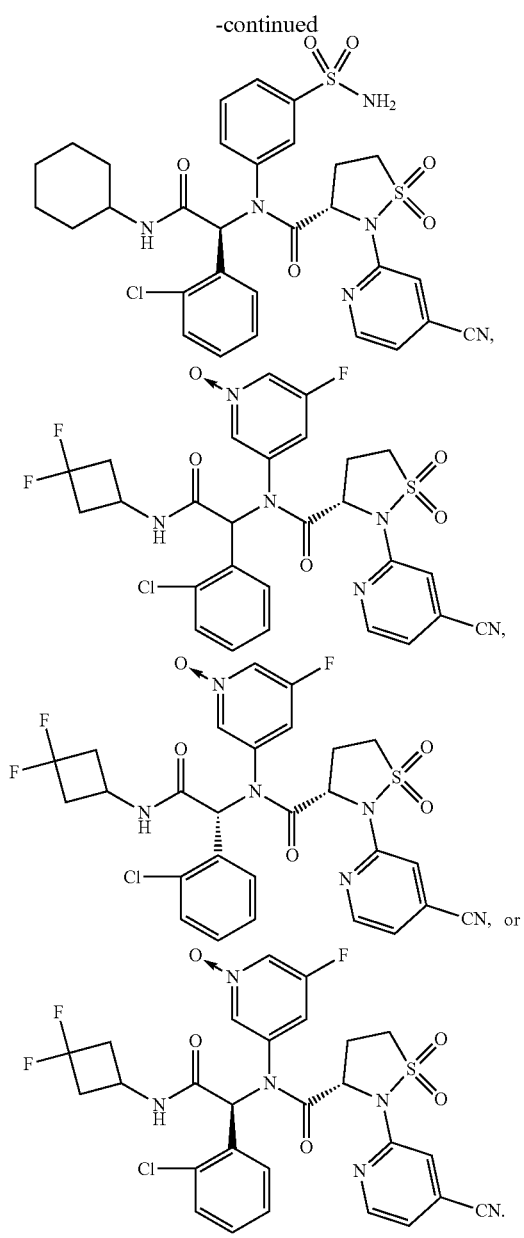

16. A method for treating IDH1 mutation-induced cancers comprising administering a therapeutically effective amount of the compound or the pharmaceutically acceptable salt thereof according to claim 1 to a patient in need thereof, wherein the IDH1 mutation has R132X mutation; and the IDH1 mutation-induced cancers are selected from the group consisting of glioblastoma, myelodysplastic syndrome, myeloproliferative neoplasm, acute myelogenous leukemia, sarcoma (preferably chondrosarcoma, fibrosarcoma), melanoma, non-small cell lung cancer, bile duct cancer or angioimmunoblastic non-Hodgkin's lymphoma.

17. A pharmaceutical composition, which comprises a therapeutically effective amount of the compound or the pharmaceutically acceptable salt thereof according to claim 1 and one or more pharmaceutically acceptable carriers or excipients.

18. The compound or the pharmaceutically acceptable salt thereof according to claim 7, $R^1$ is

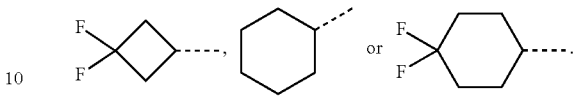

19. The compound or the pharmaceutically acceptable salt thereof according to claim 9, $R^2$ is

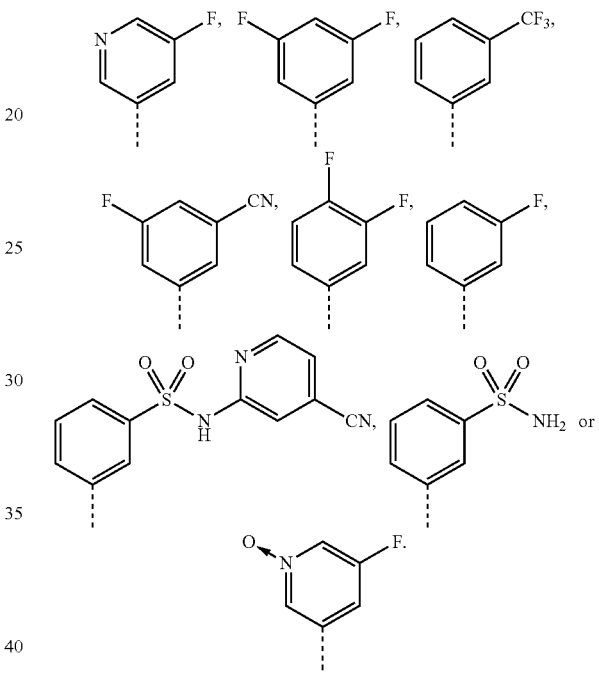

20. The compound or the pharmaceutically acceptable salt thereof according to claim 13, $R^3$ is

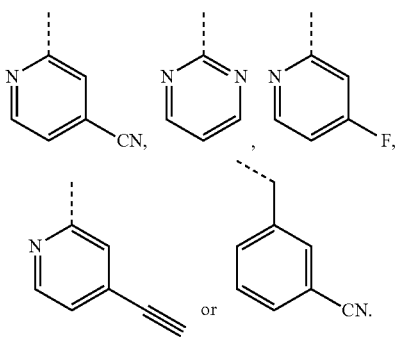

* * * * *

UNITED STATES PATENT AND TRADEMARK OFFICE
CERTIFICATE OF CORRECTION

PATENT NO. : 11,111,240 B2
APPLICATION NO. : 16/086721
DATED : September 7, 2021
INVENTOR(S) : Li Zhu et al.

Page 1 of 1

It is certified that error appears in the above-identified patent and that said Letters Patent is hereby corrected as shown below:

In the Claims

At Column 69, Line 13 (Claim 3, approximately Line 26), please delete "$R^7$ is halogen" and insert --$R^8$ is halogen-- therefor.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*